(12) United States Patent
Ogata et al.

(10) Patent No.: US 7,655,227 B1
(45) Date of Patent: Feb. 2, 2010

(54) AGENTS FOR AMELIORATING LOW VASOPRESSIN LEVEL

(75) Inventors: Etsuro Ogata, Tokyo (JP); Etsuro Onuma, Shizuoka (JP); Toshiaki Tsunenari, Shizuoka (JP); Hidemi Saito, Shizuoka (JP); Yumiko Azuma, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/019,501

(22) PCT Filed: Jul. 3, 2000

(86) PCT No.: PCT/JP00/04413

§ 371 (c)(1),
(2), (4) Date: Dec. 31, 2001

(87) PCT Pub. No.: WO01/02010

PCT Pub. Date: Jan. 11, 2001

(51) Int. Cl.
*A61K 39/395* (2006.01)
*A61K 38/22* (2006.01)
*C07K 16/26* (2006.01)
*C12P 21/08* (2006.01)

(52) U.S. Cl. .............. 424/133.1; 424/130.1; 424/139.1; 424/141.1; 424/145.1

(58) Field of Classification Search .............. 424/184.1, 424/133.1, 134.1, 143.1
See application file for complete search history.

(56) References Cited

U.S. PATENT DOCUMENTS

| 4,771,124 | A | 9/1988 | Rosenblatt et al. | |
| 4,946,778 | A * | 8/1990 | Ladner et al. | 435/69.6 |
| 5,001,223 | A | 3/1991 | Rosenblatt et al. | |
| 5,217,896 | A | 6/1993 | Kramer et al. | |
| 5,626,845 | A | 5/1997 | Yoneda et al. | |
| 5,849,695 | A | 12/1998 | Cohen et al. | |
| 5,993,817 | A | 11/1999 | Yoneda et al. | |
| 6,180,370 | B1 * | 1/2001 | Queen et al. | 435/69.6 |
| 6,903,194 | B1 * | 6/2005 | Sato et al. | 530/387.1 |

FOREIGN PATENT DOCUMENTS

| CA | 2266332 | * 4/1998 |
| EP | 0 293 130 | 11/1988 |
| EP | 0293 158 | 11/1988 |
| EP | 0 449 405 | 10/1991 |
| EP | 0 811 383 | 12/1997 |
| EP | 0 878 201 A1 | 11/1998 |
| EP | 0 962 467 A1 | 12/1999 |
| EP | 1 004 313 A1 | 5/2000 |
| EP | 1 090 643 A1 | 4/2001 |
| JP | 2-207099 | 8/1990 |
| JP | 4-502408 | 5/1992 |
| JP | 4-228089 | 8/1992 |
| JP | 7-165790 | 6/1995 |
| JP | 7-316195 | 12/1995 |
| JP | 11-80025 | 3/1999 |
| JP | 11-222440 | 8/1999 |
| JP | 2000-080100 | 3/2000 |
| WO | WO 89/11297 | 11/1989 |
| WO | WO 89/11298 | 11/1989 |
| WO | WO 90/07861 | 7/1990 |
| WO | WO 91/16928 | 11/1991 |
| WO | WO 92/00753 | 1/1992 |
| WO | WO 92/17602 | 10/1992 |
| WO | WO 93/13133 | 7/1993 |
| WO | WO 94/11523 | 5/1994 |
| WO | WO 96/03437 | 2/1996 |
| WO | WO 96/39184 | 2/1996 |
| WO | WO 96/22790 | 8/1996 |
| WO | WO 96/26737 | 9/1996 |
| WO | WO 96/33735 | 10/1996 |
| WO | WO 98/13388 | 4/1998 |
| WO | WO 98/51329 | 11/1998 |
| WO | WO 99/57139 | 11/1999 |
| WO | WO 00/00219 | 1/2000 |

OTHER PUBLICATIONS

Stryer et al, in Biochemistry, Third edition, W H Freeman Company, New York, pp. 31-33, 1998.*
Ngo et al, 1994, The Protein Folding Problem and Tertiary Structure Prediction, pp. 492-495.*
Kuby et al., 1994, Immunology, second edition, pp. 85-96.*
Abaza et al, J of Protein Chemistry 11(5): 433-444, 1992.*
Harlow et al, in Antibodies a Laboratory Manual, 1988, Cold Spring harbor laboratory publication, Cold Spring Harobr, NY, pp. 626-629.*
Hotta et al, Endocr J 45(6): 773-8, Dec. 1998.*
Kitamura et al, Biochem Biophys Res Commun 171(3): 1387-94, Sep. 1990.*
Banerjiee et al, J Immunology 169: 5137-5144, 2002.*
Rudikoff et al, Proc Natl Acad Sci USA 1982 vol. 79 p. 1979.*
Wu et al. J. Mol. Biol. 294: 151-162, 1999.*
Kobrin et al, J Immunology 146: 2017-2020, 1991.*
Barrios et al, J Molecular Recognition 17: 332-338, 2004.*
Caldwell et al, Progress in Neurobiology 84: 1-24, 2008.*
U.S. Appl. No. 09/269,332, filed Mar. 25, 1999, Sato et al.
Etsuro Ogata, M.D., Ph. D., "Parathyroid Hormone-Related Protein as a Potential Target of Therapy for Cancer-Associated Morbidity", Cancer Supplement vol. 88, No. 12, pp. 2909-2911. Jun. 15, 2000.
U.S. Appl. No. 09/423,800, filed Nov. 12, 1999, Sato et al.
U.S. Appl. No. 09/720,326, filed Dec. 22, 2000, Sato et al.

(Continued)

*Primary Examiner*—Phuong Huynh
(74) *Attorney, Agent, or Firm*—Oblon, Spivak, McClelland, Maier & Neustadt, L.L.P.

(57) ABSTRACT

The present invention provides an agent for ameliorating low vasopressin level, which comprises, as an active ingredient, a substance capable of inhibiting the binding between parathyroid hormone-related peptide (PTHrP) and a receptor thereof; and an agent for ameliorating a symptom caused by a decrease in vasopressin level, which comprises, as an active ingredient, a substance capable of inhibiting the binding between parathyroid hormone-related peptide (PTHrP) and a receptor thereof.

4 Claims, 3 Drawing Sheets

OTHER PUBLICATIONS

Abou-Samra et al., Expression Cloning of a Common Receptor for Parathyroid Hormone and Parathyroid Hormone-Related Peptide from Rat Osteoblast-Like Cells: A Single Receptor Stimulates Intracellular Accumulation of Both cAMP and Inositol Trisphosphates and Increases Intracellular Free Calcium, *Proceedings of the National Academy of Sciences*, 89:2732-2736 (1992).

Baba, PTH/PTHrP, *Clinical Calcium*, 5:97-101 (1995) (English Translation).

Beck, et al., Lipolytic Factors Associated with Murine and Human Cancer Cachexia, *Journal of the National Cancer Institute*, 82:1922-1926 (1990).

Belyavsky et al., PCR-Based cDNA Library Construction: General cDNA Libraries at the Level of a Few Cells, *Nucleic Acids Research*, 17:2919-2933 (1989).

Burtis, Parathyroid Hormone-Related Protein: Structure, Function, and Measurement, *Clinical Chemistry*, 38:2171-2183 (1992).

Carter et al., Humanization of an Anti-p185$^{HER2}$ Antibody for Human Cancer Therapy, *Proceedings of the National Academy of Sciences*, 89:4285-4289 (1992).

Chirgwin et al., Isolation of Biologically Active Ribonucleic Acid From Sources Enriched in Ribonuclease, *Biochemistry*, 18:5294-5299 (1979).

Chomczynski et al., Single-Step Method of RNA Isolation By Acid Guanidinium Thiocyanate-Phenol-Chloroform Extraction, *Analytical Biochemistry*, 162:156-159 (1987).

Chothia, Canonical Structures for the Hypervariable Regions of Immunoglobulins, *Journal Molecular Biology*, 196:901-917 (1987).

Co et al., Chimeric and Humanized Antibodies with Specificity for the CD33 Antigen, *The Journal of Immunology*, 148:1149-1154 (1992).

Co et al., Humanized Antibodies for Antiviral Therapy, *Proceedings of the National Academy of Sciences*, 88:2869-2873 (1991).

Coleman et al., Biochemical Mechanisms of Parathyroid Hormone Action, *The Parathyroids, Basic and Clinical Concepts*, 239-258 (1994). Chapter 16, Raven Press NY.

Cuisinier et al., Mechanisms That Generate Human Immunoglobulin Diversity Operate From the 8$^{th}$ Week of Gestation in Fetal Liver, *European Journal of Immunology*, 23:110-118 (1993).

Dariavach et al., Human Immunoglobulin $C_\lambda 6$ Gene Encodes the Kern$^+$Oz $\lambda$ Chain and $C_\lambda 4$ and $C_\lambda 5$ are Pseudogenes, *Proceedings of the National Academy of Sciences*, 84:9074-9078 (1987).

Deftos et al., Utilization of a Potentially Universal Downstream Primer in the Rapid Identification and Characterization of V$\lambda$ Genes From Two New Human V$\lambda$ Families, *Scandinavian Journal of Immunology*, 39:95-103 (1994).

de St. Groth, et al., Production of Monoclonal Antibodies: Strategy and Tactics, *Journal of Immunological Methods*, 35:1-21 (1980).

Dworkin et al., Dietary Intake in Patients with Acquired Immunodeficiency Syndrome (AIDS), Patients with AIDS-Related Complex, and Serologically Positive Human Immunodeficiency Virus Patients: Correlations with Nutritional Status, *Journal of Parenteral and Enteral Nutrition*, 14:605-609 (1990).

Farmer et al., Speculations on the Design of Nonpeptidic Peptidomimetics, *TIPS*, 4:362-365, (1982).

Frohman et al., Rapid Production of Full-Length cDNAs From Rare Transcripts: Amplification Using a Single Gene-Specific Oligonucleotide Primer, *Proceedings of the National Academy of Sciences*, 85:8998-9002 (1998).

Galfrè et al., Rat × Rat Hybrid Myelomas and A Monoclonal Anti-Fd Portion of Mouse IgG, *Nature*, 277:131-133 (1979).

Gorman et al., Reshaping a Therapeutic CD4 Antibody, *Proceedings of the National Academy of Sciences*, 88:4181-4185 (1991).

Hammond et al., Respiratory Muscle Strength in Congestive Heart Failure, *Chest*, 98:1091-1094 (1990).

Hardman et al., *Goodman & Gilman's The Pharmacological Basis of Therapeutics*, 9$^{th}$ ed., McGraw-Hill Co. (USA), pp. 1528-1529 (1995).

Hardman et al., *Goodman & Gilman's The Pharmacological Basis of Therapeutics*, 9$^{th}$ ed., McGraw-Hill Co. (USA), pp. 1523-1524 (1995).

Hardman et al., *Goodman & Gilman's The Pharmacological Basis of Therapeutics*, 8$^{th}$ ed., McGraw-Hill Co. (USA), pp. 3-32 (1990).

Harris et al., Therapeutic Antibodies—The Coming of Age, *TIBTECH*, 11:42-44 (1993).

Ikeda, Molecular Biology of Parathyroid Hormone-Related Peptide, *Nihon Rinshou*, 53:37-45 (1995) (English Abstract).

Ikeda, Development of Novel Endocrinotherapy Targeting Cancer and Paraneoplastic Syndromes, *Progress in Clinical Pharmacology*, 16:155-161 (1995) (English Abstract).

Jones et al., Rapid PCR-Cloning of Full-Length Mouse Immunoglobulin Variable Regions, *Bio/Technology*, 9:88-89 (1991).

Jüppner et al., A G Protein-Linked Receptor for Parathyroid Hormone and Parathyroid Hormone-Related Peptide, *Science*, 254:1024-1026 (1991).

Kaji et al., Role of Dual Signal Transduction Systems in the Stimulation of Bone Resorption by Parathyroid Hormone-Related Peptide, The Direct Involvement of cAMP-Dependent Protein Kinase, *Horm. Metab. Res.*, 25:421-424 (1993).

Kajimura et al., Toxohormones Responsible for Cancer Cachexia Syndrome in Nude Mice Bearing Human Cancer Cell Lines, *Cancer Chemother Pharmacol*, 38:S48-S52 (1996).

Karlsson et al., Kinetic Analysis of Monoclonal Antibody-Antigen Interactions with a New Biosensor Based Analytical System, *Journal of Immunological Methods*, 145:229-240 (1991).

Kato et al., Incisor Change Induced by Excessive PTHrP in Rats, *Abstracts of 16$^{th}$ Meeting of Japanese Society of Toxicologic Pathology*, p. 17 (2000) (English Translation).

Kearney et al., A New Mouse Myeloma Cell Line That Has Lost Immunoglobulin Expression But Permits the Construction of Antibody-Secreting Hybrid Cell Lines, *The Journal of Immunology*, 123:1548-1550 (1979).

Kemp et al., Parathyroid Hormone-Related Protein of Malignancy: Active Synthetic Fragments, *Science*, 238:1568-1570 (1987).

Kettleborough et al., Humanization of a Mouse Monoclonal Antibody by CDR-Grafting: The Importance of Framework Residues on Loop Conformation, *Protein Engineering*, 4:773-738 (1991).

Köhler et al., Derivation of Specific Antibody-Producing Tissue Culture and Tumor Lines by Cell Fusion, *European Journal of Immunology*, 6:511-519 (1976).

Kozak, At Least Six Nucleotides Preceding the AUG Initiator Condon Enhance Translation in Mammalian Cells, *Journal of Molecular Biology*, 196:947-950 (1987).

Kukreja et al., Tumor Resection and Antibodies to Parathyroid Hormone-Related Protein Cause Similar Changes on Bone Histomorphometry in Hypercalcemia of Cancer, *Endocrinology*, 127(1):305-310 (1990).

Kukreja et al., Antibodies to Parathyroid Hormone-Related Protein Lower Serum Calcium in Athymic Mouse Models of Malignancy-Associated Hypercalcemia Due to Human Tumors, *The Journal of Clinical Investigation*, 82:1798-1802 (1988).

Liu et al., Developmental Role of PHTrP in Murine Molars, *European Journal Oral Sciences*, 106 (suppl 1):143-146 (1998).

LoBuglio et al., Mouse/Human Chimeric Monoclonal Antibody in Man; Kinetics and Immune Response, *Proceedings of the National Academy of Sciences*, 86:4220-4224 (1989).

Lundgren et al., Parathyroid Hormone (1-34) Receptor-Binding and Second-Messenger Response in Rat Incisor Odontoblasts, *Calcif. Tissue Int.*, 62:255-259 (1998).

Maeda et al., Construction of Reshaped Human Antibodies with HIV-Neutralizing Activity, *Human Antibodies and Hybridomas*, 2:124-134 (1991).

Margulies et al., Somatic Cell Hybridization of Mouse Myeloma Cells, *Cell*, 8:405-415 (1976).

Marosi et al., Fatal Encephalitis in a Patient with Chronic Graft-Versus Host Disease, *Bone Marrow Transplantation*, 6:53-57 (1990).

Mizushima et al., pEFBOS, A Powerful Mammalian Expression Vector, *Nucleic Acids Research*, 18:5322 (1990).

Morimoto, PTH/PTHrP, *Clinical Calcium*, 5(12):50-54 (1995) (English Translation).

Moseley et al., Parathyroid Hormone-Related Protein Purified from A Human Lung Cancer Cell Line, *Proceedings of the National Academy of Sciences*, 84:5048-5052 (1987).

Mountain et al., Engineering Antibodies for Therapy, *Biotechnol Genet Eng Rev.,* 10:1-142 (1992).

Muller et al., Uberwachung und Handhabung von Zentrainervosen und Intestinalen System zur Behandlung der Tumorkachexie, *Langenbecks Arch Chir Suppl II,* pp. 261-265 (1990) (English Abstract).

Mulligan et al., Synthesis of Rabbit β-globin in Cultured Monkey Kidney Cells Following Infection with a SV40 β-globin Recombinant Genome, *Nature,* 277:108-114 (1979).

Natsume et al., Binding Assay and Analysis of Kinetic Parameters by Bialcore Biosensor, *Experimental Medicine,* 13:85-91 (1995) (English Translation).

Ogata, Parathyroid Hormone-Related Protein as a Potential Target of Therapy for Cancer-Associated Morbidity, *Cancer,* 88:2902-2911 (2000).

Ohtomo et al., Humanization of Mouse ONS-M21 Antibody with the Aid of Hybrid Variable Regions, *Molecular Immunology,* 32:407-416 (1995).

Olstad et al., Expression and Characterization of a Recombinant Human Parathyroid Partial Agonist with Antagonistic Properties: Gly-hPTH(-1→+84), *Peptides,* 16:1031-1037 (1995).

Palmieri et al., Muscle Calcium Accumulation in Muscular Dystrophy, Intracell. Calcium Regul., Proc. Int. Symp., pp. 335-347 (1986).

Philbrick et al., Parathyroid Hormone-Related Protein is Required for Tooth Eruption, *Proc. National Academy of Science USA,* 95:11846-11851 (1998).

Queen et al., A Humanized Antibody that Binds to the Interleukin 2 Receptor, *Proc. National Academy of Science USA,* 86:10029-10033 (1989).

Riechmann et al., Reshaping Human Antibodies for Therapy, *Nature,* 332:323-327 (1988).

Roe et al., A Photometric Method for the Determination of Insulin in Plasma and Urine, *Journal of Biological Chemistry,* 173:839-845 (1949).

Rosen et al., The Effect of PTH Antagonist BIM-44002 on Serum Calcium and PTH Levels in Hypercalcemic Hyperparathyroid Patients, *Calcified Tissue international,* 61:455-459 (1997).

Roubini et al., Synthesis of Fully Active Biotinylated Analogues of Parathyroid Hormone and Parathyroid Hormone-Related Protein as Tools for the Characterization of Parathyroid Hormone Receptors, *Biochemistry,* 31:4026-4033 (1992).

Sato et al., Passive Immunization with Anti-Parathyroid Hormone-Related Protein Monoclonal Antibody Markedly Prolongs Survival Time of Hypercalemic Nude Mice Bearing Transplanted Human PTHrP-Producing Tumors, *Journal of Bone and Mineral Research,* 8:849-860 (1993).

Sato et al., Reshaping a Human Antibody to Inhibit the Interleukin 6-dependent Tumor Cell Growth, *Cancer Research,* 53:851-856 (1993).

Sato et al., A Highly Sensitive Bioassay for PTH Using ROS 17/2.8 Subclonal Cells, *Acta Endocrinologica,* 116:113-120 (1987).

Sato, Malignancy-associated Hypercalcemia: Pathogenesis and Treatment, *Journal of Tokyo Women's Medical College,* 58(9):939-946 (1988) (English Abstract).

Saito et al., Potential Involvement of PHTrP in Cancer Cachexia, *Japanese Journal of Cancer Research,* 90 (Suppl.): Abstract No. 2195 (1999) (English Abstract).

Shigeno, PTH/PTHrP Receptor, *Clinical Calcium,* 5(3):79-83 (1995) (English Translation).

Shulman et al., A Better Cell Line for Making Hybridomas Secreting Specific Antibodies, *Nature,* 276:269-270 (1978).

Stewart et al., Clinical Review 16: Parathyroid Hormone-Related Proteins: Coming of Age in the 1990s, *Journal of Clinical Endocrinology and Metabolism,* 71:1410-1414 (1990).

Strewler, The Physiology of Parathyroid Hormone-Related Protein, *The New England Journal of Medicine,* 342(3):177-185 (2000).

Sumiya et al., Hypercalcemia with Malignant Tumor, *Saishin Igaku,* 46(2):315-324 (1991) (English Abstract).

Suva et al., A Parathyroid Hormone-Related Protein Implicated in Malignant Hypercalcemia: Cloning and Expression, *Science,* 237:893-896 (1987).

Takahashi et al., Structure of Human Immunoglobulin Gamma Genes: Implications for Evolution of a Gene Family, *Cell,* 29:671-679 (1982).

Takahashi et al., Concentrations of Blood Parathyroid Hormone Related Protein (PTHrP) and Various Cytokines in Malignant Tumor Patients, *Record of the Japan Society of Clinical Biochemistry and Metabolism,* 35:107 (1998) (English Abstract).

Tanaka, Triple Paraneoplastic Syndrome of Hypercalcemia, Leukocytosis and Cachexia in Two Human Tumor Xerografts in Nude Mice, *Japanese Journal of Clinical Oncology,* 26:88-94 (1996).

Tempest et al., Reshaping A Human Monoclonal Antibody to Inhibit Human Respiraory Syncytial Virus Infection in vivo, *Bio/Technology,* 9:266-271 (1991).

Tenorio et al., An Immunohistochemical Investigation of the Expression of Parathyroid Hormone Receptors in Rat Cementoblasts, *Archs Oral Biol.,* 41:299-305 (1996).

Tisdale et al., Cancer Cachexia, *International Journal of Pancreatology,* 7:141-150 (1990).

Trowbridge, Interspecies Spleen-Myeloma Hybrid Producing Monoclonal Antibodies Against Mouse Lymphocyte Surface Glycoprotein, T200, *Journal of Experimental Medicine,* 148:313-323 (1978).

Verhoeyen et al., Reshaping Human Antibodies; Grafting an Antilysozyme Activity, *Science,* 239:1534-1536 (1988).

Weissglas et al., Hypercalcemia and Cosecretion of Interleukin-6 and Parathyroid Hormone Related Peptide by a Human Renal Cell Carcinoma Implanted into Nude Mice, *The Journal of Urology,* 153:854-857 (1995).

Wong et al., Modulation of Antibody Affinity by an Engineered Amino Acid Substitution, *J. Immunol.,* 154(7):3351-8 (1995).

Yamamoto et al., Parathyroid Hormone-Related Peptide-(1-34) [PTHrP-(1-34)] Induces Vasopressin Release from the Rat Supraoptic Nucleus in Vitro through a Novel Receptor Distinct from a Type I or Type II PTH/PTHrP Receptor, *Endocrinology,* 138:2066-2072 (1997).

Yelton et al., Fusion of Mouse Myeloma and Spleen Cells, Lymphocyte Hybridomas, Second Workshop on "Functional Properties of Tumors of T and B Lymphocytes," Sponsored by the National Cancer Institute (NIH) 1-7 (1978).

Yoshida et al., Study of Abnormal Calcium Level in Myotonic Dystrophy-Part II: with Respect to Nephrogenous Cylic AMP and Immunoreactivity of Serum Parathyroid Hormone, *The Japanese Endocrine Society Endocrine Journal,* 64(7):539-547 (1988) (English Abstract).

Zylicz et al., Metabolic Response to Enteral Food in Different Phases of Cancer Cachexia in Rats, *Oncology,* 47:87-91 (1990).

\* cited by examiner

AGENTS FOR AMELIORATING LOW VASOPRESSIN LEVEL

TECHNICAL FIELD

The present invention relates to an agent for ameliorating low vasopressin level, which comprises, as an active ingredient, a substance capable of inhibiting the binding between parathyroid hormone-related peptide (PTHrP) and a receptor thereof.

BACKGROUND ART

A living organism has control mechanisms for maintaining various electrolytes in body fluid at their optimum levels, in order to control its body water content. Hormones known to control electrolyte and water metabolisms include aldosterone (mineral corticoid secreted from the adrenal cortex) and vasopressin (posterior pituitary hormone). There are also various diseases known to result from abnormalities of these hormones. Examples of such diseases resulting from hormone abnormalities include hyposupradrenalism (Addison's disease), hyperaldosteronism, posterior pituitary gland hypergasia (diabetes insipidus), and vasopressin secretion abnormality.

On the other hand, the clinical pathology of HHM (humoral hypercalcemia of malignancy) shows a variety of clinical symptoms as presented below (Kanji SATO, "Hypercalcemia Q & A," published by Iyaku Journal Co., Ltd., Japan):

constitutional symptoms including lassitude, systemic malaise, loss of appetite, loss of weight, mouth dryness, and anemia;

digestive symptoms including constipation, peptic ulcer, and acute pancreatitis;

kidney functions including polyposia, polyuria, mouth dryness, and andurinary calculus;

neuromuscular symptoms including weakness, and loss of muscle strength;

psychoneurotic symptoms including retention disorder, loss of thinking ability, clouding of consciousness, and coma; and respiratory symptoms including hypoxemia, and polypnea.

Among these symptoms, polyposia, polyuria, mouth dryness and the like are particularly characteristic clinical symptoms of hypercalcemia.

Parathyroid hormone-related peptide (PTHrP) is known to cause HHM. The mechanism of developing HHM attributable to PTHrP produced by malignant tumors involves the promotion of both bone resorption and calcium reabsorption from the kidneys. Once hypercalcemia is developed, it is known that polyuria, anorexia, nausea or vomiting results in dehydration and an increased blood concentration, thereby leading to further progress of hypercalcemia.

DISCLOSURE OF THE INVENTION

The object of the present invention is to provide an agent for ameliorating low vasopressin level, which comprises, as an active ingredient, a substance capable of inhibiting the binding between PTHrP and a receptor thereof.

Our research efforts were directed to overcoming the above problems, and we have found that a substance capable of inhibiting the binding between PTHrP and a receptor thereof can ameliorate symptoms caused by low vasopressin level and a decrease in vasopressin level, thereby finally completing the invention. That is, the present invention provides an agent for ameliorating low vasopressin level, which comprises, as an active ingredient, a substance capable of inhibiting the binding between PTHrP and a receptor thereof. Examples of such a substance include an antagonist against a PTHrP receptor, an anti-PTHrP antibody (e.g., humanized or chimeric monoclonal antibody), and fragments and/or variants of the antibody. A humanized antibody may be humanized #23-57-137-1 antibody. In addition, low vasopressin level may result from cancer.

Moreover, the present invention provides an agent for ameliorating a symptom caused by a decrease in vasopressin level, which comprises, as an active ingredient, a substance capable of inhibiting the binding between PTHrP and a receptor thereof. A decrease in vasopressin level may result from cancer, and a symptom caused by a decrease in vasopressin level may be at least one symptom selected from the group consisting of polyuria, dehydration, mouth dryness and hyperosmolarity. In addition, because the ameliorating agent of the present invention ameliorates blood hyperosmosis and dehydration, it may also be useful to ameliorate hyperosmolarity or dehydration associated with vomiting, diarrhea, fever, sweating, diabetes insipidus, or diabetes etc.

The present invention relates to an agent for ameliorating low vasopressin level, which comprises, as an active ingredient, a substance capable of inhibiting the binding between PTHrP and a receptor thereof. The term "low vasopressin level" means a state or symptom showing a decreased blood vasopressin level. The present invention also relates to an agent for ameliorating a symptom caused by a decrease in vasopressin level, which comprises, as an active ingredient, a substance capable of inhibiting the binding between PTHrP and a PTHrP receptor.

As used herein, the term "PTHrP receptor" refers to any receptor that can bind to PTHrP (such as those described in Japanese National Phase Laid-open Publication No. 6-506598), regardless of whether or not the PTHrP receptor is present on a target organ (e.g., bone, kidney).

As used herein, the term "a substance capable of inhibiting the binding between PTHrP and a receptor thereof (a PTHrP receptor)" refers to any substance that can bind to PTHrP to prevent the binding of the PTHrP to a PTHrP receptor, such as an anti-PTHrP antibody; any substance that can bind to a PTHrP receptor to prevent the binding of the PTHrP receptor to PTHrP, such as an antagonist against a PTHrP receptor (also referred to as a PTHrP antagonist); or a combination thereof. A specific example of a PTHrP antagonist includes a peptide having replacement or deletion of at least one amino acid residue in the PTHrP peptide or a partial sequence of the PTHrP peptide.

The anti-PTHrP antibody includes those of any known types, such as a humanized antibody, a human antibody (WO 96/33735) or a chimeric antibody (Japanese Patent Application Laid-open No. 4-228089), and an antibody produced from hybridoma #23-57-137-1 (i.e., #23-57-137-1 antibody). The antibody may be of polyclonal type or monoclonal type, but preferably of monoclonal type. The PTHrP antagonist includes, but is not limited to, a polypeptide or a low molecular weight substance. An example of the PTHrP antagonist includes polypeptides having an antagonistic activity against PTHrP as described in Japanese Patent Application Laid-open No. 7-165790; Japanese National Phase Laid-open No. 5-509098; Peptides (UNITED STATES), 1995, 16(6) 1031-1037; and Biochemistry (UNITED STATES) Apr. 281992, 31(16) 4026-4033. These polypeptides may have deletion, replacement, addition or insertion of at least one amino acid residue, as long as they can have an equivalent level of PTHrP antagonistic activity, which are also encompassed in the PTHrP antagonists of the present invention.

This specification includes part or all of the contents as disclosed in the specification and/or drawings of Japanese Patent Application No. 11-189322, which is a priority document of the present application.

In the present invention, as an example of the "substance capable of inhibiting the binding between PTHrP and a PTHrP receptor," an anti-PTHrP antibody will be explained below.

1. Anti-PTHrP Antibody

The anti-PTHrP antibody used in the present invention may be any one as long as it can exhibit a therapeutic effect on low vasopressin level, regardless of its source, type (monoclonal or polyclonal) and configuration.

The anti-PTHrP antibody used in the present invention can be produced by any known method as a polyclonal or monoclonal antibody. Preferably, the anti-PTHrP antibody is a monoclonal antibody derived from a mammal. The mammal-derived monoclonal antibody includes those produced from a hybridoma and those produced by a genetic engineering technique from a host transformed with a recombinant expression vector carrying a gene for the antibody. The antibody can bind to PTHrP to prevent the binding of the PTHrP to a PTH/PTHrP receptor, thus blocking the signal transduction of the PTHrP and consequently inhibiting the biological activity of the PTHrP.

A specific example of such antibody is #23-57-137-1 antibody which can be produced by a hybridoma clone #23-57-137-1.

The hybridoma clone #23-57-137-1 has been designated "mouse-mouse hybridoma #23-57-137-1" and deposited under the terms of the Budapest Treaty on Aug. 15, 1996 at the National Institute of Bioscience and Human-technology, Agency of Industrial Science and Technology, Japan (1-3, Higashi 1-chome, Tsukuba-shi, Ibaraki, Japan) under the accession No. FERM BP-5631.

2. Antibody-Producing Hybridoma

A monoclonal antibody-producing hybridoma can be produced as follows. That is, PTHrP is used as an antigen for immunization in accordance with a conventional immunization method. The resulting immunocytes are fused to known parent cells by a conventional cell fusion method, and monoclonal antibody-producing cells are screened from the fused cells by a conventional screening method.

First, a human PTHrP, which is used as an sensitizing antigen for producing the antibody, is prepared by expressing the PTHrP gene/amino acid sequence disclosed in Suva, L. J. et al., Science (1987) 237, 893. A nucleotide sequence encoding the PTHrP is inserted into a known expression vector, and a suitable host cell is transformed with the expression vector. The PTHrP protein is then isolated and purified from the transformed host cell or from a culture supernatant of the transformed host cell by any known method.

Then, the purified PTHrP protein is used as a sensitizing antigen. Alternatively, a 34-amino acid peptide of the N-terminal region of the PTHrP may be chemically synthesized as the sensitizing antigen.

The mammal to be immunized with the sensitizing antigen is not particularly limited. However, the mammal is preferably selected taking into consideration of compatibility with the parent cell used for cell fusion. Generally, a rodent (e.g., mouse, rat, hamster), rabbit or monkey may be used.

The immunization of the mammal with the sensitizing antigen can be performed in accordance with any known method, for example, by injecting the sensitizing antigen to a mammal intraperitoneally or subcutaneously. More specifically, the sensitizing antigen is properly diluted with or suspended to phosphate-buffered saline (PBS) or physiological saline, the resulting dilution or suspension is then mixed with an appropriate amount of a conventional adjuvant (e.g., Freund's complete adjuvant) to give an emulsion. The emulsion is injected to a mammal several times at intervals of 4 to 21 days. For the immunization, the sensitizing antigen may be attached to a suitable carrier.

After the immunization, the serum antibody level is checked. When the serum antibody level is confirmed to reach a desired level, immunocytes are isolated from the mammal and then subjected to cell fusion. A preferable immunocyte is a spleen cell.

The parent cell used for the cell fusion (i.e., the counterpart of the cell fusion with the immunocyte) is a myeloma cell derived from a mammal. The myeloma cell is of any known cell line, for example, P3 (P3x63Ag8.653) (J. Immunol. (1979) 123, 1548-1550), P3x63Ag8U.1 (Current Topics in Microbiology and Immunology (1978) 81, 1-7), NS-1 (Kohler, G. and Milstein, C. Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S., J. Exp. Med. (1978) 148, 313-323) or R210 (Galfre, G. et al., Nature (1979) 277, 131-133).

Cell fusion of the immunocyte to the myeloma cell is basically performed in accordance with any known method, such as the method of Milstein et al. (Kohler, G. and Milstein, C., Methods Enzymol. (1981) 73, 3-46).

More specifically, the cell fusion is performed, for example, in a conventional nutrient culture medium in the presence of a cell fusion promoter. The cell fusion promoter may be polyethylene glycol (PEG) or a Sendai virus (hemagglutinating virus of Japan; HVJ). If desired, for the purpose of improving the fusion efficiency, an additive such as dimethyl sulfoxide may be incorporated.

The ratio between the immunocytes and the myeloma cells for the cell fusion may be any one. For example, the immunocytes are used in the amount 1-10 times larger than the myeloma cells. The culture medium used for the cell fusion is, for example, RPMI 1640 medium or MEM medium suitable for the growth of the above-mentioned myeloma cell lines, or other medium conventionally used for the culture of such cell lines. If desired, a serum supplement, such as feral calf serum (FCS), may be added to the culture medium.

The cell fusion is performed by fully mixing given amounts of the immunocytes and the myeloma cells in the culture medium, adding a PEG solution (e.g., mean molecular weight: about 1000-6000) (which has been previously warmed to about 37° C.) to the mixture usually to a concentration of 30-60% (w/v), and then mixing the resulting solution, thereby producing the desired fused cells (i.e., hybridomas). Subsequently, an appropriate culture medium is added to the culture solution successively, and centrifuged to remove the supernatant. This procedure is repeated several times to remove the cell fusion promoter or the like that are undesirable for the growth of the hybridomas, from the culture medium.

The obtained hybridomas can be selected by culturing in a conventional selective medium, such as hypoxanthine-aminopterin-thymidine (HAT) medium. The culturing of the hybridomas in HAT medium is performed for the time of period enough to cause the death of the cells other than the desired hybridomas (i.e., cells that fail to fuse), usually for several days to several weeks. Subsequently, conventional limiting dilution method is performed for screening and mono-cloning of the hybridomas that are secreting the desired antibody.

As a method other than preparing the hybridomas by immunizing a non-human mammal with the antigen as described above, a human lymphocyte may be sensitized with PTHrP in vitro, and then subjected to cell fusion with a human-derived myeloma cell capable of infinite growth, thereby producing the desired human antibody having a binding activity against the PTHrP (Japanese Patent Publication No. 1-59878). Alternatively, a human antibody against PTHrP may be prepared by injecting PTHrP as an antigen to a transgenic animal that has the entire repertories of human antibody genes to produce an anti-PTHrP antibody-producing cell, and then immortalizing the cells, thus producing the human antibody from the immortalized cell (see International Patent Publication Nos. WO 94/25585, WO 93/12227, WO 92/03918 and WO 94/02602).

The monoclonal antibody-producing hybridoma prepared as above can be subcultured in a conventional culture medium and stored under liquid nitrogen for a long time of period.

For the production of a monoclonal antibody from the hybridoma, a method may be employed that involves culturing the hybridoma in accordance with a conventional technique and collecting the monoclonal antibody from the culture supernatant, or that involves injecting the hybridoma to a mammal compatible with the hybridoma to grow the hybridoma in the mammal and collecting the hybridoma from the ascites of the mammal. The former method is suitable for producing the antibody in high purity, while the latter method is suitable for producing the antibody in a large amount.

3. Recombinant Antibody

In the present invention, a recombinant-type monoclonal antibody may be used, which can be produced by cloning an antibody gene from the hybridoma, integrating the antibody gene into a suitable vector, introducing the vector into a host, and then producing the antibody from the host according to a conventional genetic recombination technique (see, for example, Vandamme, A. M. et al., Eur. J. Biochem. (1990) 192, 767-775, 1990)

Specifically, mRNA encoding variable (V) region of an anti-PTHrP antibody is isolated from the anti-PTHrP antibody-producing hybridoma. The isolation of the mRNA is performed by preparing a total RNA by any known method, such as guanidium ultracentrifugation method (Chirgwin, J. M. et al., Biochemistry (1979) 18, 5294-5299) and AGPC method (Chomczynski, P. et al., Anal. Biochem. (1987) 162, 156-159), and then producing the desired mRNA from the total RNA using mRNA Purification Kit (Pharmacia) or the like. Alternatively, the mRNA may also be prepared directly using QuickPrep mRNA Purification Kit (Pharmacia).

Next, cDNA for the antibody V-region is synthesized from the mRNA with a reverse transcriptase. The synthesis of the cDNA is performed using AMV Reverse Transcriptase First-strand cDNA Synthesis Kit (Seikagaku Corporation) or the like. The cDNA may also be synthesized and amplified by 5'-RACE method (Frohnman, M. A. et al., Proc. Natl. Acad. Sci. USA (1988) 85, 8998-9002; Belyavsky, A. et al., Nucleic Acids Res. (1989) 17, 2919-2932) using 5'-Ampli FINDER RACE Kit (CLONETECH) in combination with PCR method, or the like.

A DNA fragment is isolated and purified from the resulting PCR product and then ligated to a vector DNA to obtain a recombinant vector. The recombinant vector is introduced into a host such as E. coli, and a colony containing a desired recombinant vector is selected. The nucleotide sequence of the DNA in the recombinant vector is confirmed by, for example, dideoxynucleotide chain termination method.

Once DNA encoding the anti-PTHrP antibody V-region is obtained, the DNA is integrated into an expression vector containing a DNA encoding a desired antibody constant (C) region.

For the production of the anti-PTHrP antibody used in the present invention, the antibody gene is integrated into an expression vector so that the antibody gene can be expressed under the control of expression control regions (e.g., enhancer, promoter). A host cell is transformed with the expression vector to express the antibody.

In the expression of the antibody gene, a DNA encoding heavy (H) chain and a DNA encoding light (L) chain of the antibody may be integrated into separate expression vectors, and then a host cell is co-transformed with the resulting expression vectors. Alternatively, both the DNA encoding H-chain and the DNA encoding L-chain of the antibody may be integrated together into a single expression vector, and then a host cell may be transformed with the resulting recombinant expression vector (see WO 94/11523).

For the production of the recombinant antibody, besides the above-mentioned host cells, a transgenic animal may also be used as a host. For example, the antibody gene is inserted into a predetermined site of a gene encoding a protein inherently produced in the milk of an animal (e.g., goat β-casein) to obtain a fusion gene. A DNA fragment containing the antibody gene-introduced fusion gene is injected into an embryo of a goat, and the embryo is then introduced into a female goat. The female goat having the embryo therein bears a transgenic goat. The antibody of interest is secreted in the milk from the transgenic goat or a progeny thereof. For the purpose of increasing the amount of the antibody-containing milk from the transgenic goat, an appropriate hormone may be administered to the transgenic goat (Ebert, K. M. et al., Bio/Technology (1994) 12, 699-702).

4. Modified Antibody

In the present invention, for the purpose of reducing the heterogenisity against a human body or the like, an artificially modified recombinant antibody may also be used, such as a chimeric antibody and a humanized antibody. These modified antibodies can be prepared by the following known methods.

A chimeric antibody usable in the present invention can be prepared by ligating the DNA encoding the antibody V-region prepared as set forth above to a DNA encoding a human antibody C-region, integrating the ligation product into an expression vector, and introducing the resulting recombinant expression vector into a host to produce the chimeric antibody.

A humanized antibody is also referred to as a "reshaped human antibody," in which the complementarity determining regions (CDRs) of an antibody of a non-human mammal (e.g., a mouse) are grafted to those of a human antibody. The general genetic recombination procedures for producing such humanized antibody are also known (see EP 125023; WO 96/02576).

Specifically, a DNA sequence in which mouse antibody CDRs are ligated through framework regions (FRs) of a human antibody is amplified by PCR method using several oligonucleotides as primers which have been designed to have regions overlapping to the terminal regions of the CDRs and the FRs. The resulting DNA is ligated to a DNA encoding a human antibody C-region, and the ligation product is integrated into an expression vector. The resulting recombinant expression vector is introduced into a host, thereby producing the humanized antibody (see EP 239044, WO 96/02576).

The FRs of the human antibody ligated through the CDRs are selected so that the CDRs can form a suitable antigen binding site. If necessary, an amino acid(s) in the FRs of the antibody V-region may be replaced so that the CDRs of the reshaped human antibody can form a suitable antigen binding site (Sato, K. et al., Cancer Res. (1993) 53, 851-856).

The C-region of the chimeric or humanized antibody may be any human antibody C-region, such as Cγ1, Cγ2, Cγ3 or Cγ4 for the H-chain, and Cκ or Cλ for the L-chain. The human antibody C-region may be modified for the purpose of improving the stable production of the antibody.

The chimeric antibody is composed of V-regions derived from a non-human mammalian antibody and C-regions derived from a human antibody. The humanized antibody is composed of CDRs derived from a non-human mammalian antibody and FRs and C-regions derived from a human antibody. The humanized antibody is useful as an active ingredient for the ameliorating agent of the present invention, because the antigenicity of the antibody against a human body is reduced.

A specific example of the humanized antibody usable in the present invention is humanized #23-57-137-1 antibody; in which the CDRs are derived from mouse-derived #23-57-137-1 antibody; the L-chain is composed of the CDRs ligated through three FRs (FR1, FR2 and FR3) derived from human antibody HSU 03868 (GEN-BANK, Deftos, M. et al., Scand. J. Immunol., 39, 95-103, 1994) and a FR (FR4) derived from human antibody S25755 (NBRF-PDB); and the H-chain is composed of the CDRs ligated through FRs derived from human antibody S31679 (NBRF-PDB, Cuisinier, A. M. et al., Eur. J. Immunol. 23, 110-118, 1993) in which a part of the amino acid residues in the FRs is replaced so that the reshaped humanized antibody can exhibit an antigen-binding activity.

The *E. coli* strains containing the plasmids having DNAs encoding the H-chain and the L-chain of the humanized #23-57-137-1 antibody, respectively, are designated *Escherichia coli* JM109 (hMBC1HcDNA/pUC19) (for H-chain) and *Escherichia coli* JM109 (hMBC1Lqλ/pUC19) (for L-chain), respectively. These strains have been deposited under the terms of the Budapest Treaty on Aug. 15, 1996 at the National Institute of Bioscience and Human-technology, Agency of Industrial Science and Technology, Japan (1-3, Higashi 1-chome, Tsukuba-shi, Ibaraki, Japan), under the accession No. FERM BP-5629 for *Escherichia coli* JM109 (hMBC/HcDNA/pUC19), and under the accession No. FERM BP-5630 for *Escherichia coli* JM109 (hMBC1Lqλ/pUC19).

5. Antibody Variants

The antibody used in the present invention may be a fragment thereof or a modified form of the fragment, as long as it can bind to PTHrP and inhibit the activity of the PTHrP. For example, the fragment of the antibody includes Fab, F(ab')$_2$, Fv, or a single chain Fv (scFv) composed of a H-chain Fv fragment and a L-chain Fv fragment linked together through a suitable linker. Specifically, such antibody fragments can be produced by cleaving the antibody with an enzyme (e.g., papain, pepsin) into antibody fragments, or by constructing a gene encoding the antibody fragment and inserting the gene into an expression vector and introducing the resulting recombinant expression vector into a suitable host cell, thereby expressing the antibody fragment (see, for example, Co, M. S., et al., J. Immunol. (1994), 152, 2968-2976; Better, M. & Horwitz, A. H., Methods in Enzymology (1989), 178, 476-496, Academic Press, Inc.; Plueckthun, A. & Skerra, A., Methods in Enzymology (1989) 178, 476-496, Academic Press, Inc.; Lamoyi, E., Methods in Enzymology (1989) 121, 652-663; Rousseaux, J. et al., Methods in Enzymology (1989) 121, 663-669; and Bird, R. E. et al., TIBTECH (1991) 9, 132-137).

A scFv can be produced by linking the H-chain V-region to the L-chain V-region through a linker, preferably a peptide linker (Huston, J. S. et al., Proc. Natl. Acad. Sci. USA (1988) 85, 5879-5883). The H-chain V-region and the L-chain V-region in the scFv may be derived from any one of the antibodies described herein. The peptide linker which binds the V-regions may be any single chain peptide, for example, of 12-19 amino acid residues.

The DNA encoding the scFv can be prepared by first amplifying a DNA encoding the H-chain V-region and a DNA encoding the L-chain V-region of the antibody separately using a DNA fragment encoding the entire region or a part of the H-chain that includes the V-region and a DNA fragment encoding the entire region or a part of the L-chain that includes the V-region as templates and primer pairs that define the terminal ends of the DNA fragments; and then amplifying a DNA encoding the peptide linker using a DNA fragment encoding the peptide linker as a template and a primer pair that define the terminal ends of the DNA fragment so that each terminal end of the peptide linker is ligated to the H-chain V-region and the L-chain V-region, respectively.

Once the DNA encoding the scFv is prepared, an expression vector carrying the DNA and a host transformed with the expression vector can be prepared by conventional methods. The scfv can be produced from the transformed host by a conventional method.

The fragments of the antibody may be produced by preparing genes for the fragments and expressing the genes in suitable hosts as described above. The antibody fragments is also encompassed in the "antibody" of the present invention.

As a modified form of the above-mentioned antibodies, for example, anti-PTHrP antibody conjugated to any molecule (e.g., polyethylene glycol; PEG) may also be used. Such modified antibodies are also encompassed in the "antibody" of the present invention. The modified antibodies can be prepared by chemical modifications of the antibodies. The chemical modification techniques suitable for this purpose have already been established in the art.

6. Expression and Production of Recombinant Antibody or Modified Antibody

The antibody gene constructed as described above can be expressed and produced by known methods. For the expression in a mammalian cell, a conventional useful promoter, the antibody gene to be expressed and a poly(A) signal (located downstream to the 3' end of the antibody gene) are operably linked. For example, as the useful promoter/enhancer system, a human cytomegalovirus immediate early promoter/enhancer system may be used.

Other promoter/enhancer systems usable in the expression of the antibody used in the present invention include those derived from viruses (e.g., retrovirus, polyoma virus, adenovirus and simian virus 40 (SV40)) and those derived from mammalian cells (e.g., human elongation factor 1α (HEF1α).

When SV40 promoter/enhancer system is used, the gene expression may be performed readily by the method of Mulligan et al. (Nature (1979) 277, 108). When HEF1α promoter/enhancer system is used, the gene expression may be performed readily by the method of Mizushima et al. (Nucleic Acids Res. (1990) 18, 5322).

For the expression in *E. coli*, a conventional useful promoter, a signal sequence for secreting the antibody of interest and the antibody gene to be expressed may be operably linked. As such a promoter, lacZ promoter or araB promoter may be used. When lacZ promoter is used, the gene expression may be performed by the method of Ward et al. (Nature (1098) 341, 544-546; FASBE J. (1992) 6, 2422-2427). When araB promoter is used, the gene expression may be performed by the method of Better et al. (Science (1988) 240, 1041-1043).

Regarding the signal sequence for secretion of the antibody, when the antibody of interest is intended to be secreted in a periplasmic space of the *E. Coli*, pelB signal sequence (Lei, S. P. et al., J. Bacteriol. (1987) 169, 4379) may be used. The antibody secreted into the periplasmic space is isolated and then refolded so that the antibody takes an appropriate configuration for use.

Regarding the replication origin, those derived from viruses (e.g., SV40, polyoma virus, adenovirus, bovine papilloma virus (BPV)) or the like may be used. In order to increase the gene copy number in the host cell system, the expression vector may further contain a selective marker gene, such as an aminoglycoside phosphotranferase (APH) gene, a thymidine kinase (TK) gene, an *E. coli* xanthine-guanine phosphoribosyltransferase (Ecogpt) gene and a dihydrofolate reductase (dhfr) gene.

For the production of the antibody used in the present invention, any expression system such as eukaryotic and prokaryotic cell systems may be used. The eukaryotic cell includes established cell lines of animals (e.g., mammals, insects, molds and fungi, yeast). The prokaryotic cell includes bacterial cells such as *E. coli* cells.

It is preferable that the antibody used in the present invention be expressed in a mammalian cell, such as a CHO, COS, myeloma, BHK, Vero or HeLa cell.

Next, the transformed host cell is cultured in vitro or in vivo to produce the antibody of interest. The culturing of the host cell may be performed by any known method. The culture medium usable herein may be DMEM, MEM, RPMI 1640 or IMDM medium. The culture medium may contain a serum supplement, such as fetal calf serum (FCS).

7. Isolation and Purification of Antibody

The antibody expressed and produced as described above may be isolated from the cells or the host animal body and purified to uniformity. The isolation and purification of the antibody used in the present invention may be performed on an affinity column. Examples of a protein A column include Hyper D, POROS and Sepharose F.F. (Pharmacia). The method is not particularly limited and other methods conventionally used for the isolation and purification of an antibody may also be employed. For example, various chromatographs using columns other than the above-mentioned affinity column, filtration, ultrafiltration, salting out and dialysis may be used singly or in combination to isolate and purify the antibody of interest (Antibodies A Laboratory Manual. Ed. Harlow, David Lane, Cold Spring Harbor Laboratory, 1988).

8. Determination of the Activities of the Antibody

The determination of the antigen-binding activity (Antibodies A Laboratory Manual, Ed. Harlow, David Lane, Cold Spring Harbor Laboratory, 1988) or the inhibitory activity against a ligand receptor (Harada, A. et al., International Immunology (1993) 5, 681-690) of the antibody used in the present invention may be performed by any known methods. The method for the determination of the antigen-binding activity of the anti-PTHrP antibody used in the present invention may be ELISA (enzyme-linked immunosorbent assay), EIA (enzyme immunoassay), RIA (radioimmunoassay) or a fluorescent antibody. For example, when enzyme immunoassay is employed, a sample solution containing the anti-PTHrP antibody (e.g., a culture supernatant of anti-PTHrP antibody-producing cells, or the anti-PTHrP antibody in a purified form) is added to a plate on which PTHrP (1-34) is previously coated. A secondary antibody labeled with an enzyme (e.g., alkaline phosphatase) is further added to the plate. The plate is incubated and washed. A substrate for the enzyme (e.g., p-nitrophenylphosphoric acid) is added to the plate, and the absorbance of the solution in the plate is measured to evaluate the antigen-binding activity of the antibody.

To confirm the activity of the antibody used in the present invention, a neutralizing activity of the antibody (e.g., anti-PTHrP antibody) may be determined.

9. Routes for Administration and Pharmaceutical Preparations

The ameliorating agent of the present invention is used for treatment or amelioration of a state or symptom showing a decreased vasopressin level (low vasopressin level). Low vasopressin level may be induced by cancer or other factors. An example of the cancer-induced type is hypercalcemia of malignancy.

In addition, the ameliorating agent of the present invention may be administered in order to ameliorate a symptom cased by a decrease in vasopressin level. In the present invention, a decrease in vasopressin level may result from any cause, but preferably from cancer. Examples of symptoms caused by a decrease in vasopressin level include, but are not limited to, polyuria, dehydration, and mouth dryness. The ameliorating agent of the present invention can be administered for any one of these symptoms or combinations thereof.

The ameliorating agent comprising the anti-PTHrP antibody as an active ingredient according to the present invention may be administered orally or parenterally, preferably parenterally. The ameliorating agent may take any dosage form, such as a transpulmonary agent (e.g., an agent administered with the help of a device such as a nebulizer), a nasogastric agent, a transdermic agent (e.g., ointment, cream) or an injection. Examples of the injection include an intravenous injection (e.g., drops), an intramuscular injection, an intraperitoneal injection and a subcutaneous injection for systemic or topical administration. The route of administration may be properly selected depending on the age of a patient and the conditions of diseases. An effective single dose may be selected within the range from 0.001 to 1,000 mg per kg of the body weight. Alternatively, the dose to a patient may be selected within the range from 0.01 to 100,000 mg/body, preferably 0.1 to 10,000 mg/body, more preferably 0.5 to 1,000 mg/body, and even more preferably 1 to 100 mg/body. However, the dose of the ameliorating agent comprising the anti-PTHrP antibody of the present invention is not particularly limited to these ranges.

The ameliorating agent may be administered to a patient at any stage, including before or after the development of low vasopressin level. The ameliorating agent may also be administered at the stage where the development of weight loss is predicted in the patient.

The ameliorating agent comprising the anti-PTHrP antibody as an active ingredient of the present invention may be formulated by any conventional method (Remington's Pharmaceutical Science, latest edition, Mark Publishing Company, Easton, USA). The preparation may further comprise pharmaceutically acceptable carriers and additives.

Examples of such carriers and additives include water, pharmaceutically acceptable organic solvents, collagen, polyvinyl alcohol, polyvinyl pyrrolidone, carboxyvinyl polymer, sodium carboxymethyl cellulose, poly(sodium acrylate), sodium arginate, water soluble dextran, sodium carboxymethyl starch, pectin, methyl cellulose, ethyl cellulose, xanthane gum, gum arabic, casein, agar, polyethylene glycol, diglycerin, glycerin, propylene glycol, vaseline, paraffin, stearyl alcohol, stearic acid, human serum albumin (HSA), mannitol, sorbitol, lactose, and surfactants acceptable as pharmaceutical additives.

In the practical use, the additive is properly selected from the above members either singly or in combination depending on (without limitation) the dosage form employed. For example, for use as an injectable form, the anti-PTHrP antibody of the purified form is dissolved in a solvent (e.g., physiological saline, a buffer, a grape sugar solution) and then an adsorption-preventing agent (e.g., Tween 80, Tween 20, a gelatin, human serum albumin) is added thereto. The ameliorating agent of the present invention may also be in a reconstitutable freeze-dried form, which is dissolved before use. For the formulation of the freeze-dried dosage form, an excipient such as a sugar alcohol (e.g., mannitol, grape sugar) or a sugar may be incorporated.

BEST MODE FOR CARRYING OUT THE INVENTION

Figure 1:
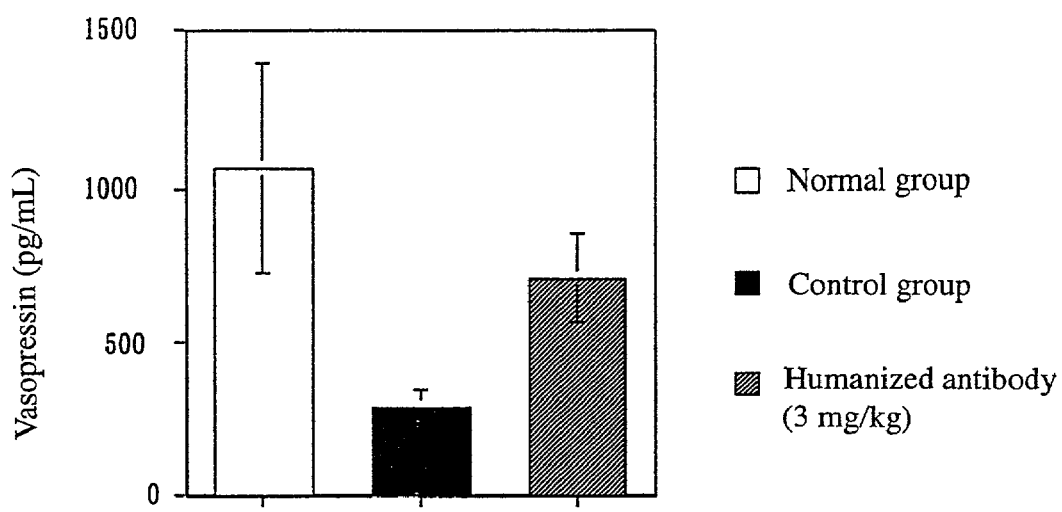
FIG. 1 is a graph showing the results of a pharmacological test of a humanized anti-PTHrP antibody for blood vasopressin level in a hypercalcemia model rat.

Hereinbelow, the present invention will be described in greater decaudal with reference to the following Reference Examples and Examples, which should not be construed as limiting the technical scope of the invention.

EXAMPLE 1

Pharmacological Test in Model Animals with Hypercalcemia (1)

(1) Objective of the test

Using a hypercalcemia model animal (human tumor implanted nude rat model), a humanized monoclonal antibody against PTHrP was examined for its effects on blood vasopressin level and urine volume.

(2) Method

As a model animal, a nude rat implanted with human large cell lung carcinoma LC-6 [purchased from the Central Institute for Experimental Animals] was used. It is known that a nude rat implanted with human large cell lung carcinoma LC-6 shows an increased blood calcium level as increasing the tumor volume and develops weight loss and so on. In this example, this hypercalcemia model animal was used to examine blood vasopressin level by comparison with a normal rat, and to evaluate effects of the humanized monoclonal antibody on blood vasopressin level. This model animal was also used to examine urine volume and to evaluate effects of the humanized monoclonal antibody on urine volume.

The hypercalcemia model animals were produced and divided into groups in the following manner. The human large cell lung carcinoma LC-6 transplanted in vivo using a BALB/c-nu/nu nude mouse (CLEA Japan, Inc.) was removed, and then finely cut into 3-mm cube of blocks. The resulting tumor blocks were subcutaneously implanted into each of the rats at the lateral region at a ratio of one piece per rat. As rats, 5-weeks-old male F344/N Jcl-rnu nude rats (CLEA Japan, Inc.) were purchased and acclimatized for 1 week. The resulting 6-weeks-old rats were implanted with the tumor. About a month and a half after the implantation, the rats with increased blood calcium levels and reduced body weights were used as hypercalcemia model animals for pharmacological test. These rats were divided into groups so that blood calcium levels and body weights of the rats in the individual groups were averaged.

In the determination of vasopressin levels, the humanized monoclonal antibody against PTHrP was administered to each of a group of the hypercalcemia model animals thus prepared via the tail vein once a week at a dose level of 3 mg/kg (i.e., administered on days 0, 7, 14, 21, 28 and 35). On the other hand, alendronate, which has been used as a therapeutic agent for hypercalcemia, was administered to each of another group of the hypercalcemia model animals via the caudal vein twice a week at a dose level of 2.5 mg/kg (i.e., administered on days 0, 3, 7, 10, 14, 17, 21, 24, 28, 31, 35 and 38). As a control, phosphate buffered saline (PBS) was administered to each of still another group of the hypercalcemia model animals via the tail vein on days 0, 7, 14, 21, 28 and 35. The animals which clearly failed to maintain the implanted tumor during the test were removed from data analysis.

On day 42 after starting the administration of the above drugs (antibody, alendronate, PBS), blood was collected from the descending aorta and treated with EDTA to separate plasma for the determination of blood vasopressin levels. Because the animals which clearly failed to maintain the implanted tumor were removed from data analysis at the time of blood collection, data analysis was performed on 12 rats in the humanized monoclonal anti-PTHrP antibody-administered group, 3 rats in the alendronate-administered group, 8 rats in the PBS-administered group, and 5 rats in the normal group. The determination of blood vasopressin levels was performed by RIA method using plasma.

To determine urine volume, in each of the test groups of the hypercalcemia model animals prepared as set forth above, either 3 mg/kg of the humanized monoclonal anti-PTHrP antibody or 5 mg/kg of alendronate was administered to each model animal via the tail vein. In the control group, PBS was administered to each model animal via the tail vein. After the administration, urine was collected for 24 hours from the morning of day 13 to the morning of day 14, and assayed for its weight and specific gravity to calculate urine volume.

(3) Results

Figure 2:
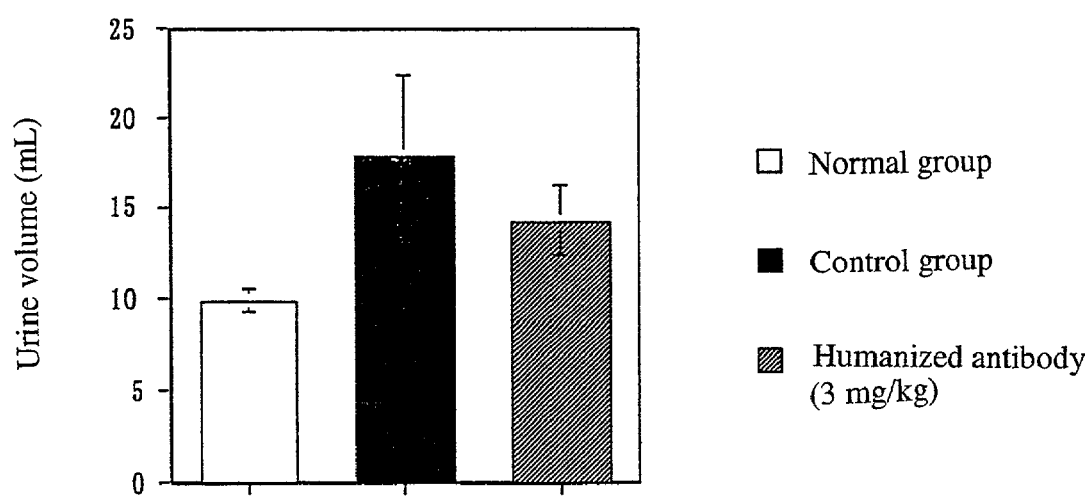
FIG. 2 is a graph showing the results of a pharmacological test of a humanized anti-PTHrP antibody for urine volume in a hypercalcemia model rat.

The hypercalcemia model animals were shown to have decreased blood vasopressin levels. The humanized monoclonal antibody could ameliorate decreased blood vasopressin levels in these hypercalcemia model animals (FIG. 1). In addition, the humanized monoclonal antibody was observed to ameliorate a symptom of polyuria in the hypercalcemia model animals (FIG. 2).

EXAMPLE 2

Pharmacological Test in Model Animals with Hypercalcemia (2)

(1) Objective of the Test

Using a hypercalcemia model animal (a human tumor-transplanted nude mouse), a humanized monoclonal antibody against PTHrP was examined for its effects on blood vasopressin level and serum osmotic pressure.

(2) Method

As a model animal, a nude rat implanted with human large cell lung carcinoma LC-6 [purchased from the Central Institute for Experimental Animals] was used. It is known that a nude rat implanted with human large cell lung carcinoma LC-6 shows an increased blood calcium level as increasing the tumor volume and develops weight loss and so on. In this example, this hypercalcemia model animal was used to examine blood vasopressin level by comparison with a normal rat, and to evaluate effects of the humanized monoclonal antibody on blood vasopressin level. This model animal was also used to examine serum osmotic pressure and to evaluate effects of the humanized monoclonal antibody on serum osmotic pressure.

The hypercalcemia model animals were produced and divided into groups in the following manner. The human large cell lung carcinoma LC-6 subcultured in vivo using a BALB/c-nu/nu nude mouse (CLEA Japan, Inc.) was removed, and then finely cut into 3-mm cube of blocks. The resulting tumor blocks were subcutaneously implanted into each of the rats at the lateral region at a ratio of one piece per rat. As rats, 4-weeks-old male F344/N Jcl-rnu nude rats (CLEA Japan, Inc.) were purchased and acclimatized for 10 days. The resulting 6-weeks-old rats were implanted with the tumor. About a month and a half after the implantation, the rats with increased blood calcium levels and reduced body weights were used as hypercalcemia model animals for pharmacological test. These rats were divided into groups so that blood calcium levels and body weights of the rats in the individual groups were averaged.

The humanized monoclonal antibody against PTHrP was administered to each of a group of the hypercalcemia model animals thus prepared via the caudal vein, once a week, at a dose level of 0.11, 0.33, 1 or 3 mg/kg (i.e., administered on days 0, 7, 14, 21, 28 and 35). As a control, phosphate buffered saline (PBS) was administered to each of another group of the hypercalcemia model animals via the caudal vein on days 0, 7, 14, 21, 28 and 35. The animals which clearly failed to maintain the implanted tumor during the test were removed from data analysis. Data analysis was performed on 7, 8, 8 and 6 rats in the groups administered with the humanized monoclonal anti-PTHrP antibody at a dose level of 0.11, 0.33, 1 and 3 mg/kg, respectively, 8 rats in the PBS-administered group, and 7 rats in the normal group.

On day 42 after the administration of the above antibody, blood was collected from the descending aorta, followed by separation of plasma and serum in an EDTA-containing tube and a Separapid tube, respectively. The determination of blood vasopressin levels was performed by RIA method using plasma. The determination of blood osmotic pressure was performed by cryoscopy using serum.

(3) Results

Figure 3:
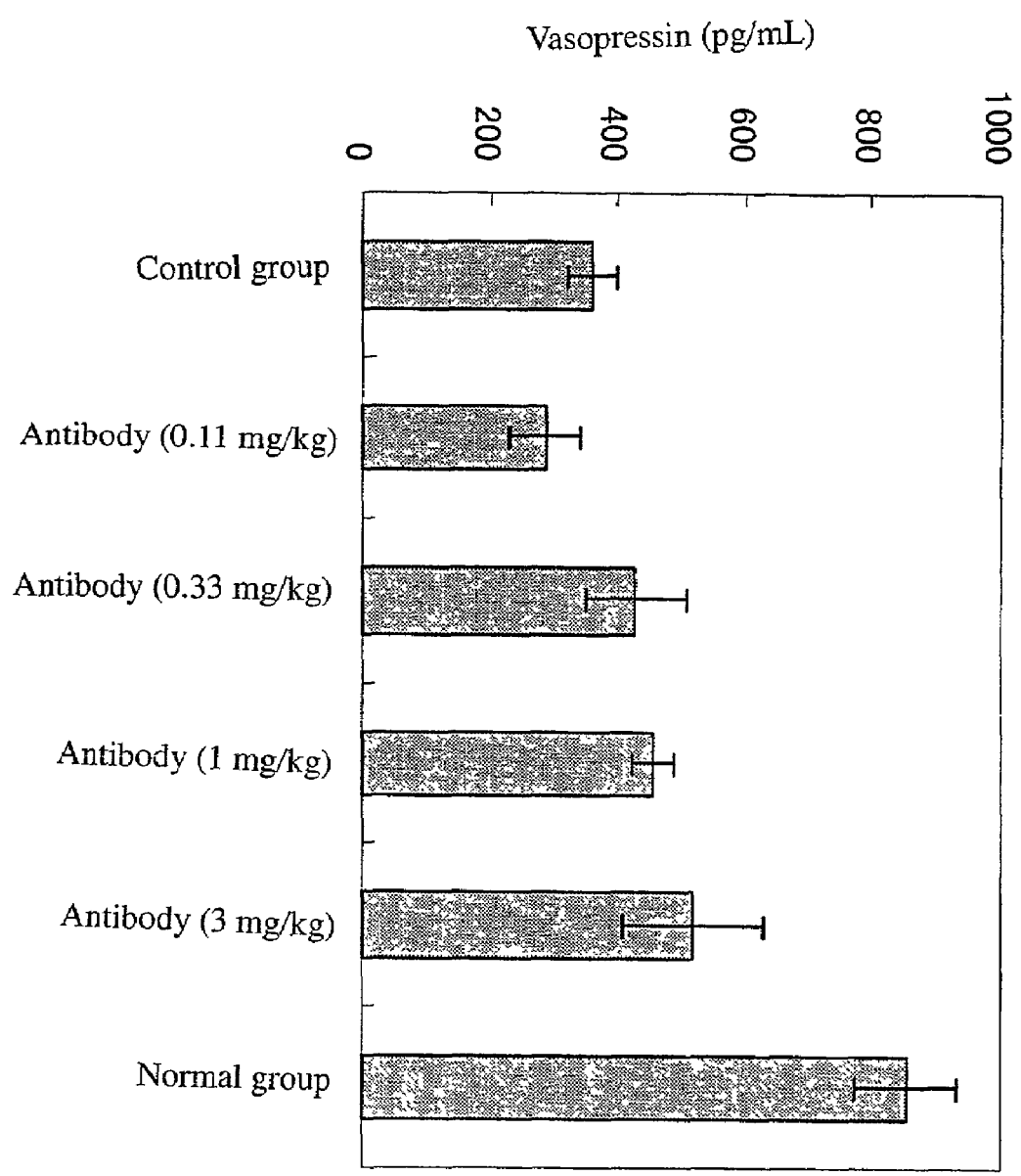
FIG. 3 is a graph showing the results of a pharmacological test of a humanized anti-PTHrP antibody for blood vasopressin level in a hypercalcemia model rat.
Figure 4:
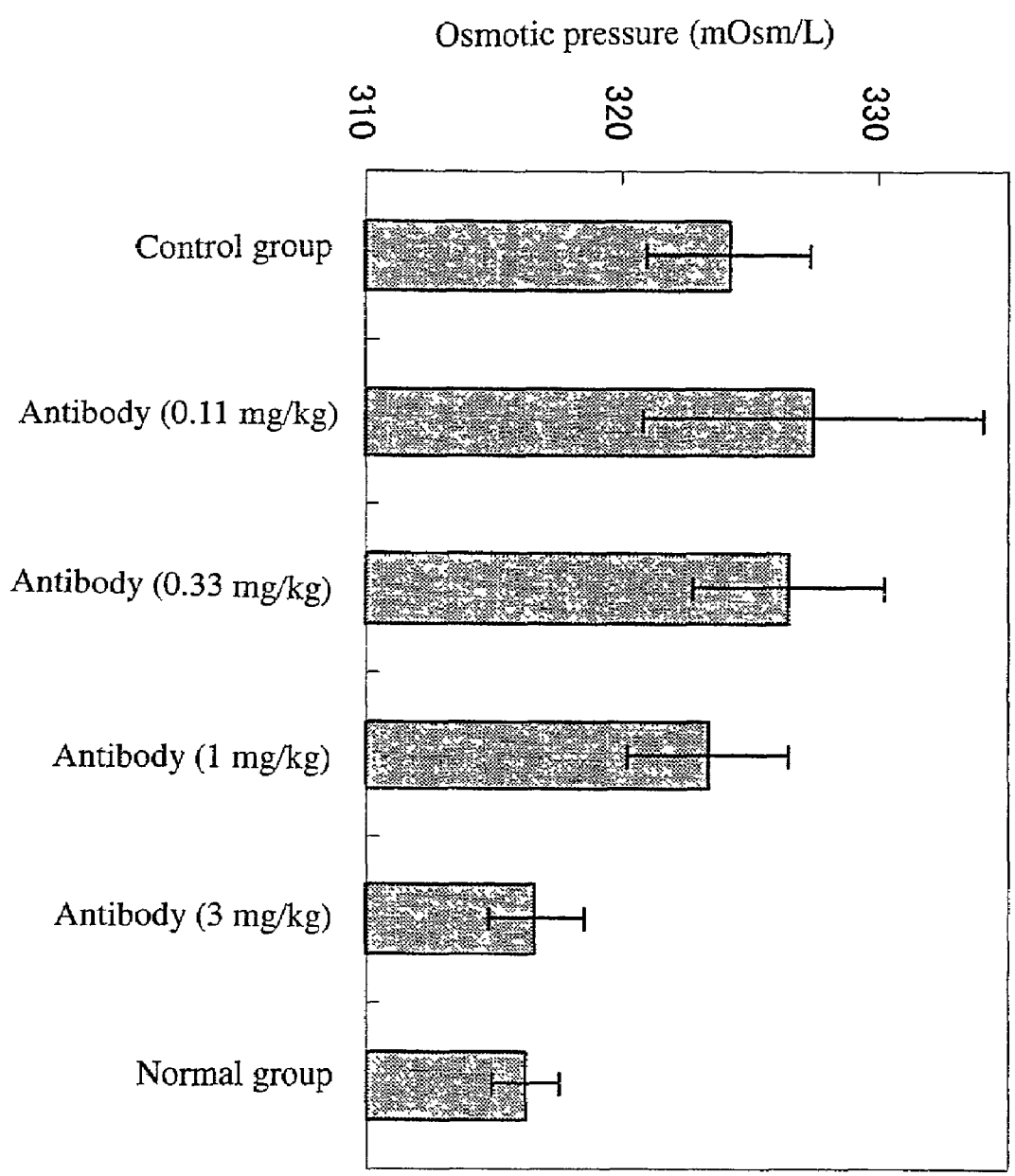
FIG. 4 is a graph showing the results of a pharmacological test of a humanized anti-PTHrP antibody for serum osmotic pressure in a hypercalcemia model rat.

The hypercalcemia model animals were shown to have decreased blood vasopressin levels. The humanized monoclonal antibody could dose-dependently ameliorate decreased blood vasopressin levels in these hypercalcemia model animals (FIG. 3). In addition, the humanized monoclonal antibody was observed to dose-dependently ameliorate increased blood osmotic pressures in the hypercalcemia model animals (FIG. 4).

Reference Example 1

Preparation of Hybridomas Producing Anti-PTHrP (1-34) Mouse Monoclonal Antibody

Hybridomas capable of producing a monoclonal antibody against human PTHrP (1-34), #23-57-154 and #23-57-137-1, were prepared as follows (see Sato, K. et al., J. Bone Miner. Res. 8, 849-860, 1993). The amino acid sequence of the human PTHrP (1-34) is shown in SEQ ID NO:75.

For use as an immunogen, PTHrP (1-34) (Peninsula) was conjugated with a carrier protein thyroglobulin using carbodiimide (Dojinn). The thycloglobulin-conjugated PTHrP (1-34) was dialyzed to obtain a solution having a protein concentration of 2 mg/ml. The resulting solution was mixed with Freund's adjuvant (Difco) at a mixing ratio of 1:1 to give an emulsion. This emulsion was injected to 16 female BALB/C mice 11 times subcutaneously at the back or intraperitoneally at a dose level of 100 μg/mouse for each injection, thereby immunizing the mice. For the priming immunization, Freund's complete adjuvant was used; while for the boosting immunization, Freund's incomplete adjuvant was used.

Each of the immunized mice was determined for its antibody titer in the serum in the following manner. That is, each of the mice was blood-drawn via its caudal vein, and the anti-serum is separated from the blood. The anti-serum was diluted with a RIA buffer and mixed with $^{125}$I-labeled PTHrP (1-34) to determine the binding activity. The mice that were confirmed to have a sufficiently increased titer were injected with PTHrP (1-34) without a carrier protein intraperitoneally at a dose level of 50 μg/mouse for the final immunization.

Three days after the final immunization, the mouse is sacrificed and the spleen was removed therefrom. The spleen cells were subjected to cell fusion with mouse myeloma cell line P3x63Ag8U.1 in accordance with a conventional known method using 50% polyethylene glycol 4000. The fused cells thus prepared were seeded to each well of eighty-five 96-well plates at a density of $2\times10^4$/well. Hybridomas were screened in HAT medium as follows.

The screening of hybridomas was performed by determining the presence of PTHrP-recognition antibodies in the culture supernatant of the wells in which cell growth had been observed in HAT medium, by solid phase RIA method. The hybridomas were collected from the wells in which the binding ability to the PTHrP-recognition antibodies had been confirmed. The hybridomas thus obtained was suspended into RPMI-1640 medium containing 15% FCS supplemented with OPI-supplement (Sigma), followed by unification of the hybridomas by limiting dilution method. Thus, two types of hybridoma clones, #23-57-154 and #23-57-137-1, could be obtained, both which had a high binding ability to PTHrP (1-34).

Hybridoma clone #23-57-137-1 was designated "mouse-mouse hybridoma #23-57-137-1," and has been deposited under the terms of the Budapest Treaty on Aug. 15, 1996 at the National Institute of Bioscience and Human-technology, Agency of Industrial Science and Technology, Japan (1-3, Higashi 1-chome, Tsukuba-shi, Ibaraki, Japan) under the accession No. FERM BP-5631.

Reference Example 2

Cloning of DNAs Encoding V-Regions of Mouse Monoclonal Antibody Against Human PTHrP (1-34)

Cloning of DNAs encoding the V-regions of a mouse monoclonal antibody against human PTHrP (1-34), #23-57-137-1, was performed in the following manner.

(1) Preparation of mRNA mRNA from hybridoma #23-57-137-1 was prepared using Quick Prep mRNA Purification Kit (Pharmacia Biotech). That is, cells of hybridoma #23-57-137-1 were fully homogenized with an extraction buffer, and mRNA was isolated and purified therefrom on an oligo(dT)-Cellulose Spun Column in accordance with the instructions included in the kit. The resulting solution was subjected to ethanol precipitation to obtain the mRNA as a precipitate. The mRNA precipitate was dissolved in an elution buffer.

(2) Production and Amplification of cDNA for Gene Encoding Mouse H-Chain V-Region (i) Cloning of cDNA for #23-57-137-1 Antibody H-Chain V-Region A gene encoding H-chain V-region of the mouse monoclonal antibody against human PTHrP was cloned by 5'-RACE method (Frohman, M. A. et al., Proc. Natl. Acad. Sci. USA, 85, 8998-9002, 1988; Belyavsky, A. et al., Nucleic Acids Res. 17, 2919-2932, 1989). The 5'-RACE method was performed using 5'-Ampli FINDER RACE Kit (CLONETECH) in accordance with the instructions included in the kit. In this method, the primer used for synthesis of cDNA was MHC2 primer (SEQ ID NO: 1) which is capable of hybridizing to mouse H-chain C-region. The above-prepared mRNA (about 2 μg), which was a template for the cDNA synthesis, was mixed with MHC2 primer (10 pmoles). The resulting mixture was reacted with a reverse transcriptase at 52° C. for 30 minutes to effect the reverse transcription of the mRNA into cDNA.

The resulting reaction solution was added with 6N NaOH to hydrolyze any RNA remaining therein (at 65° C. for 30 min.) and then subjected to ethanol precipitation to isolate and purify the cDNA as a precipitate. The purified cDNA was ligated to Ampli FINDER Anchor (SEQ ID NO: 42) at the 5' end by reacting with T4 DNA ligase at 37° C. for 6 hours and additionally at room temperature for 16 hours. As the primers for amplification of the cDNA by PCR method, Anchor primer (SEQ ID NO: 2) and MHC-G1 primer (SEQ ID NO: 3) (S. T. Jones, et al., Biotechnology, 9, 88, 1991) were used.

The PCR solution comprised (per 50 μl) 10 mM Tris-HCl (pH 8.3), 50 mM KCl, 0.25 mM dNTPs (DATP, dGTP, dCTP, dTTP), 1.5 mM MgCl$_2$, 2.5 units of TaKaRa Taq (Takara Shuzo Co., Ltd.), 10 pmoles of Anchor primer, and 1 μl of the reaction mixture of the cDNA to which MHC-G1 primer and Ampli FINDER Anchor primer had been ligated, over which mineral oil (50 μl) was layered. The PCR was performed on Thermal Cycler Model 480J (Perkin Elmer) for 30 cycles under the conditions: 94° C. for 45 sec.; 60° C. for 45 sec.; and 72° C. for 2 min.

(ii) Cloning of cDNA for #23-57-137-1 Antibody L-Chain V-Region

A gene encoding L-chain V-region of the mouse monoclonal antibody against human PTHrP was cloned by 5'-RACE method (Frohman, M. A. et al., Proc. Natl. Acad. Sci. USA, 85, 8998-9002, 1988; Belyavsky, A. et al., Nucleic Acids Res. 17, 2919-2932, 1989). The 5'-RACE method was performed using 5'-Ampli Finder RACE Kit (CLONETECH) in accordance with the instructions included in the kit. In this method, oligo-dT primer was used as the primer for synthesizing cDNA. The above-prepared mRNA (about 2 μg), which was a template for the cDNA synthesis, was mixed with oligo-dT primer. The resulting mixture was reacted with a reverse transcriptase at 52° C. for 30 min. to effect the reverse transcription of the mRNA into cDNA. The resulting reaction solution was added with 6N NaOH to hydrolyze any RNA remaining therein (at 65° C. for 30 min.). The resulting solution was subjected to ethanol precipitation to isolate and purified the cDNA as a precipitate. The cDNA thus synthesized was ligated to Ampli FINDER Anchor at the 5' end by reacting with T4 DNA ligase at 37° C. for 6 hours and additionally at room temperature for 16 hours.

A PCR primer MLC (SEQ ID NO: 4) was designed based on the conserved sequence of mouse L-chain λ chain C-region and then synthesized using 394 DNA/RNA Synthesizer (ABI). The PCR solution comprised (per 100 μl) 10 mM Tris-HCl (pH 8.3), 50 mM KCl, 0.25 mM dNTPs (dATP, dGTP, dCTP, dTTP), 1.5 mM MgCl$_2$, 2.5 units of AmpliTaq (PERKIN ELMER), 50 pmoles of Anchor primer (SEQ ID NO: 2), and 1 μl of the reaction mixture of the cDNA to which MLC (SEQ ID NO: 4) and Ampli FINDER Anchor were ligated, over which mineral oil (50 μl) was layered. The PCR reaction was performed on Thermal Cycler Model 480J (Perkin Elmer) for 35 cycles under the conditions: 94° C. for 45 sec.; 60° C. for 45 sec.; and 72° C. for 2 min.

(3) Purification and Fragmentation of PCR Products

Each of the DNA fragments amplified by PCR method described above was separated by agarose gel electrophoresis on a 3% Nu Sieve GTG agarose (FMC Bio. Products). For each of the H-chain V-region and the L-chain V-region, an agarose gel segment containing a DNA fragment of about 550 bp was excised from the gel. Each of the gel segments was subjected to purification of the DNA fragment of interest using GENECLEAN II Kit (BIO101) in accordance with the instructions included in the kit. The purified DNA was precipitated with ethanol, and the DNA precipitate was dissolved in 20 μl of a solution containing 10 mM Tris-HCl (pH 7.4) and 1 mM EDTA. An aliquot (1 μl) of the DNA solution was digested with a restriction enzyme XmaI (New England Biolabs) at 37° C. for 1 hour and further digested with a restriction enzyme EcoRI (Takara Shuzo Co., Ltd.) at 37° C. for 1 hour. The digestion solution was extracted with phenol and chloroform and then precipitated with ethanol to collect the DNA.

In this manner, two DNA fragments containing a gene encoding mouse H-chain V-region and a gene encoding mouse L-chain V-region, respectively, were obtained, both which had an EcoRI recognition sequence on the 5' end and an XmaI recognition sequence on the 3' end.

The EcoRI-XmaI DNA fragments containing a gene encoding mouse H-chain V-region and a gene encoding mouse L-chain V-region, respectively, were separately ligated to pUC19 vector that had been digested with EcoRI and XmaI at 16° C. for 1 hour using DNA Ligation Kit ver.2 (Takara Shuzo Co., Ltd.) in accordance with the instructions included in the kit. An aliquot (10 μl) of the ligation mixture was added to 100 μl of a solution containing competent cells of E. coli, JM109 (Nippon Gene Co., Ltd.). The cell mixture was allowed to stand on ice for 15 min., at 42° C. for 1 min. and additionally for 1 min. on ice. The resulting cell mixture was added with 300 μl of SOC medium (Molecular Cloning: A Laboratory Manual, Sambrook, et al., Cold Spring Harbor Laboratory Press, 1989) and then incubated at 37° C. for 30 min. The resulting cell solution was plated on LB agar medium or 2xYT agar medium (Molecular Cloning: A Laboratory Manual, Sambrook, et al., Cold Spring Harbor Laboratory Press, 1989) containing either 100 or 50 μg/ml of ampicillin, 0.1 mM of IPTG and 20 μg/ml of X-gal, and then incubated at 37° C. overnight. In this manner, E. coli transformants were prepared.

The transformants were cultured at 37° C. overnight in 2 ml of LB or 2xYT medium containing either 100 or 50 μg/ml of ampicillin. The cell fraction was applied to Plasmid Extracter PI-100Σ (Kurabo Industries, Ltd.) or QIAprep Spin Plasmid Kit (QIAGEN) to give a plasmid DNA. The plasmid DNA was sequenced as follows.

(4) Sequencing of Genes Encoding Mouse Antibody V-Regions

The nucleotide sequence of the cDNA coding region carried on the plasmid was determined in DNA Sequencer 373A (ABI; Perkin-Elmer) using Dye Terminator Cycle Sequencing Kit (Perkin-Elmer). M13 Primer M4 (Takara Shuzo Co., Ltd.) (SEQ ID NO: 5) and M13 Primer RV (Takara Shuzo Co., Ltd.) (SEQ ID NO: 6) were used as the primers for sequencing, and the nucleotide sequence was confirmed in the both directions.

The plasmid containing a gene encoding mouse H-chain V-region derived from hybridoma #23-57-137-1 was designated "MBC1H04," and the plasmid containing a gene encoding mouse L-chain V-region derived from hybridoma #23-57-137-1 was designated "MBC1L24." The nucleotide sequences (including the corresponding amino acids sequences) of the gene encoding the mouse #23-57-137-1 antibody-derived H-chain V-region in plasmid MBC1H04 and the gene encoding the mouse #23-57-137-1 antibody-derived L-chain V-region in plasmid MBC1L24 were shown in SEQ ID NOs: 57 and 65, respectively. The amino acid sequences of the polypeptides for the H-chain V-region and the L-chain V-region were shown in SEQ ID NOs: 46 and 45, respectively.

The E. coli strain containing plasmid MBC1H04 and the E. coli strain containing plasmid MBC1L24 were designated "Escherichia coli JM109 (MBC1H04)" and "Escherichia coli JM109 (MBC1L24)," respectively. These E. coli strains have been deposited under the terms of the Budapest Treaty at the National Institute of Bioscience and Human-Technology, Agency of Industrial Science and Technology, Japan (1-3, Higashi 1-chome, Tsukuba-shi, Ibaraki, Japan) on Aug. 15, 1996, under the Accession No. FERM BP-5628 for Escherichia coli JM109 (MBC1H04) and FERM BP-5627 for Escherichia coli JM109 (MBC1L24), respectively.

(5) Determination of CDRs of Mouse Monoclonal Antibody #23-57-137-1 Against Human PTHrP The H-chain V-region and the L-chain V-region have general structures similar to each other, each of which has four framework regions (FRs) linked through three hypervariable regions (i.e., complementarity determining regions; CDRs). The amino acid sequences of the FRs are relatively well conserved, while the amino acid sequence of the CDRs have an extremely high variability (Kabat, E. A. et al., "Sequence of Proteins of Immunological Interest," US Dept. Health and Human Services, 1983).

In view of these facts, the homology in amino acid between the V-regions of the mouse monoclonal antibody against human PTHrP was determined with reference to the database of amino acid sequences of antibodies established by Kabat et al. Thus, the CDRs of the V-regions were determined as shown in Table 1.

The amino acid sequences of CDRs 1-3 in the L-chain V-region are shown in SEQ ID NOs: 59 to 61, respectively; and the amino acid sequences of CDRs 1-3 in the H-chain V-region are shown in SEQ ID NOs: 62 to 64, respectively.

TABLE 1

| V-region | SEQ ID NO. | CDR1 | CDR2 | CDR3 |
| --- | --- | --- | --- | --- |
| H-chain V-region | 57 | 31-35 | 50-66 | 99-107 |
| L-chain V-region | 65 | 23-34 | 50-60 | 93-105 |

Reference Example 3

Construction of Chimeric Antibody (1) Construction of Chimeric Antibody H-Chain (i) Construction of H-Chain V-Region To ligate to an expression vector carrying a genomic DNA of human H-chain C-region Cγ1, the cloned DNA encoding mouse H-chain V-region was modified by PCR method. A backward primer MBC1-S1 (SEQ ID NO: 7) was designed to hybridize to a DNA sequence encoding the 5' region of the leader sequence of the V-region and to have both a Kozak consensus sequence (Kozak, M. et al., J. Mol. Biol., 196, 947-950, 1987) and a HindIII-recognition sequence. A forward primer MBC1-a (SEQ ID NO: 8) was designed to hybridize to a DNA sequence encoding the 3' region of the J region and to have both a donor splice sequence and a BamHI-recognition sequence. The PCR reaction was performed using TaKaRa Ex Taq (Takara Shuzo Co., Ltd.) and a buffer appended thereto. The PCR solution comprised (per 50 μl) 0.07 μg of plasmid MBC1H04 as a template DNA, 50 pmoles of MBC1-a and 50 pmoles of MBC1-S1 as primers, 2.5 U of TaKaRa Ex Taq and 0.25 mM dNTPs in the buffer, over which 50 μl of mineral oil was layered. The PCR was run for 30 cycles under the conditions: 94° C. for 1 min.; 55° C. for 1 min.; 72° C. for 2 min. The DNA fragments thus amplified by the PCR method were separated by agarose gel electrophoresis on a 3% Nu Sieve GTG Agarose (FMC Bio. Products).

Then, an agarose gel segment containing a DNA fragment of 437 bp was excised, and the DNA fragment was purified therefrom using GENECLEAN II Kit (BIO101) in accordance with the instructions included in the kit. The purified DNA was collected by ethanol precipitation, and then dissolved in 20 μl of a solution containing 10 mM Tris-HCl (pH 7.4) and 1 mM EDTA. An aliquot (1 μl) of the resulting DNA solution was digested with restriction enzymes BamHI and HindIII (Takara Shuzo Co., Ltd.) at 37° C. for 1 hour. The digestion solution was extracted with phenol and chloroform and then precipitated with ethanol to collect the DNA of interest.

The obtained HindIII-BamHI DNA fragment, which containing a gene encoding the mouse H-chain V-region, was subcloned into pUC19 vector that had been digested with HindIII and BamHI. The resulting plasmid was sequenced on DNA Sequencer 373A (Perkin-Elmer) using M13 Primer M4 and M13 Primer RV as primers and Dye Terminator Cycle Sequencing Kit (Perkin-Elmer). As a result, a plasmid which carried a gene of correct nucleotide sequence encoding the mouse H-chain V-region derived from hybridoma #23-57-137-1 and had a HindIII-recognition sequence and a Kozak sequence on its 5' region and a BamHI-recognition sequence on its 3' region was obtained, which was designated "MBC1H/pUC19."

(ii) Construction of H-Chain V-Region for Preparation of cDNA-Type of Mouse-Human Chimeric H-Chain To ligate to cDNA of the human H-chain C-region Cγ1, the DNA encoding the mouse H-chain V-region constructed as described above was modified by PCR method. A backward primer MBC1HVS2 (SEQ ID NO: 9) for the V-region was designed to cause the replacement of the second amino acid (asparagine) of the sequence encoding the front part of the leader sequence of the H-chain V-region by glycine and to have a Kozak consensus sequence (Kozak, M. et al., J. Mol. Biol., 196, 947-950, 1987) and HindIII- and EcoRI-recognition sequences. A forward primer MBC1HVR2 (SEQ ID NO: 10) for the H-chain V-region was designed to hybridize to a DNA sequence encoding the 3' region of the J region, to encode the 5' region of the C-region and to have ApaI- and SmaI-recognition sequences.

The PCR reaction was performed using TaKaRa Ex Taq (Takara Shuzo Co., Ltd.) and a buffer appended thereto. The PCR solution comprised (per 50 μl) 0.6 μg of plasmid MBC1H/pUC19 as a template DNA, 50 pmoles of MBC1HVS2 and 50 pmoles of MBC1HVR2 as primers, 2.5 U of TaKaRa Ex Taq and 0.25 mM of dNTPs in the buffer, over which 50 μl of mineral oil was layered. The PCR reaction was run for 30 cycles under the conditions: 94° C. for 1 min.; 55° C. for 1 min.; 72° C. for 1 min. The DNA fragments amplified by the PCR reaction were separated by agarose gel electrophoresis on a 1% Sea Kem GTG Agarose (FMC Bio. Products). Then, an agarose gel segment containing a DNA fragment of 456 bp was excised and the DNA fragment was purified therefrom using GENECLEAN II Kit (BIO101) in accordance with the instructions included in the kit. The purified DNA was precipitated with ethanol and then dissolved in 20 μl of a solution containing 10 mM Tris-HCl (pH 7.4) and 1 mM EDTA.

The resulting DNA solution (1 μl) was digested with restriction enzymes EcoRI and SmaI (Takara Shuzo Co., Ltd.) at 37° C. for 1 hour. The digestion solution was extracted with phenol and chloroform and then precipitated with ethanol to collect the DNA. The obtained EcoRI-SmaI DNA fragment, which containing a gene encoding the mouse H-chain, was subcloned into pUC19 vector that had been digested with EcoRI and SmaI. The resulting plasmid was sequenced on DNA Sequencer 373A (Perkin-Elmer) using M13 Primer M4 and M13 Primer RV, and Dye Terminator Cycle Sequencing Kit (Perkin-Elmer). As a result, a plasmid which contained a gene of correct nucleotide sequence encoding mouse H-chain V-region derived from hybridoma #23-57-137-1 and had EcoRI- and HindIII-recognition sequences and a Kozak sequence on its 5' region and ApaI- and SmaI-recognition sequences on its 3' region was obtained, which was designated "MBC1Hv/pUC19."

(iii) Construction of Expression Vector for Chimeric Antibody H-Chain cDNA containing the DNA for human antibody H-chain C-region Cγ1 was prepared as follows. mRNA was prepared from a CHO cell into which both an expression vector DHFR-ΔE-RVh-PM-1-f (see WO 92/19759) encoding the genomic DNAs of humanized PM1 antibody H-chain V-region and human antibody H-chain C-region IgG1 (N. Takahashi et al., Cell 29, 671-679, 1982) and an expression vector RV1-PM1a (see WO 92/19759) encoding the genomic DNAs of humanized PM1 antibody L-chain V-region and human antibody L-chain κ chain C-region had been introduced. Using the mRNA, cDNA containing the humanized PM1 antibody H-chain V-region and the human antibody C-region Cγ1 was cloned by RT-PCR method, and then subcloned into plasmid pUC19 at the HindIII-BamHI site. After sequencing, a plasmid which had the correct nucleotide sequence was obtained, which was designated "pRVh-PM1f-cDNA."

An expression vector DHFR-AE-RVh-PM-1-f in which both a HindIII site located between SV40 promoter and a DHFR gene and an EcoRI site located between EF-1α promoter and a humanized PM1 antibody H-chain V-region gene had been deleted, was prepared for the construction of an expression vector for cDNA containing the humanized PM1 antibody H-chain V-region gene and the human antibody C-region Cγ1 gene.

The plasmid obtained (pRVh-PM1f-cDNA) was digested with BamHI, blunt-ended with Klenow fragment, and further digested with HindIII, thereby obtaining a blunt-ended HindIII-BamHI fragment. The blunt-ended HindIII-BamHI fragment was ligated to the above-mentioned HindIII site- and EcoRI site-deleted expression vector DHFR-ΔE-RVh-PM1-f that had been digested with HindIII and BamHI. Thus, an expression vector RVh-PM1f-cDNA was constructed which contained cDNA encoding the humanized PM1 antibody H-chain V-region and the human antibody C-region Cγ1.

The expression vector RVh-PM1f-cDNA containing the cDNA encoding the humanized PM1 antibody H-chain V-region and the human antibody C-region Cγ1 was digested with ApaI and BamHIH, and a DNA fragment containing the H-chain C-region was collected therefrom. The resulting DNA fragment was introduced into the plasmid MBC1Hv/pUC19 that had been digested with ApaI and BamHI. The plasmid thus prepared was designated "MBC1HcDNA/pUC19." This plasmid contained cDNA encoding the mouse antibody H-chain V-region and the human antibody C-region Cγ1, and had EcoRI- and HindIII-recognition sequences on its 5' terminal end and a BamHI-recognition sequence on its 3' terminal end.

The plasmid MBC1HcDNA/pUC19 was digested with EcoRI and BamHI to give a DNA fragment comprising a nucleotide sequence encoding the chimeric antibody H-chain. The resulting DNA fragment was introduced into an expression vector pCOS1 that had been digested with EcoRI and BamHI, thereby giving an expression vector for the chimeric antibody, which was designated "MBC1HcDNA/pCOS1." Here, the expression vector pCOS1 was constructed using HEF-PMh-gγ1 (see WO 92/19759) by deleting therefrom an antibody genes by digestion with EcoRI and SmaI, and then ligating it to EcoRI-NotI-BamHI Adaptor (Takara Shuzo Co., Ltd.).

For preparing a plasmid for the expression in a CHO cell, the plasmid MBC1HcDNA/pUC19 was digested with EcoRI and BamHI to obtain a DNA fragment containing a gene for the chimeric antibody H-chain. The DNA fragment was then introduced into an expression plasmid pCHO1 that had been digested with EcoRI and BamHI to give an expression plasmid for the chimeric antibody, which was designated "MBC1HcDNA/pCHO1." Here, the expression vector pCHO1 was constructed using DHFR-ΔE-rvH-PM1-f (see WO 92/19759) by deleting therefrom an antibody gene by digestion with EcoRI and SmaI, and then ligating it to EcoRI-NotI-BamHI Adaptor (Takara Shuzo Co., Ltd.).

(2) Construction of Human L-Chain C-Region (i) Preparation of Cloning Vector

To construct pUC19 vector containing a gene for human L-chain C-region, a HindIII site-deleted pUC19 vector was prepared. pUC19 vector (2 μg) was digested in 20 μl of a reaction solution containing 20 mM Tris-HCl (pH 8.5), 10 mM MgCl$_2$, 1 mM DTT, 100 mM KCl, 8 U of HindIII (Takara Shuzo Co., Ltd.) at 37° C. for 1 hour. The resulting digestion solution was extracted with phenol and chloroform, and then subjected to ethanol precipitation to collect the DNA of interest.

The DNA collected was reacted in 50 µl of a reaction solution containing 50 mM Tris-HCl (pH 7.5), 10 mM MgCl$_2$, 1 mM DTT, 100 mM NaCl, 0.5 mM dNTPs and 6 U of Klenow fragment (GIBCO BRL) at room temperature for 20 min., thereby rendering the terminal ends of the DNA blunt. This reaction mixture was extracted with phenol and chloroform and then subjected to ethanol precipitation to collect the vector DNA.

The vector DNA thus collected was reacted in 10 µl of a reaction solution containing 50 mM Tris-HCl (pH 7.6), 10 mM MgCl$_2$, 1 mM ATP, 1 mM DTT, 5% (v/v) polyethylene glycol-8000 and 0.5 U of T4 DNA ligase (GIBCO BRL) at 16° C. for 2 hours, to cause self-ligation of the vector DNA. The reaction solution (5 µl) was added to 100 µl of a solution containing competent cells of *E. coli*, JM109 (Nippon Gene Co., Ltd.), and the resulting solution was allowed to stand on ice for 30 min., at 42° C. for 1 min., and additionally on ice for 1 min. SOC culture medium (500 µl) was added to the reaction solution and then incubated at 37° C. for 1 hour. The resulting solution was plated on 2xYT agar medium (containing 50 µg/ml of ampicillin) on which X-gal and IPTG had been applied (Molecular Cloning: A Laboratory Manual, Sambrook, et al., Cold Spring Harbor Laboratory Press, 1989), and then cultured at 37° C. overnight, thereby obtaining a transformant.

The transformant was cultured in 2xYT medium (20 ml) containing ampicillin (50 µg/ml) at 37° C. overnight. From the cell fraction of the culture medium, a plasmid DNA was isolated and purified using Plasmid Mini Kit (QIAGEN) in accordance with the instructions included in the kit. The purified plasmid was digested with HindIII. The plasmid that was confirmed to have a HindIII site-deletion was designated "pUC19 ΔHindIII."

(ii) Construction of Gene Encoding Human L-Chain λ Chain C-Region

Human antibody L-chain λ chain C-region is known to have at least four isotypes including Mcg$^+$Ke$^+$Oz$^-$, Mcg$^-$Ke$^-$Oz$^-$, Mcg$^-$Ke$^-$Oz$^+$ and Mcg$^-$Ke$^+$Oz$^-$ (P. Dariavach, et al., Proc. Natl. Acad. Sci. USA, 84, 9074-9078, 1987). A search was made for a human antibody L-chain λ chain C-region homologous to the #23-57-137-1 mouse L-chain λ chain C-region from the EMBL database. As a result, it was found that the isotype Mcg$^+$Ke$^+$Oz$^-$ of the human antibody L-chain λ chain (Accession No. X57819) (P. Dariavach, et al., Proc. Natl. Acad. Sci. USA, 84, 9074-9078, 1987) showed the highest degree of homology to the #23-57-137-1 mouse L-chain λ chain C-region, with a 64.4% homology in terms of amino acid sequence and a 73.4% homology in terms of nucleotide sequence.

Then, a gene encoding the human antibody L-chain λ chain C-region was constructed by PCR method. The primers for the PCR were synthesized using 394 DNA/RNA Synthesizer (ABI). The synthesized primers were as follows: HLAMB1 (SEQ ID NO: 11) and HLAMB3 (SEQ ID NO: 13), both having a sense DNA sequence; and HLAMB2 (SEQ ID NO: 12) and HLAMB4 (SEQ ID NO: 14), both having an antisense DNA sequence; each primer containing a complementary sequence of 20-23 bp on the both terminal ends.

External primers HLAMBS (SEQ ID NO: 15) and HLAMBR (SEQ ID NO: 16) had sequences homologous to the primers HLAMB1 and HLAMB4, respectively. HLAMBS contained EcoRI-, HindIII- and BlnI-recognition sequences, and HLAMBR contained an EcoRI-recognition sequence. In the first-round PCR reaction, the reactions between HLAMB1 and HLAMB2 and between HLAMB3 and HLAMB4 were performed. After the reactions were completed, both of the resulting PCR products were mixed in equivalent quantities, and then assembled in the second-round PCR reaction. The reaction solution was added with the external primers HLAMBS and HLAMBR. This reaction mixture was subjected to the third-round PCR reaction to amplify the full length DNA.

Each PCR reaction was performed using TaKaRa Ex Taq (Takara Shuzo Co., Ltd.) in accordance with the instructions included in the kit. In the first-round PCR reaction, 100 µl of either a reaction solution containing 5 pmoles of HLAMB1, 0.5 pmoles of HLAMB2 and 5 U of TaKaRa Ex Taq (Takara Shuzo Co., Ltd.) or a reaction solution containing 0.5 pmoles of HLAMB3, 5 pmoles of HLAMB4 and 5 U of TaKaRa Ex Taq (Takara Shuzo Co., Ltd.) was used, over which 50 µl of mineral oil was layered. The PCR reaction was run for 5 cycles under the conditions: 94° C. for 1 min., 60° C. for 1 min. and 72° C. for 1 min.

In the second-round PCR reaction, a mixture of both the reaction solutions (50 µl each) was used, over which 50 µl of mineral oil was layered. The PCR reaction was run for 3 cycles under the conditions: 94° C. for 1 min., 60° C. for 1 min. and 72° C. for 1 min.

In the third-round PCR reaction, the reaction solution to which the external primers HLAMBS and HLAMBR (50 pmoles each) were added was used. The PCR reaction was run for 30 cycles under the conditions: 94° C. for 1 min., 60° C. for 1 min. and 72° C. for 1 min.

The DNA fragment obtained by the third-round PCR reaction was subjected to electrophoresis on a 3% low-melting agarose gel (NuSieve GTG Agarose, FMC), and separated and purified from the gel using GENECLEAN II Kit (BIO101) in accordance with the instructions included in the kit.

The DNA fragment obtained was digested in a reaction solution (20 µl) containing 50 mM Tris-HCl (pH 7.5), 10 mM MgCl$_2$, 1 mM DTT, 100 mM NaCl and 8 U of EcoRI (Takara Shuzo Co., Ltd.) at 37° C. for 1 hour. The digestion solution was extracted with phenol and chloroform, and the DNA was collected therefrom by the ethanol precipitation. The DNA was dissolved in a solution (8 µl) containing 10 mM Tris-HCl (pH 7.4) and 1 mM EDTA.

The above-prepared plasmid pUC19 ΔHindIII (0.8 µg) was digested with EcoRI in the same manner as set forth above. The digestion solution was subjected to phenol/chloroform extraction and then ethanol precipitation, thereby giving a digested plasmid pUC19 ΔHindIII. The digested plasmid was reacted in a reaction solution (50 µl) containing 50 mM Tris-HCl (pH 9.0), 1 mM MgCl$_2$ and alkaline phosphatase (*E. coli* C75; Takara Shuzo Co., Ltd.) at 37° C. for 30 min. to dephosphorylate (i.e., BAP-treat) the plasmid. The reaction solution was subjected to phenol/chloroform extraction, and the DNA was collected therefrom by ethanol precipitation. The DNA thus obtained was dissolved in a solution (10 µl) containing 10 mM Tris-HCl (pH 7.4) and 1 mM EDTA.

The BAP-treated plasmid pUC19 ΔHindIII (1 µl) was ligated to the above-obtained PCR product (4 µl) using DNA Ligation Kit Ver.2 (Takara Shuzo Co., Ltd.). The resulting plasmid was introduced into a competent cell of *E. coli*, JM109, to give a transformant. The transformant was cultured overnight in 2xYT medium (2 ml) containing 50 µg/ml of ampicillin. From the cell fraction, the plasmid was isolated using QIAprep Spin Plasmid Kit (QIAGEN).

The plasmid obtained was sequenced for the cloned DNA part. The sequencing was performed on 373A DNA Sequencer (ABI) using M13 Primer M4 and M13 Primer RV (Takara Shuzo Co., Ltd.). As a result, it was found that the cloned DNA had a 12-bp deletion therein. The plasmid was designated "CλΔ/pUC19." Then, for making up for the deleted part, primers HCLMS (SEQ ID NO: 17) and HCLMR (SEQ ID NO: 18) were newly synthesized, and a DNA of correct sequence was reconstructed using these primers by PCR method.

In the first-round PCR reaction, the plasmid CλΔ/pUC19 having the DNA deletion therein was used as a template, and the reaction was performed with each of the primer sets of HLAMBS and HCLMS and HCLMS and HLAMB4. The PCR products were purified separately. In the second-round PCR reaction, the PCR products were assembled together. In the third-round PCR reaction, the reaction product of the second-round PCR reaction was added with external primers HLAMBS and HLAMB4 and amplified to give the full length DNA.

In the first-round PCR reaction, a reaction solution (100 μl) containing 0.1 μg of CλΔ/pUC19 as a template, either 50 pmoles of each of the primers HLAMBS and HCLMR or 50 pmoles of each of the primers HCLMS and HLAMB4, and 5 U of TaKaRa Ex Taq (Takara Shuzo Co., Ltd.) was used, over which 50 μl of mineral oil was layered. The PCR reaction was run for 30 cycles under the conditions: 94° C. for 1 min., 60° C. for 1 min. and 72° C. for 1 min.

The PCR products of the first-round PCR reaction, HLAMBS-HCLMR (236 bp) and HCLMS-HLAMB4 (147 bp), were subjected to electrophoresis separately on a 3% low-melting agarose gel to isolate the DNA fragments. The DNA fragments were collected and purified from the gels using GENECLEAN II Kit (BIO101). In the second-round PCR reaction, 20 μl of a reaction solution containing 40 ng of each of the purified DNA fragments and 1 U of TaKaRa Ex Taq (Takara Shuzo Co., Ltd.) was used, over which 25 μl of mineral oil was layered. The PCR reaction was run for 5 cycles under the conditions: 94° C. for 1 min., 60° C. for 1 min. and 72° C. for 1 min.

In the third-round PCR reaction, 100 μl of a reaction solution containing 2 μl of the reaction solution obtained by the second-round PCR reaction, 50 pmoles of each of external primers HLAMBS and HLAMB4 and 5 U of TaKaRa Ex Taq (Takara Shuzo Co., Ltd.) was used, over which 50 μl of mineral oil was layered. The PCR reaction was run for 30 cycles under the conditions: 94° C. for 1 min., 60° C. for 1 min. and 72° C. for 1 min., thereby obtaining a DNA fragment of 357 bp (the third PCR product). The DNA fragment was subjected to electrophoresis on a 3% low-melting agarose gel to isolate the DNA fragment. The resulting DNA fragment was collected and purified using GENECLEAN II Kit (BIO101).

An aliquot (0.1 μg) of the DNA fragment thus obtained was digested with EcoRI, and then subcloned into plasmid pUC19 ΔHindIII that had been BAP-treated. The resulting plasmid was introduced into a competent cell of E. coli, JMI09, to form a transformant. The transformant was cultured overnight in 2 ml of 2xYT medium containing 50 μg/ml of ampicillin. From the cell fraction, the plasmid was isolated and purified using QIAprep Spin Plasmid Kit (QIAGEN).

The purified plasmid was sequenced on 373A DNA Sequencer (ABI) using M13 Primer M4 and M13 Primer RV (Takara Shuzo Co., Ltd.). The plasmid that was confirmed to have the correct nucleotide sequence without any deletion was designated "CkpUC19."

(iii) Construction of Gene Encoding Human L-Chain κ Chain C-Region

A DNA fragment encoding the L-chain κ chain C-region was cloned from plasmid HEF-PM1k-gk (WO 92/19759) by PCR method. A forward primer HKAPS (SEQ ID NO: 19) was designed to contain EcoRI-, HindIII- and BlnI-recognition sequences, and a backward primer HKAPA (SEQ ID NO: 20) was designed to contain an EcoRI-recognition sequence. These primers were synthesized on 394 DNA/RNA Synthesizer (ABI).

A PCR reaction was performed using 100 μl of a reaction solution containing 0.1 μg of plasmid HEF-PM1k-gk as a template, 50 pmoles of each of primers HKAPS and HKAPA and 5 U of TaKaRa Ex Taq (Takara Shuzo Co., Ltd.), over which 50 μl of mineral oil was layered. The PCR reaction was run for 30 cycles under the conditions: 94° C. for 1 min., 60° C. for 1 min. and 72° C. for 1 min., thereby giving a PCR product of 360 bp. The DNA fragment was isolated and purified by electrophoresis on a 3% low-melting agarose, and then collected and purified using GENECLEAN II Kit (BIO101).

The DNA fragment thus obtained was digested with EcoRI, and then cloned into plasmid pUC19 ΔHindIII that had been BAP-treated. The resulting plasmid was introduced into a competent cell of E. coli, JM109, to form a transformant. The transformant was cultured overnight in 2 ml of 2xYT medium containing 50 μg/ml of ampicillin. From the cell fraction, the plasmid was purified using QIAprep Spin Plasmid Kit (QIAGEN).

The purified plasmid was sequenced on 373A DNA Sequencer (ABI) using M13 Primer M4 and M13 Primer RV (Takara Shuzo Co., Ltd.). The plasmid that was confirmed to have the correct nucleotide sequence was designated "Cκ/pUC19."

(3) Construction of Chimeric Antibody L-Chain Expression Vector

An expression vector for the chimeric #23-57-137-1 antibody L-chain was constructed. A gene encoding #23-57-137-1 L-chain V-region was ligated to the HindIII-BlnI site (located just in front of the human antibody C-region) of each of the plasmids Cλ/pUC19 and Cκ/pUC19, thereby obtaining pUC19 vectors that contained the DNAs encoding the chimeric #23-57-137-1 antibody L-chain V-region and either of the L-chain λ chain C-region or the L-chain κ chain C-region, respectively. Each of the resulting vectors was then digested with EcoRI to separate the gene for the chimeric antibody L-chain. The gene was subcloned into HEF expression vector.

That is, a DNA fragment encoding #23-57-137-1 antibody L-chain V-region was cloned from plasmid MBC1L24 by PCR method. Primers used in the PCR method were separately synthesized using 394 DNA/RNA Synthesizer (ABI). A backward primer MBCCHL1 (SEQ ID NO: 21) was designed to contain a HindIII-recognition sequence and a Kozak sequence (Kozak, M. et al., J. Mol. Biol. 196, 947-950, 1987), and a forward primer MBCCHL3 (SEQ ID NO: 22) was designed to contain BglII- and RcoRI-recognition sequences.

The PCR reaction was performed using 100 μl of a reaction solution containing 10 mM Tris-HCl (pH 8.3), 50 mM KCl, 1.5 mM $MgCl_2$, 0.2 mM dNTPs, 0.1 μg of MBC1L24, 50 pmoles of each of primers MBCCHL1 and MBCCHL3 and 1 μl of AmpliTaq (PERKIN ELMER), over which 50 μl of mineral oil was layered. The PCR reaction was run for 30 cycles under the conditions: 94° C. for 45 sec., 60° C. for 45 sec. and 72° C. for 2 min.

A PCR product of 444 bp was electrophoresed on a 3% low-melting agarose gel, and collected and purified using GENECLEAN II Kit (BIO101). The purified PCR product was dissolved in 20 µl of a solution containing 10 mM Tris-HCl (pH 7.4) and 1 mM EDTA. The PCR product (1 µl) was digested in 20 µl of a reaction solution containing 10 mM Tris-HCl (pH 7.5), 10 mM MgCl$_2$, 1 mM DTT, 50 mM NaCl, 8 U of HindIII (Takara Shuzo Co., Ltd.) and 8 U of EcoRI (Takara Shuzo Co., Ltd.) at 37° C. for 1 hour. The digestion solution was subjected to phenol/chloroform extraction, and the DNA of interest was collected therefrom by ethanol precipitation. The DNA was dissolved in 8 µl of a solution containing 10 mM Tris-HCl (pH 7.4) and 1 mM EDTA.

In the same manner, plasmid pUC19 (1 µg) was digested with HindIII and EcoRI, and subjected to phenol/chloroform extraction and then ethanol precipitation. The obtained digested plasmid was BAP-treated with alkaline phosphatase (*E. coli* C75; Takara Shuzo Co., Ltd.). The resulting reaction solution was extracted with phenol and chloroform, and the DNA was collected therefrom by ethanol precipitation. The DNA was dissolved in 10 µl of a solution containing 10 mM Tris-HCl (pH 7.4) and 1 mM EDTA.

The BAP-treated plasmid pUC19 (1 µl) was ligated to the above-obtained PCR product (4 µl) using DNA Ligation Kit Ver. 2 (Takara Shuzo Co., Ltd.). The resulting plasmid was introduced into a competent cell of *E. coli*, JM109 (Nippon Gene Co., Ltd.), in the same manner as set forth above, to form a transformant. The transformant was plated on 2xYT agar medium containing 50 µg/ml of ampicillin and cultured at 37° C. overnight. The resulting transformant was then cultured at 37° C. overnight in 2 ml of 2xYT medium containing 50 µg/ml of ampicillin. From the cell fraction, the plasmid was purified using QIAprep Spin Plasmid Kit (QIAGEN). After determining the nucleotide sequence, the plasmid that was confirmed to have the correct nucleotide sequence was designated "CHL/pUC19."

Each of plasmids Cλ/pUC19 and Cκ/pUC19 (1 µg each) was digested in 20 µl of a reaction solution containing 20 mM Tris-HCl (pH 8.5), 10 mM MgCl$_2$, 1 mM DTT, 100 mM KCl, 8 U of HindIII (Takara Shuzo Co., Ltd.) and 2 U of BlnI (Takara Shuzo Co., Ltd.) at 37° C. for 1 hour. The digestion solution was extracted with phenol and chloroform, and the DNA was collected therefrom by ethanol precipitation. The DNA was BAP-treated at 37° C. for 30 min. The reaction solution was extracted with phenol and chloroform, and the DNA was collected therefrom by ethanol precipitation. The DNA was dissolved in 10 µl of a solution containing 10 mM Tris-HCl (pH 7.4) and 1 mM EDTA.

The plasmid CHL/pUC19 (8 µg) that contained DNA encoding #23-57-137-1-L-chain V-region was digested with HindIII and BlnI in the same manner as set forth above to give a DNA fragment of 409 bp. The DNA fragment was electrophoresed on a 3% low-melting agarose gel, and then collected and purified from the gel using GENECLEAN II Kit (BIO101). The DNA was dissolved in 10 µl of a solution containing 10 mM Tris-HCl (pH 7.4) and 1 mM EDTA.

The DNA for L-chain V-region (4 µl) was subcloned into 1 µl of each of the BAP-treated plasmids Cλ/pUC19 and Cκ/pUC19, and then introduced into a competent cell of *E. coli*, JM109, to form a transformant. The transformant was cultured overnight in 3 ml of 2xYT medium containing 50 µg/ml of ampicillin. From the cell fraction, the plasmid was isolated and purified using QIAprep Spin Plasmid Kit (QIAGEN). The two plasmids thus prepared were designated "MBC1L(κ)/pUC19" and "MBC1L(κ)/pUC19," respectively.

Each of plasmids MBC1L(λ)/pUC19 and MBC1L(κ)/pUC19 was digested with EcoRI and then subjected to electrophoresis on a 3% low-melting agarose gel. A DNA fragment of 743 bp was isolated and purified from the gel using GENECLEAN II Kit (BIO 101), and then dissolved in 10 µl of a solution containing 10 mM Tris-HCl (pH 7.4) and 1 mM EDTA.

An expression vector (plasmid HEF-PM1k-gk) (2.7 µg) was digested with EcoRI and then extracted with phenol and chloroform, and the DNA was collected therefrom by ethanol precipitation. The DNA fragment was BAP-treated, and then subjected to electrophoresis on a 1% low-melting agarose gel. From the gel, a DNA fragment of 6561 bp was isolated and purified GENECLEAN II Kit (BIO101). The purified DNA fragment was dissolved in 10 µl of a solution containing 10 mM Tris-HCl (pH 7.4) and 1 mM EDTA.

BAP-treated HEF vector (2 µl) was ligated to an EcoRI fragment (3 µl) of each of plasmid MBC1L(λ)/pUC19 and MBC1L(κ)/pUC19. The ligation product was introduced into a competent cell of *E. coli*, JM109, to form a transformant. The transformant was cultured in 2 ml of 2xYT medium containing 50 µg/ml of ampicillin. From the cell fraction, the plasmid was purified using QIAprep Spin Plasmid Kit (QIAGEN).

The purified plasmid was digested in 20 µl of a reaction solution containing 20 mM Tris-HCl (pH 8.5), 10 mM MgCl$_2$, 1 mM DTT, 100 mM KCl, 8 U of HindIII (Takara Shuzo Co., Ltd.) and 2 U of PvuI (Takara Shuzo Co., Ltd.) at 37° C. for 1 hour. This reaction gave digestion fragments of 5104/2195 bp if the fragment was inserted in the correct orientation, or gave digestion fragments of 4378/2926 bp if the fragment was inserted in the reverse orientation. The plasmid that was confirmed to have the fragment in the correct orientation was designated "MBC1L(λ)/neo" for plasmid MBC1 L(λ)/pUC19 or "MBC1L(κ)/neo" for plasmid MBC1L(κ)/pUC19.

(4) Transfection of COS-7 Cell

To evaluate the antigen-binding activity and the neutralizing activity of the chimeric antibodies, the expression plasmids prepared above were separately expressed transiently in a COS-7 cell.

The transient expression of the chimeric antibodies was performed using each of the combinations of plasmids MBC1HcDNA/pCOS1 and MBC1L(λ)/neo and plasmids MBC1HcDNA/pCOS1 and MBC1L(κ)/neo, by co-transfecting a COS-7 cell with the plasmids by electroporation using Gene Pulser (Bio Rad). That is, the plasmids (10 µg each) were added to a COS-7 cell suspension (0.8 ml; 1×10$^7$ cells/ ml) in PBS(−). The resulting solution was applied with pulses at an electrostatic capacity of 1,500V and 2 µF to cause electroporation. After 10 min. of recovery period at room temperature, the electroporated cells were suspended in DMEM medium (GIBCO) containing 2% Ultra Low IgG fetal calf serum (GIBCO), and then cultured using a 10-cm culture dish in a CO$_2$ incubator. After culturing for 72 hours, a culture supernatant was collected and centrifuged to remove cell debris, and was provided for use as a sample for the subsequent ELISA.

In this procedure, the purification of the chimeric antibody from the COS-7 cell culture supernatant was performed using AffiGel Protein A MAPS II Kit (Bio Rad) in accordance with the instructions included in the kit.

(5) ELISA (i) Determination of Antibody Concentration

An ELISA plate for determining antibody concentration was prepared as follows. Each well of a 96-well ELISA plate (Maxisorp, NUNC) was coated with 100 µl of a coating buffer (0.1 M NaHCO$_3$, 0.02% NaN$_3$) supplemented with 1 µg/ml of goat anti-human IgG antibody (TAGO), and then blocked with 200 µl of a dilution buffer [50 mM Tris-HCl, 1 mM MgCl$_2$, 0.1 M NaCl, 0.05% Tween 20, 0.02% NaN$_3$, 1% bovine serum albumin (BSA); pH 7.2]. Each well of the plate was added with each of the serial dilutions of the COS-7 cell culture supernatant in which each of the chimeric antibodies had been expressed, or added with each of the serial dilutions of each of the chimeric antibodies per se in a purified form. The plate was incubated at room temperature for 1 hour and washed with PBS-Tween 20. Each well of the plate was then added with 100 µl of a solution of alkaline phosphatase-conjugated goat anti-human IgG antibodies (TAGO). After the plate was incubated at room temperature for 1 hour and washed with PBS-Tween 20, each well was added with 1 mg/ml of a substrate solution ("Sigma 104"; p-nitrophenylphosphoric acid, SIGMA). The solution was measured on its absorbance at 405 nm using Microplate Reader (Bio Rad) to determine the antibody concentration. In this determination, Hu IgG1λ Purified (The Binding Site) was used as the standard substance.

(ii) Determination of Antigen-Binding Ability

An ELISA plate for the determination of antigen-binding ability was prepared as follows. Each well of a 96-well ELISA plate was coated with 100 µl of a coating buffer supplemented with 1 µg/ml of human PTHrP (1-34) (Peptide Research Institute), and then blocked with 200 µl of a dilution buffer. Each well was added with each of the serial dilutions of the COS-7 cell culture supernatant in which each of the chimeric antibodies had been expressed, or added with each of the serial dilutions of each of the chimeric antibodies per se in a purified form. After the plate was incubated at room temperature and washed with PBS-Tween 20, each well of the plate was added with 100 µl of a solution of alkaline phosphatase-conjugated goat anti-human IgG antibodies (TAGO). After the plate was incubated at room temperature and washed with PBS-Tween 20, each well of the plate was added with 1 mg/ml of a substrate solution ("Sigma 104"; p-nitrophenylphosphoric acid, SIGMA). The solution was measured on its absorbance at 405 nm using Microplate Reader (Bio Rad).

As a result, it was found that the chimeric antibodies had an ability to bind to human PTHrP (1-34) and the cloned mouse antibody V-regions had the correct structures. It was also found that there was no difference in the ability to bind to PTHrP (1-34) between the chimeric antibody with L-chain λ chain C-region and the chimeric antibody with L-chain κ chain C-region. Therefore, the humanized antibody L-chain λ chain was used for construction of the L-chain C-region of the humanized antibody.

(6) Establishment of Cho Cell Line Capable of Stable Production of Chimeric Antibodies To establish a cell line capable of producing the chimeric antibodies stably, the above-prepared expression plasmids were introduced into CHO cells (DXB11).

For the establishment of a cell line capable of producing the chimeric antibodies stably, either of the following combinations of the expression plasmids for CHO cell was used: MBC1HcDNA/pCHO1 and MBC1L(λ)/neo; or MBC1HcDNA/pCHO1 and MBC1L(κ)/neo. A CHO cell was co-transfected with the plasmids by electroporation using Gene Pulser (Bio Rad) as follows. The expression vectors were separately cleaved with a restriction enzyme PvuI to give linear DNAs. The resulting DNAs were extracted with phenol and chloroform and collected by precipitation with ethanol. The plasmid DNAs thus prepared were subjected to electroporation. That is, each of the plasmid DNAs (10 µg each) was added to 0.8 ml of a cell suspension of CHO cells in PBS(-) (1×10$^7$ cells/ml). The resulting solution was applied with pulses at an electrostatic capacity of 1,500V and 25 µF. After 10 min. of recovery period at room temperature, the electroporated cells were suspended in MEM-A medium (GIBCO) containing 10% fetal calf serum (GIBCO). The resulting suspension was cultured using three 96-well plates (Falcon) in a CO$_2$ incubator. On the day following the culturing being started, the medium was replaced by a selective medium [ribonucleoside- or deoxyribonucleoside-free MEM-α medium (GIBCO) containing 10% fetal calf serum (GIBCO) and 500 mg/ml of GENETICIN (G418Sulfate; GIBCO)]. From the culture medium, cells into which the antibody gene was introduced were selected. The selective medium was replaced by a fresh one. About two weeks after the medium replacement, the cells were observed under a microscope. When a satisfactory cell growth was observed, the amount of the antibodies produced was determined by ELISA as set forth above. Among the cells, those cells which produced a larger amount of antibodies were screened.

Then, the culturing of the established cell line capable of stable production of the antibodies was scaled up in a roller bottle using ribonucleoside- or deoxyribonucleoside-free MEM medium containing 2% Ultra Low IgG fetal calf serum. On day 3 or day 4 of the culturing, the culture supernatant was collected and then filtered on a 0.2-µm filter (Millipore) to remove cell debris therefrom.

Purification of the chimeric antibodies from the CHO cell culture supernatant was performed using POROS Protein A Column (PerSeptive Biosystems) on ConSep LC100 (Millipore) in accordance with the instructions included in the kit. The purified chimeric antibodies were provided for use as samples for the determination of neutralizing activity and for pharmacological test in hypercalcemic model animals. The concentration and the antigen-binding activity of the purified chimeric antibodies were determined using the same ELISA system as set forth above.

Reference Example 4

Construction of Humanized Antibody (1) Construction of Humanized Antibody H-Chain (i) Construction of Humanized H-Chain V-Region A humanized #23-57-137-1 antibody H-chain was produced by CDR-grafting technique by means of PCR method. For the production of a humanized #23-57-137-1 antibody H-chain (version "a") having FRs derived from human antibody S31679 (NBRF-PDB; Cuisinier, A. M. et al., Eur. J. Immunol., 23, 110-118, 1993), the following six PCR primers were used: CDR-grafting primers: MBC1HGP1 (SEQ ID NO: 23) and MBC1HGP3 (SEQ ID NO: 24) (both containing a sense DNA sequence) and MBC1HGP2 (SEQ ID NO: 25) and MBC1HGP4 (SEQ ID NO: 26) (both containing an anti-sense DNA sequence), all of which containing a 15-21 bp complementary sequence on both terminal ends thereof; and external primers: MBC1HVS1 (SEQ ID NO: 27) and MBC1HVR1 (SEQ ID NO: 28) having a homology to the CDR-grafting primers MBC1HGP1 and MBC1HGP4, respectively.

The CDR-grafting primers MBC1HGP1, MBC1HGP2, MBC1HGP3 and MBC1HGP4 were separated on an urea-denatured polyacrylamide gel (Molecular Cloning: A Laboratory Manual, Sambrook, et al., Cold Spring Harbor Laboratory Press, 1989), and extracted therefrom by crush-and-soak method (Molecular Cloning: A Laboratory Manual, Sambrook, et al., Cold Spring Harbor Laboratory Press, 1989) in the following manner.

Each of the CDR-grafting primers (1 nmole) was separated on a 6% denatured polyacrylamide gel to give DNA fragments. From the resulting DNA fragments, a DNA fragment having a desired length was identified on a silica gel thin plate by irradiation of UV ray and then collected therefrom by crush-and-soak method. The resulting DNA was dissolved in 20 μl of a solution containing 10 mM Tris-HCl (pH 7.4) and 1 mM EDTA. The PCR reaction was performed using TaKaRa Ex Taq (Takara Shuzo Co., Ltd.). The PCR reaction solution (100 μl) comprised 1 μl of each of the above-mentioned CDR-grafting primers MBC1HGP1, MBC1HGP2, MBC1HGP3 and MBC1HGP4, 0.25 mM dNTPs and 2.5 U of TaKaRa Ex Taq in the buffer. The PCR reaction was run for 5 cycles under the conditions: 94° C. for 1 min., 55° C. for 1 min. and 72° C. for 1 min. The resulting reaction solution was added with the external primers MBC1HVS1 and MBC1HVR1 (50 pmoles each). Using this reaction mixture, the PCR reaction was run for additional 30 cycles under the same conditions. The DNA fragment thus amplified was separated by agarose gel electrophoresis on a 4% Nu Sieve GTG agarose (FMC Bio. Products).

An agarose segment containing a DNA fragment of 421 bp was excised, and the DNA fragment was purified therefrom using GENECLEAN II Kit (BIO101) in accordance with the instructions included in the kit. The DNA fragment thus purified was precipitated with ethanol and then dissolved in 20 μl of a solution containing 10 mM Tris-HCl (pH 7.4) and 1 mM EDTA. The resulting PCR reaction mixture was used for subcloning of the DNA fragment into plasmid pUC19 that had been digested with BamHI and HindIII, and subsequently the nucleotide sequence of the resulting plasmid was determined. A plasmid having the correct nucleotide sequence was designated "hMBCHv/pUC19."

(ii) Construction of H-Chain V-Region of Humanized H-Chain cDNA

To ligate to cDNA for humanized H-chain C-region Cγ1, the DNA for the humanized H-chain V-region constructed in the above step was modified by PCR method. For the PCR method, a backward primer MBC1HVS2 was designed to hybridize to the sequence encoding the 5' region of the leader sequence for the V-region and to have a Kozak consensus sequence (Kozak et al., J. Mol. Biol. 196, 947-950, 1987) and HindIII- and EcoRI-recognition sequences; and A forward primer MBC1HVR2 (SEQ ID NO: 10) for the H-chain V-region was designed to hybridize to a DNA sequence encoding the 3' region of the J region, to encode the 5' region of the C-region and to have ApaI- and SmaI-recognition sequences.

The PCR reaction was performed using TaKaRa Ex Taq (Takara Shuzo Co., Ltd.) and a buffer appended thereto. The PCR reaction solution comprised 0.4 μg of hMBCHv/pUC19 as a DNA template, 50 pmoles of each of MBC1HVS2 and MBC1HVR2 as primers, 2.5 U of TaKaRa Ex Taq and 0.25 mM dNTPs in the buffer. The PCR reaction was run for 30 cycles under the conditions: 94° C. for 1 min., 55° C. for 1 min. and 72° C. for 1 min. The DNA fragment thus amplified was separated by agarose gel electrophoresis on a 3% Nu Sieve GTG agarose (FMC Bio. Products).

A gel segment containing a DNA fragment of 456 bp was excised, and the DNA fragment was purified therefrom using GENECLEAN II Kit (BIO101) in accordance with the instructions included in the kit. The DNA fragment thus purified was precipitated with ethanol and then dissolved in 20 μl of a solution containing 10 mM Tris-HCl (pH 7.4) and 1 mM EDTA. The PCR reaction solution thus obtained was used for subcloning of the DNA fragment into plasmid pUC19 that had been digested with EcoRI and SmaI, and then the resulting plasmid was sequenced. As a result, a plasmid was obtained which contained a gene encoding mouse H-chain V-region derived from hybridoma #23-57-137-1 and also contained EcoRI- and HindIII-recognition sequences and a Kozak sequence on the 5' region and ApaI- and SmaI-recognition sequences on the 3' region, which was designated "hMBC1Hv/pUC19."

(2) Construction of Expression Vector for Humanized Antibody H-Chain

Plasmid RVh-PM1f-cDNA carrying a cDNA sequence for hPM1 antibody H-chain was digested with ApaI and BamHI to give a DNA fragment containing a DNA encoding the H-chain C-region. The DNA fragment was introduced into plasmid hMBC1Hv/pUC19 that had been digested with ApaI and BamHI. The obtained plasmid was designated "hMBC1HcDNA/pUC19." This plasmid contained both a DNA encoding the humanized #23-57-137-1 antibody H-chain V-region and a DNA encoding the human H-chain C-region Cγ1 and had EcoRI- and HindIII-recognition sequences on the 5' region and a BamHI-recognition sequence on the 3' region. The nucleotide sequence and the corresponding amino acid sequence of the humanized H-chain version "a" carried on the plasmid hMBC1HcDNA/pUC19 are shown in SEQ ID NO: 58 and SEQ ID NO: 56, respectively.

The plasmid hMBC1HcDNA/pUC19 was digested with EcoRI and BamHI to give a DNA fragment containing a DNA encoding the H-chain. The DNA fragment was introduced into expression plasmid pCOS1 that had been digested with EcoRI and BamHI. As a result, an expression plasmid for a humanized antibody was obtained, which was designated "hMBC1HcDNA/pCOS1."

To produce a plasmid used for expression in a CHO cell, plasmid hMBC1HcDNA/pUC19 was digested with EcoRI and BamHI to give a DNA fragment containing a DNA encoding the H-chain. The DNA fragment was introduced into expression vector pCHO1 that had been digested with EcoRI and BamHI. As a result, an expression plasmid for the humanized antibody was obtained, which was designated "hMBC1HcDNA/pCHO1."

(3) Construction of L-Chain Hybrid V-Region (i) Preparation of FR1,2/FR3,4 Hybrid Antibody A gene for the FR hybrid L-chain having both FRs from a humanized antibody and FRs from a mouse (chimeric) antibody was constructed, and evaluated each region for the humanization. In this step, a hybrid antibody having FR1 and FR2 both derived from a human antibody and FR3 and FR4 both derived from a mouse antibody was prepared by utilizing the AflII restriction site located on CDR2.

Plasmids MBC1L(λ)/neo and hMBC1L(λ)/neo (10 μg each) were separately digested in 100 μl of a reaction solution containing 10 mM Tris-HCl (pH 7.5), 10 mM MgCl$_2$, 1 mM DTT, 50 mM NaCl, 0.01% (w/v) of BSA and 10 U of AflII (Takara Shuzo Co., Ltd.) at 37° C. for 1 hour. The reaction solutions were subjected to electrophoresis on a 2% low-melting agarose gel, thereby giving DNA fragments of 6282 bp (referred to as "c1") and 1022 bp (referred to as "c2") from the plasmid MBC1L(λ)/neo or DNA fragments of 6282 bp (referred to as "h1") and 1022 bp (referred to as "h2") from the plasmid hMBC1L(λ)/neo. These DNA fragments were collected and purified from the gels using GENECLEAN II Kit (BIO101).

Each of the c1 and h1 fragments (1 µg each) was BAP-treated. The DNA fragment was extracted with phenol and chloroform, collected by ethanol precipitation, and then dissolved in 10 µl of a solution containing 10 mM Tris-HCl (pH 7.4) and 1 mM EDTA.

The BAP-treated c1 and h1 DNA fragments (1 µl each) were ligated to the h2 and c2 DNA fragments (4 µl each), respectively, (at 4° C. overnight). Each of the ligation products was introduced into a competent cell of *E. coli*, JM109, to form a transformant. The transformant was cultured in 2 ml of 2xYT medium containing 50 µg/ml of ampicillin. From the cell fraction, the plasmid was purified using QIAprep Spin Plasmid Kit (QIAGEN).

The purified plasmid was digested in 20 µl of a reaction solution containing 10 mM Tris-HCl (pH 7.5), 10 mM MgCl$_2$, 1 mM DTT, and either 2 U of ApaLI (Takara Shuzo Co., Ltd.) or 8 U of BamHI (Takara Shuzo Co., Ltd.) and HindIII (Takara Shuzo Co., Ltd.) at 37° C. for 1 hour. It was expected that if the c1-h2 was ligated correctly, this digestion reaction would give fragments of 5560/1246/498 bp (by the ApaLI digestion) or fragments of 7134/269 bp (by the BamHI/HindIII digestion). Based on this expectation, the desired plasmids were identified.

The expression vector encoding the human FR1,2/mouse FR3,4 hybrid antibody L-chain was designated "h/mMBC1L (λ)/neo." On the other hand, since a clone for the h1-c2 could not be obtained, recombination on a pUC vector was performed and then the resulting recombinant product was cloned into a HEF vector. In this procedure, plasmid hMBC1Laλ/pUC19, which contained DNA encoding a humanized antibody L-chain V-region without any amino acid replacements, and plasmid hMBC1Ldλ/pUC19, which contained a DNA encoding a humanized antibody L-chain V-region with an amino acid replacement at the 91-position amino acid tyrosine in FR3 (i.e., the 87th amino acid in accordance with The Kabat's prescription) by isoleucine, were used as templates.

Plasmids MBC1L(λ)/pUC19, hMBC1Laλ/pUC19 and hMBC1Ldλ/pUC19 (10 g each) were separately digested in 30 µl of a reaction solution containing 10 mM Tris-HCl (pH 7.5), 10 mM MgCl$_2$, 1 mM DTT, 50 mM NaCl, 0.01% (w/v) of BSA, 16 U of HindIII and 4 U of AflII at 37° C. for 1 hour. The reaction solutions were separately subjected to electrophoresis on a 2% low-melting agarose gel, thereby giving a DNA fragment of 215 bp from plasmid MBC1L(λ)/pUC19 (referred to as "c2'") and a DNA fragment of 3218 bp from each of plasmids hMBC1Laλ/pUC19 and hMBC1Ldλ/pUC19 (referred to as "ha1'" and "hd1'," respectively). These DNA fragments were collected and purified using GENECLEAN II Kit (BIO 101).

Each of the ha1' and hd1' fragments was ligated to the c2' fragment and then introduced into a competent cell of *E. coli*, JM109, to form a transformant. The transformant was cultured in 2 ml of 2xYT medium containing 50 µg/ml of ampicillin. From the cell fraction, the plasmid was purified using QIAprep Spin Plasmid Kit (QIAGEN). The plasmids thus prepared were designated "m/hMBC1Laλ/pUC19" for the ha1' fragment-containing plasmid and "m/hMBC1Ldλ/pUC19" for the hd1' fragment-containing plasmid.

Each of the plasmids m/hMBC1Laλ/pUC19 and m/hMBC1Ldλ/pUC19 was digested with EcoRI. The DNA fragment of 743 bp was electrophoresed on a 2% low-melting agarose gel, and then collected and purified therefrom using GENECLEAN II Kit (BIO101). The resulting DNA fragment was dissolved in 20 PI of a solution containing 10 mM Tris-HCl (pH 7.4) and 1 mM EDTA.

Each of the DNA fragments (4 µl each) was ligated to the above-obtained BAP-treated HEF vector (1 µl). The ligation product was introduced into a competent cell of *E. coli*, JM109, to form a transformant. The transformant was cultured in 2 ml of 2xYT medium containing 50 µg/ml of ampicillin. From the cell fraction, the plasmid was purified using QIAprep Spin Plasmid Kit (QIAGEN).

Each of the purified plasmids was digested in 20 µl of a reaction solution containing 20 mM Tris-HCl (pH 8.5), 10 mM MgCl$_2$, 1 mM DTT, 100 mM KCl, 8 U of HindIII (Takara Shuzo Co., Ltd.) and 2 U of PvuI (Takara Shuzo Co., Ltd.) at 37° C. for 1 hour. It was expected that if the DNA fragment was inserted in the plasmid in a correct orientation, this digestion would give digestion fragments of 5104/2195 bp, whereas if the DNA fragment is inserted in the plasmid in the reverse orientation, this digestion would give digestion fragments of 4378/2926 bp. The plasmid DNA was identified based on the expectation. The plasmids thus obtained were expression vectors encoding mouse FR1,2/human FR3,4 hybrid antibody L-chain, which were designated expression vectors "m/hMBC1Laλ/neo" and "m/hMBC1Ldλ/neo," respectively.

(ii) Preparation of FR1/FR2 Hybrid Antibody

An FR1/FR2 hybrid antibody was prepared in the same manner as set forth above utilizing a SnaBI restriction site located on CDR1.

Plasmids MBC1L(λ)/neo and h/mMBC1L(λ)/neo (10 µg each) were separately digested in 20 µl of a reaction solution containing 10 mM Tris-HCl (pH 7.9), 10 mM MgCl$_2$, 1 mM DTT, 50 mM NaCl, 0.01% (w/v) of BSA and 6 U of SnaBI (Takara Shuzo Co., Ltd.) at 37° C. for 1 hour. The resulting reaction solutions were further digested in 50 µl of a reaction solution containing 20 mM Tris-HCl (pH 8.5), 10 mM MgCl$_2$, 1 mM DTT, 100 mM KCl, 0.01% (w/v) of BSA and 6 U of PvuI at 37° C. for 1 hour.

The resulting reaction solutions were separately subjected to electrophoresis on a 1.5% low-melting agarose gel, thereby giving DNA fragments of 4955 bp (m1) and 2349 bp (m2) from the plasmid MBC1L(λ)/neo and DNA fragments of 4955 bp (hm1) and 2349 bp (hm2) from the plasmid h/mMBC1L(λ)/neo. These DNA fragments were collected and purified from the gels using GENECLEAN II Kit (BIO101). Each of the DNA fragments obtained was dissolved in 40 µl of a solution containing 10 mM Tris-HCl (pH 7.4) and 1 mM EDTA.

The m1 and hm1 fragments (1 µl each) were ligated to the hm2 and m2 fragments (4 µl each), respectively. Each of the resulting ligation products was introduced into a competent cell of *E. coli*, JM109, to form a transformant. The transformant obtained was cultured in 2 ml of 2xYT medium containing 50 µg/ml of ampicillin. From the cell fraction, the plasmid was purified using QIAprep Spin Plasmid Kit (QIAGEN).

Each of the purified plasmids was digested in 20 µl of a reaction solution containing 10 mM Tris-HCl (pH 7.5), 10 mM MgCl$_2$, 1 mM DTT and either 8 U of ApaI (Takara Shuzo Co., Ltd.) or 2 U of ApaLI (Takara Shuzo Co., Ltd.) at 37° C. for 1 hour.

It was expected that if the fragments were ligated correctly, the digestion reaction would give a fragment of 7304 bp (by the ApaI digestion) or fragments of 5560/1246/498 bp (by the ApaLI digestion) for m1-hm2, and would give fragments of 6538/766 bp (by the ApaI digestion) or fragments of 3535/2025/1246/498 bp (by the ApaLI digestion) for hm1-m2. Based on this expectation, the plasmids were identified. As a result, an expression vector encoding a human FR1/mouse FR2,3,4 hybrid antibody L-chain (designated "hmmMBC1L (λ)/neo") and an expression vector encoding a mouse FR1/human FR2/mouse FR3,4 hybrid antibody L-chain (designated "mhmMBC1L(λ)/neo") were obtained.

(4) Construction of Humanized Antibody L-Chain

A humanized #23-57-137-1 antibody L-chain was prepared by CDR-grafting technique by means of PCR method. For the preparation of a humanized #23-57-137-1 antibody L-chain (version "a") that contained FR1, FR2 and FR3 derived from human antibody HSU03868 (GEN-BANK, Deftos M. et al., Scand. J. Immunol., 39, 95-103, 1994) and FR4 derived from human antibody S25755 NBRF-PDB), six PCR primers were used.

The six primers were as follows: CDR-grafting primers MBC1LGP1 (SEQ ID NO: 29) and MBC1LGP3 (SEQ ID NO: 30), both having a sense DNA sequence, CDR-grafting primers MBC1LGP2 (SEQ ID NO: 31) and MBC1LGP4 (SEQ ID NO: 32), both having an antisense DNA sequence, all of which had a 15-21 bp complementary sequence on the both terminal ends; and external primers MBC1LVS1 (SEQ ID NO: 33) and MBC1LVR1 (SEQ ID NO: 34) having a homology to the CDR-grafting primers MBC1LGP1 and MBC1 LGP4, respectively.

The CDR-grafting primers MBC1LGP1, MBC1LGP2, MBC1LGP3 and MBC1LGP4 were separated on a urea-denatured polyacrylamide gel (Molecular Cloning: A Laboratory Manual, Sambrook et al., Cold Spring Harbor Laboratory Press, 1989) and extracted therefrom by crush-and-soak method (Molecular Cloning: A Laboratory Manual, Sambrook et al., Cold Spring Harbor Laboratory Press, 1989).

Each of the CDR-grafting primers (1 nmole each) was separated on a 6% denatured polyacrylamide gel. The identification of the DNA fragment of a desired length was performed on a silica gel thin plate by irradiation of UV ray. The desired DNA fragment was collected from the gel by crush-and-soak method. The collected DNA fragment was dissolved in 20 µl of a solution containing 10 mM Tris-HCl (pH 7.4) and 1 mM EDTA.

The PCR reaction was performed using TaKaRa Ex Taq (Takara Shuzo Co., Ltd.) and a buffer appended thereto. The PCR reaction solution comprised (per 100 µl) 1 µl of each of the CDR-grafting primers MBC1LGP1, MBC1LGP2, MBC1LGP3 and MBC1LGP4, 0.25 mM dNTPs, 2.5 U of TaKaRa Ex Taq in the buffer. The PCR reaction was run for 5 cycles under the conditions: 94° C. for 1 min., 55° C. for 1 min. and 72° C. for 1 min. The resulting reaction mixture was added with 50 pmoles of each of the external primers MBC1LVS1 and MBC1LVR1. Using this reaction mixture, the PCR reaction was run for additional 30 cycles under the same conditions. The DNA fragment thus amplified was separated by agarose gel electrophoresis on a 3% Nu Sieve GTG agarose (FMC Bio. Products).

An agarose segment containing a DNA fragment of 421 bp was excised, and the DNA fragment was purified therefrom using GENECLEAN II Kit (BIO101) in accordance with the instructions included in the kit. The PCR reaction mixture thus obtained was used for subcloning of the DNA fragment into plasmid pUC19 that had been digested with BamHI and HindIII. The resulting plasmid was sequenced. The plasmid thus prepared was designated "hMBCL/pUC19." In this plasmid, however, the 104-position amino acid (corresponding to the 96th amino acid in accordance with the Kabat's prescription) of CDR4 was replaced by arginine. For the correction of this amino acid to tyrosine, a correction primer MBC1LGP10R (SEQ ID NO: 35) was designed and synthesized. The PCR reaction was performed using TaKaRa Ex Taq (Takara Shuzo Co., Ltd.) and a buffer appended thereto. The PCR reaction solution comprised (per 100 µl) 0.6 µg of the plasmid hMBCL/pUC19 as a template DNA, 50 pmoles of each of the primers MBC1LVS1 and MBC1LGP10R, 2.5 U of TaKaRa Ex Taq (Takara Shuzo Co., Ltd.) and 0.25 mM dNTPs in the buffer, over which mineral oil (50 µl) was layered. The PCR reaction was run for 30 cycles under the conditions: 94° C. for 1 min., 55° C. for 1 min. and 72° C. for 1 min. The DNA fragment thus amplified was separated by agarose gel electrophoresis on a 3% Nu Sieve GTG agarose (FMC Bio. Products).

A gel segment containing a DNA fragment of 421 bp was excised, and the DNA fragment was purified therefrom using GENECLEAN II Kit (BIO 101) in accordance with the instructions included in the kit. The PCR reaction mixture thus prepared was used for subcloning of the DNA fragment into plasmid pUC19 that had been digested with BamHI and HindIII.

The plasmid was sequenced using M13 Primer M4 and M13 Primer RV. As a result, it was confirmed that the plasmid had the correct sequence. The plasmid was then digested with HindIII and BlnI, and a DNA fragment of 416 bp was separated by electrophoresis on a 1% agarose gel. The DNA fragment was purified using GENECLEAN II Kit (BIO101) in accordance with the instructions included in the kit, and then introduced into plasmid Cλ/pUC19 that had been digested with HindIII and BlnI. The resulting plasmid was designated "hMBC1Laλ/pUC19." This plasmid was digested with EcoRI to give a DNA fragment encoding humanized L-chain. The DNA fragment was introduced into plasmid pCOS1 so that the initiation codon for the humanized L-chain was located downstream to the EF1α promoter. The plasmid thus obtained was designated "hMBC1Laλ/pCOS1." The nucleotide sequence (including the corresponding amino acid sequence) of the humanized L-chain version "a" is shown in SEQ ID NO: 66. The amino acid sequence of the version "a" is also shown in SEQ ID NO: 47.

A humanized L-chain version "b" was prepared using mutagenesis by PCR method. The version "b" was designed such that the 43-position amino acid glycine (corresponding to the 43th amino acid in accordance with the Kabat's prescription) was replaced by proline and the 49-position amino acid lysine (corresponding to the 49th amino acid accordance with the Kabat's prescription) by aspartic acid in the version "a." The PCR reaction was performed using plasmid hMBC1Laλ/pUC19 as a template and a mutagenic primer MBC1LGP5R (SEQ ID NO: 36) and a primer MBC1LVS1. The DNA fragment obtained was digested with BamHI and HindIII, and the digestion fragment was subcloned into the BamHI-HindIII site of pUC19. After sequencing, the plasmid was digested with HindIII and AflII, and the resulting digestion fragment was ligated to plasmid hMBC1Laλ/pUC19 that had been digested with HindIII and AflII.

The plasmid thus obtained was designated "hMBC1Lbλ/pUC19." This plasmid was digested with EcoRI to give a DNA fragment containing a DNA encoding the humanized L-chain. The DNA fragment was introduced into plasmid pCOS1 such that the initiation codon for the humanized L-chain was located downstream to the EF1α promoter. The plasmid thus obtained was designated "hMBC1 Lbλ/pCOS1."

A humanized L-chain version "c" was prepared using mutagenesis by PCR method. The version "c" was designed such that the 84-position amino acid serine (corresponding to the 80th amino acid in accordance with the Kabat's prescription) was replaced by proline. The PCR reaction was performed using plasmid hMBC1Laλ/pUC19 as a template and a mutagenic primer MBC1LGP6S (SEQ ID NO: 37) and a primer M13 Primer RV. The DNA fragment obtained was digested with BamHI and HindIII and then subcloned into pUC19 that had been digested with BamHI and HindIII.

After sequencing, the plasmid was digested with BstPI and Aor51HI, and the resulting DNA fragment was ligated to plasmid hMBC1Laλ/pUC19 that had been digested with BstPI and Aor51HI. The plasmid thus obtained was designated "hMBC1Lcλ/pUC19." This plasmid was digested with EcoRI to give a DNA fragment containing a DNA encoding the humanized L-chain. The fragment was introduced into the EcoRI site of plasmid pCOS1 such that the initiation codon for the humanized L-chain was located downstream to the EF1α promoter. The plasmid thus obtained was designated "hMBC1Lcλ/pCOS1."

Humanized L-chain versions "d", "e" and "f" were also prepared using mutagenesis by PCR method. The versions "d", "e" and "f" were designed such that the 91-position amino acid tyrosine (corresponding to the 87th amino acid in accordance with the Kabat's prescription) was replaced by isoleucine in the versions "a", "b" and "c", respectively. For each of the versions "d", "e" and "f", a PCR reaction was performed using each of plasmid hMBC1Laλ/pCOS1 (for version "d"), hMBC1Lbλ/pCOS1 (for version "e") and hMBC1Lcλ/pCOS1 (for version "f"), respectively, as a template, a mutagenic primer MBC1LGP11R (SEQ ID NO: 38) and a primer M-S1 (SEQ ID NO: 44). The DNA fragment thus obtained was digested with BamHI and HindIII and then subcloned into pUC19 that had been digested with BamHI and HindIII. After sequencing, the plasmid was digested with HindIII and BlnI, and the resulting digestion fragment was ligated to plasmid Cλ/pUC19 that had been digested with HindIII and BlnI.

The plasmids thus obtained were respectively designated "hMBC1Ldλ/pUC19" (for version "d"), "hMBC1Leλ/pUC19" (for version "e") and "hMBC1Lfλ/pUC19" (for version "f"). Each of these plasmids was digested with EcoRI to give a DNA fragment containing a DNA encoding the humanized L-chain. The DNA fragment was introduced into the EcoRI site of plasmid pCOS1 such that the initiation codon for the humanized L-chain was located downstream to the EF1α promoter of the plasmid. The plasmids thus obtained were respectively designated "hMBC1Ldλ/pCOS1" (for version "d"), "hMBC1Leλ/pCOS1" (for version "e") and "hMBC1 Lfλ/pCOS1" (for version "f").

Humanized L-chain versions "g" and "h" were also prepared using mutagenesis by PCR method. The versions "g" and "h" were designed such that the 36-position amino acid histidine (corresponding to the 36th amino acid in accordance with the Kabat's prescription) was replaced by tyrosine in the versions "a" and "d", respectively. The PCR reaction was performed using a mutagenic primer MBC1LGP9R (SEQ ID NO: 39), M13 Primer RV and plasmid hMBC1Laλ/pUC19 as a template. An additional PCR was performed using the PCR product thus obtained and M13 Primer M4 as primers and plasmid hMBC1Laλ/pUC19 as a template. The DNA fragment obtained was digested with HindIII and BlnI and then subcloned into plasmid Cλ/pUC19 that had been digested with HindIII and BlnI. Using this plasmid as a template, a PCR reaction was performed using primers MBC1LGP13R (SEQ ID NO: 40) and MBC1LVS1. The PCR fragment obtained was digested with ApaI and HindIII and then introduced into either of plasmids hMBC1 Laλ/pUC19 and hMBC1Ldλ/pUC19 that had been digested with ApaI and HindIII. The plasmids obtained were sequenced. Plasmids that were confirmed to contain the correct sequence were designated "hMBC1Lgλ/pUC19" (for version "g") and "hMBC1Lhλ/pUC19" (for version "h"). Each of these plasmids was digested with EcoRI to give a DNA fragment containing a DNA encoding the humanized L-chain. The DNA fragment was introduced into the EcoRI site of plasmid pCOS1 such that the initiation codon for the humanized L-chain was located downstream to the EF1α promoter. The plasmids thus obtained were respectively designated "hMBC1Lgλ/pCOS1" (for version "g") and "hMBC1Lhλ/pCOS1" (for version "h").

Humanized L-chain versions "i", "j", "k", "l", "m", "n" and "o" were also prepared using mutagenesis by PCR method. The PCR reaction was performed using plasmid hMBC1Laλ/pUC19 as a template and a mutagenic primer MBC1LGP14S (SEQ ID NO: 41) and a primer V1RV (λ) (SEQ ID NO: 43). The resulting DNA fragment was digested with ApaI and BlnI and then subcloned into plasmid hMBC1Lgλ/pUC19 that had been digested with ApaI and BlnI. The plasmid obtained was sequenced, and the clone into which the mutation for each version was introduced was selected. The plasmid thus obtained was designated "hMBC1Lxλ/pUC19 (x=i, j, k, l, m, n or o)." This plasmid was digested with EcoRI to give a DNA fragment containing a DNA encoding the humanized L-chain. The DNA fragment was introduced into the EcoRI site of plasmid pCOS1 such that the initiation codon for the humanized L-chain was located downstream to the EF1α promoter. The plasmid thus obtained was designated "hMBC1Lxλ/pCOS1" (x=i, j, k, l, m, n or o). The DNA sequences (including the corresponding amino acid sequences) of the versions "j", "l", "m" and "o" are shown in SEQ ID NOs: 67, 68, 69 and 70, respectively. The amino acid sequences of these versions are also shown in SEQ ID NOs: 48, 49, 50 and 51, respectively.

Humanized L-chain versions "p", "q", "r", "s" and "t" were designed such that the 87-position amino acid (tyrosine) was replaced by isoleucine in the versions "i", "j", "m", "l" and "o", respectively. These versions were prepared utilizing an Aor51 MI restriction site on FR3 and replacing that site of each of the versions "i", "j", "m", "l" or "o" by that site of the version "h." That is, an Aor51HI restriction fragment (514 bp) containing CDR3, a part of FR3 and the entire FR4 were removed from an expression plasmid hMBC1Lxλ/pCOS1 (x=i, j, m, l or o). To the removed site, an Aor51HI restriction fragment (514 bp) in the expression plasmid hMBC1 Lhλ/pCOS, which containing CDR3 and a part of FR3 and the entire FR4, was ligated, so that the 91-position amino acid tyrosine (corresponding to the 87th amino acid in accordance with the Kabat's prescription) was replaced by isoleucine. The resulting plasmid was sequenced. A clone of each of the versions "i", "j", "m" "l" and "o" in which 91-position amino acid tyrosine (corresponding to the 87th amino acid in accordance with the Kabat's prescription) was replaced by isoleucine was selected. These modified versions respectively corresponding to the versions "i", "j", "m" "l" and "o" were designated versions "p", "q", "s", "r" and "t", respectively. The obtained plasmid was designated "hMBC1Lxλ/pCOS1 (x=p, q, s, r or t)." The DNA sequences (including the corresponding amino acids) of the versions "q", "r", "s" and "t" are shown in SEQ ID NOs: 71, 72, 73 and 74, respectively. The amino acid sequences of these versions are also shown in SEQ ID NOs: 52, 53, 54 and 55, respectively.

Plasmid hMBC1Lqλ/pCOS1 was digested with HindIII and EcoRI and then subcloned into plasmid pUC19 that had been digested with HindIII and EcoRI. The plasmid thus obtained was designated "hMBC1Lqλ/pUC19."

The positions of the replaced amino acids in the individual versions of the humanized L-chain are shown in Table 2 below.

TABLE 2

| Versions | 36 | 43 | 45 | 47 | 49 | 80 | 87 |
|---|---|---|---|---|---|---|---|
| a |   |   |   |   |   |   |   |
| b |   | P |   |   | D |   |   |
| c |   |   |   |   |   | P |   |
| d |   |   |   |   |   |   | I |
| e |   | P |   |   | D |   | I |
| f |   |   |   |   |   | P | I |
| g | Y |   |   |   |   |   |   |
| h | Y |   |   |   |   |   | I |
| i | Y |   | K |   |   |   |   |
| j | Y |   | K |   | D |   |   |
| k | Y |   | K | V |   |   |   |
| l | Y |   | K | V | D |   |   |
| m | Y |   |   |   | D |   |   |
| n | Y |   |   | V |   |   |   |
| o | Y |   |   | V | D |   |   |
| p | Y |   | K |   |   |   | I |
| q | Y |   | K |   | D |   | I |
| r | Y |   |   |   | D |   | I |
| s | Y |   | K | V | D |   | I |
| t | Y |   |   | V | D |   | I |

In Table 2, capital letters represent the following amino acids: Y: tyrosine; P: proline; K: lysine, V: valine; D: aspartic acid; and I: isoleucine.

E. coli strains each containing plasmids hMBC1HcDNA/pUC19 and hMBC1Lqλ/pUC19 were designated "*Escherichia coli* JM 109 (hMBC1HcDNA/pUC19)" and "*Escherichia coli* JM 109 (hMBC1Lqλ/pUC19)," respectively, which have been deposited under the terms of Budapest Treaty at the National Institute of Bioscience and Human-Technology, Agency of Industrial Science and Technology, Japan, (1-3, Higashi 1-chome, Tsukuba-shi, Ibaraki, Japan) on Aug. 15, 1996, under the accession No. FERM BP-5629 for *Escherichia coli* JM109 (hMBC1HcDNA/pUC19), and FERM BP-5630 for *Escherichia coli* JM109 (hMBC1Lqλ/pUC19).

(5) Transfection into COS-7 Cell

For the evaluation of the antigen-binding activity and the neutralizing activity of the hybrid antibodies and the humanized #23-57-137-1 antibodies, the above-prepared expression plasmids were expressed transiently in COS-7 cells.

For the transient expression of the L-chain hybrid antibodies, each of the following combinations of plasmids were co-transfected into a COS-7 cell by electroporation using Gene Pulser (Bio Rad): hMBC1HcDNA/pCOS1 and h/mMBC1L(λ)/neo; hMBC1HcDNA/pCOS1 and m/hMBC1Laλ/neo; hMBC1HcDNA/pCOS1 and m/hMBC1Ldλ/neo; hMBC1HcDNA/pCOS1 and hmmMBC1L(λ)/neo; and hMBC1HcDNA/pCOS1 and mhmMBC1L(λ)/neo. That is, a cell suspension (0.8 ml) of COS-7 cells in PBS(−) (1×10$^7$ cells/ml) was added with each combination of the plasmid DNAs (10 μg each). The resulting solution was applied with pulses at an electrostatic capacity of 1,500V and 25 PF. After 10 min. of recovery period at room temperature, the electroporated cells were suspended in DMEM medium containing 2% Ultra Low IgG fetal calf serum (GIBCO), and then cultured using a 10-cm culture dish in a $CO_2$ incubator. After culturing for 72 hours, a culture supernatant was collected and centrifuged to remove cell debris. The solutions thus prepared were provided for use in the ELISA below.

For the transient expression of the humanized #23-57-137-1 antibodies, plasmids of hMBC1HcDNA/pCOS1 and hMBC1Lxλ/pCOS1 (x=a–t) were co-transfected into a COS-7 cell using Gene Pulser (Bio Rad) in the same manner as described for the hybrid antibodies above. The culture supernatants were prepared and provided for use in the ELISA below.

The purification of the hybrid antibodies and the humanized antibodies from the COS-7 cell culture supernatants was performed using AffiGel Protein A MAPSII Kit (Bio Rad) in accordance with the instructions included in the kit.

(6) ELISA (i) Determination of Antibody Concentration

An ELISA plate for determining antibody concentration was prepared as follows. Each well of a 96-well ELISA plate (Maxisorp, NUNC) was coated with 100 μl of a coating buffer (0.1 M $NaHCO_3$, 0.02% $NaN_3$) containing 1 μg/ml of goat anti-human IgG antibody (TAGO) and then blocked with 200 μl of a dilution buffer [50 mM Tris-HCl, 1 mM $MgCl_2$, 0.1 M NaCl, 0.05% Tween 20, 0.02% $NaN_3$, 1% bovine serum albumin (BSA); pH 7.2]. Each of the wells was added with each of the serial dilutions of the COS-7 cell culture supernatant in which each of the hybrid antibodies and the humanized antibodies was expressed, or added with each of the serial dilutions of each of the hybrid antibodies and humanized antibodies in a purified form. The plate was incubated at room temperature for 1 hour and washed with PBS-Tween 20. Subsequently, each of the wells was added with 100 μl of alkaline phosphatase-conjugated goat anti-human IgG antibody (TAGO). The plate was incubated at room temperature for 1 hour and washed with PBS-Tween 20. Subsequently, each of the wells was added with 1 mg/ml of a substrate solution ("Sigma 104"; p-nitrophenylphosphoric acid, SIGMA). The solution in each well was measured on its absorbance at 405 nm using Microplate Reader (Bio Rad) to determine the antibody concentration. In this determination, Hu IgG1λ Purified (The Binding Site) was used as the standard substance.

(ii) Determination of Antigen-Binding Ability

An ELISA plate for determining antigen-binding ability was prepared as follows. Each well of a 96-well ELISA plate was coated with 100 μl of a coating buffer containing 1 μg/ml of human PTHrP (1-34) and then blocked with 200 μl of a dilution buffer. Subsequently, each well was added with each of the serial dilutions of the COS-7 cell culture supernatant in which each of the hybrid antibodies and humanized antibodies was expressed, or added with each of the serial dilutions of each of the hybrid antibodies and humanized antibodies in a purified form. The plate was incubated at room temperature and washed with PBS-Tween 20. Subsequently, each well was added with 100 μl of alkaline phosphatase-conjugated goat anti-human IgG antibody (TAGO). The plate was incubated at room temperature and washed with PBS-Tween 20. Subsequently, each well was added with 1 mg/ml of a substrate solution ("Sigma 104"; p-nitrophenylphosphoric acid, SIGMA). The solution was measured on its absorbance at 405 nm using Microplate Reader (Bio Rad).

(7) Confirmation of Activities (i) Evaluation of Humanized H-Chain

It was found that an antibody having both a humanized H-chain version "a" and a chimeric L-chain exhibited the same level of PTHrP-binding activity as that of a chimeric antibody. This result suggests that the version "a" achieves the humanization of the H-chain V-region in the degree enough to evaluate the humanization. Therefore, the humanized H-chain version "a" was provided for use as a humanized antibody H-chain in the following experiments.

(ii) Activity of Hybrid Antibodies (ii-a) FR1,2/FR3,4 Hybrid Antibody

When the L-chain was h/mMBC1L(λ), no antigen-binding activity was observed. In contrast, when the L-chain was either m/hMBC1Laλ or m/hMBC1Ldλ, the same level of antigen-binding activity as that of the chimeric #23-57-137-1 antibody was observed. These results suggest that FR3 and FR4 have no problem as humanized antibodies but FR1 and FR2 contain amino acid residue(s) that need to be replaced.

(ii-b) FR1/FR2 Hybrid Antibody

When the L-chain was mhmMBC1L(λ), no antigen-binding activity was observed. In contrast, when the L-chain was hmmMBC1L(λ), the same level of antigen-binding activity as that of the chimeric #23-57-137-1 antibody was observed. These results suggest that FR1 has no problem as a humanized antibody but FR2 contains amino acid residue(s) that need to be replaced.

(iii) Activity of Humanized Antibodies

The antigen-binding activity of the humanized antibodies having the L-chain versions "a" to "t", respectively, were determined. As a result, it was found that the humanized antibodies having the L-chain versions "j", "l", "m", "o", "q", "r", "s" and "t" exhibited the same levels of PTHrP-binding activity as that of the chimeric antibody.

(8) Establishment of CHO Cell Line Capable of Stable Production of Antibody

For establishing a cell line capable of stable production of humanized antibodies, each of the above-prepared expression plasmids was introduced into a CHO cell (DXB11).

That is, the establishment of a cell line capable of stable production of a humanized antibody was performed using each of the following combinations of plasmids as expression vectors for a CHO cell: hMBC1HcDNA/pCHO1 and hMBC1Lmλ/pCOS1; hMBC1HcDNA/pCHO1 and hMBC1Lqλ/pCOS1; and hMBC1HcDNA/pCHO1 and hMBC1Lrλ/pCOS1. The plasmids were co-transfected into a CHO cell by electroporation using Gene Pulser (Bio Rad). Subsequently, the expression vectors were separately cleaved with restriction enzyme PvuI to give linear DNA fragments. The resulting DNA fragments were extracted with phenol and chloroform and then precipitated with ethanol. The DNA fragments thus prepared were used in the subsequent electroporation. That is, the plasmid DNA fragments (10 μg each) were added to 0.8 ml of a cell suspension of CHO cells in PBS(−) (1×10$^7$ cells/ml). The resulting solution was applied with pulses at an electrostatic capacity of 1,500V and 25 μF. After 10 min. of recovery period at room temperature, the cells thus treated were suspended in MEM-A medium (GIBCO) containing 10% fetal calf serum (GIBCO), and then cultured in a $CO_2$ incubator using 96-well plates (Falcon). On the day following the culturing being started, the medium was replaced by ribonucleoside- or deoxyribonucleoside-free MEM-α selective medium containing 10% fetal calf serum (GIBCO) and 500 mg/ml of GENETICIN (G418Sulfate; GIBCO). From the culture medium, cells into which the antibody gene was introduced were selected. The culture medium was replaced by a fresh one. About two weeks after the medium replacement, the cells were observed microscopically. When a satisfactory cell growth was observed, the amount of the antibodies produced was determined by conventional ELISA for determination of antibody concentration as set forth above. Among the cells, those cells which produced a larger amount of antibodies were screened.

The culturing of the established cell line capable of stable production of antibodies was scaled up in a roller bottle using a ribonucleoside- or deoxyribonucleoside-free MEM-α medium containing 2% Ultra Low IgG fetal calf serum. On each of day 3 or day 4 of the culturing, the culture supernatant was collected and filtered on a 0.2-μm filter (Millipore) to remove cell debris therefrom.

The purification of the humanized antibodies from the culture supernatant of the CHO cells was performed using POROS Protein A Column (PerSeptive Biosystems) on Con-Sep LC100 (Millipore) in accordance with the instructions included in the kit. The humanized antibodies were provided for use in the determination of neutralizing activity and pharmacological test in hypercalcemic model animals. The concentration and the antigen-binding activity of the purified humanized antibodies were determined by the ELISA system as set forth above.

Reference Example 5

Determination of Neutralizing Activity

The determination of neutralizing activity of the mouse antibodies, the chimeric antibodies and the humanized antibodies was performed using rat myeloma cell line ROS17/2.8-5 cells. The ROS17/2.8-5 cells were cultured in Ham'S F-12 medium (GIBCO) containing 10% fetal calf serum (GIBCO) in a $CO_2$ incubator. The ROS17/2.8-5 cells were seeded into each well of a 96-well plate at a density of $10^4$ cells/100 μl/well and cultured for one day. After the culturing was completed, the culture medium was replaced by Ham'S F-12 medium (GIBCO) containing 4 mM Hydrocortisone and 10% fetal calf serum. After culturing for three to four days, the cultured cells were washed with 260 μl of Ham'S F-12 medium (GIBCO), and then added with 80 μl of Ham's F-12 medium containing 1 mM isobutyl-1-methyl xanthine (IBMX, SIGMA), 10% fetal calf serum and 10 mM HEPES. The resulting mixture was incubated at 37° C. for 30 min.

The culture mediums of the mouse antibodies, the chimeric antibodies and the humanized antibodies to be tested for neutralizing activity were previously diluted serially in the following dilution series: [10 μg/ml, 3.3 μg/ml, 1.1 μg/ml and 0.37 μg/ml], [10 μg/ml, 2 μg/ml, 0.5 μg/ml and 0.01 μg/ml] and [10 μg/ml, 5 μg/ml, 1.25 μg/ml, 0.63 μg/ml and 0.31 μg/ml]. Each of the diluted antibody sample solutions was mixed with an equivalent amount of 4 ng/ml of PTHrP (1-34). The resulting mixed solution (80 μl) was added to each well. In each well, the final concentration of each antibody became a quarter of the above-mentioned concentration of the antibody, and accordingly the concentration of PTHrP (1-34) became 1 ng/ml. After the treatment at room temperature for 10 min., the culture supernatant was removed and the residue was washed with PBS three times. Subsequently, cAMP in the cells was extracted with 100 μl of a 0.3% HCl-95% ethanol and then evaporated using a water jet aspirator to remove the HCl-ethanol. The residue was dissolved in 120 μl of EIA buffer included in cAMP EIA Kit (CAYMAN CHEMICAL'S) to extract the cAMP therefrom. The cAMP was determined using cAMP EIA Kit (CAYMAN CHEMICAL'S) in accordance with the instructions included in the kit. As a result, it was found that, among the humanized antibodies having the same levels of antigen-binding activity as that of the chimeric antibody, those antibodies having L-chain versions "q", "r", "s" and "t" (in which the 91-position tyrosine was replaced by isoleucine) exhibited the similar neutralizing activity to that of the chimeric antibody, and that antibody having a L-chain version "q" exhibited the strongest neutralizing activity.

All publications, patents and patent applications cited herein are incorporated by reference in their entirety.

INDUSTRIAL APPLICABILITY

As described above, the present invention provides an agent for ameliorating low vasopressin level, which comprises, as an active ingredient, a substance capable of inhibiting the binding between parathyroid hormone-related peptide and a receptor thereof. The present invention also provides an agent for ameliorating a symptom caused by a decrease in vasopressin level, which comprises, as an active ingredient, a substance capable of inhibiting the binding between parathyroid hormone-related peptide and a receptor thereof.

In view of the fact that when administered to a model animal with low vasopressin level, the above substance induces the amelioration of blood vasopressin level and a symptom of polyuria in the model animal, the substance is found to be useful as an ameliorating agent for low vasopressin level.

The invention claimed is:

1. A method of treating hyperosmolarity caused by a decrease in vasopressin level in blood comprising administering to a patient at least one humanized anti-parathyroid hormone related protein 1-34 (anti-PTHrP (1-34)) antibody, or a binding fragment thereof that binds to SEQ ID NO: 75 in an amount sufficient to inhibit the decrease in vasopressin level in the blood of the patient, wherein said at least one humanized anti-parathyroid hormone related protein 1-34 (anti-PTHrP (1-34)) antibody, or binding fragment thereof comprises a heavy chain variable region comprising the amino acid sequence of SEQ ID NO: 56 and a light chain variable region comprising the amino acid sequence selected from the group consisting of SEQ ID NO: 47, 48, 49, 50, 51, 52, 53, 54 and 55.

2. The method according to claim 1, wherein the decrease in vasopressin level results from cancer.

3. The method according to claim 1, wherein the binding fragment is Fab, scFv, F(ab')₂ or Fv.

4. The method according to claim 1, wherein the antibody is a monoclonal antibody.

* * * * *

UNITED STATES PATENT AND TRADEMARK OFFICE
CERTIFICATE OF CORRECTION

| | | |
|---|---|---|
| PATENT NO. | : 7,655,227 B1 | Page 1 of 1 |
| APPLICATION NO. | : 10/019501 | |
| DATED | : February 2, 2010 | |
| INVENTOR(S) | : Etsuro Ogata et al. | |

It is certified that error appears in the above-identified patent and that said Letters Patent is hereby corrected as shown below:

Title Page; please insert;

-- (30)           Foreign Application Priority Data

July 2, 1999     (JP)...............................................11/189322 --

Signed and Sealed this
Twenty-second Day of February, 2011

David J. Kappos
*Director of the United States Patent and Trademark Office*

SEQUENCE LISTING

```
<160> NUMBER OF SEQ ID NOS: 75

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA

<400> SEQUENCE: 1
aaatagccct tgaccaggca                                                   20

<210> SEQ ID NO 2
<211> LENGTH: 38
<212> TYPE: DNA
<213> ORGANISM: Artificial Sequence
<220> FEATURE:
<223> OTHER INFORMATION: Synthetic DNA

<400> SEQUENCE: 2
ctggttcggc ccacctctga aggttccaga atcgatag                               38

<210> SEQ ID NO 3
<211> LENGTH: 28
<212> TYPE: DNA
<213> ORGANISM: Artificial Sequence
<220> FEATURE:
<223> OTHER INFORMATION: Synthetic DNA

<400> SEQUENCE: 3
ggatcccggg ccagtggata gacagatg                                          28

<210> SEQ ID NO 4
<211> LENGTH: 29
<212> TYPE: DNA
<213> ORGANISM: Artificial Sequence
<220> FEATURE:
<223> OTHER INFORMATION: Synthetic DNA

<400> SEQUENCE: 4
ggatcccggg tcagrggaag gtggraaca                                         29

<210> SEQ ID NO 5
<211> LENGTH: 17
<212> TYPE: DNA
<213> ORGANISM: Artificial Sequence
<220> FEATURE:
<223> OTHER INFORMATION: Synthetic DNA

<400> SEQUENCE: 5
```
gttttcccag tcacgac                                                  17

<210> SEQ ID NO 6
<211> LENGTH: 17
<212> TYPE: DNA
<213> ORGANISM: Artificial Sequence
<220> FEATURE:
<223> OTHER INFORMATION: Synthetic DNA

<400> SEQUENCE: 6
caggaaacag ctatgac                                                  17

<210> SEQ ID NO 7
<211> LENGTH: 31
<212> TYPE: DNA
<213> ORGANISM: Artificial Sequence
<220> FEATURE:
<223> OTHER INFORMATION: Synthetic DNA

<400> SEQUENCE: 7
gtctaagctt ccaccatgaa acttcgggct c                                  31

<210> SEQ ID NO 8
<211> LENGTH: 30
<212> TYPE: DNA
<213> ORGANISM: Artificial Sequence
<220> FEATURE:
<223> OTHER INFORMATION: Synthetic DNA

<400> SEQUENCE: 8
tgttggatcc ctgcagagac agtgaccaga                                    30

<210> SEQ ID NO 9
<211> LENGTH: 36
<212> TYPE: DNA
<213> ORGANISM: Artificial Sequence
<220> FEATURE:
<223> OTHER INFORMATION: Synthetic DNA

<400> SEQUENCE: 9
gtctgaattc aagcttccac catggggttt gggctg                             36

<210> SEQ ID NO 10
<211> LENGTH: 41
<212> TYPE: DNA
<213> ORGANISM: Artificial Sequence
<220> FEATURE:
<223> OTHER INFORMATION: Synthetic DNA

<400> SEQUENCE: 10
tttcccgggc ccttggtgga ggctgaggag acggtgacca g                       41

<210> SEQ ID NO 11
<211> LENGTH: 109
<212> TYPE: DNA
<213> ORGANISM: Artificial Sequence
<220> FEATURE:
<223> OTHER INFORMATION: Synthetic DNA

<400> SEQUENCE: 11
gtctgaattc aagcttagta cttggccagc ccaaggccaa ccccacggtc accctgttcc   60
cgccctcctc tgaggagctc aagccaaca aggccacact agtgtgtct               109

<210> SEQ ID NO 12

```
<211> LENGTH: 110
<212> TYPE: DNA
<213> ORGANISM: Artificial Sequence
<220> FEATURE:
<223> OTHER INFORMATION: Synthetic DNA

<400> SEQUENCE: 12
ggtttggtgg tctccactcc cgccttgacg gggctgccat ctgccttcca ggccactgtc    60
acagctcccg ggtagaagtc actgatcaga cacactagtg tggccttgtt             110

<210> SEQ ID NO 13
<211> LENGTH: 98
<212> TYPE: DNA
<213> ORGANISM: Artificial Sequence
<220> FEATURE:
<223> OTHER INFORMATION: Synthetic DNA

<400> SEQUENCE: 13
ggagtggaga ccaccaaacc ctccaaacag agcaacaaca agtacgcggc cagcagctac    60
ctgagcctga cgcccgagca gtggaagtcc cacagaag                           98

<210> SEQ ID NO 14
<211> LENGTH: 106
<212> TYPE: DNA
<213> ORGANISM: Artificial Sequence
<220> FEATURE:
<223> OTHER INFORMATION: Synthetic DNA

<400> SEQUENCE: 14
tgttgaattc ttactatgaa cattctgtag gggccactgt cttctccacg gtgctccctt    60
catgcgtgac ctggcagctg tagcttctgt gggacttcca ctgctc                 106

<210> SEQ ID NO 15
<211> LENGTH: 43
<212> TYPE: DNA
<213> ORGANISM: Artificial Sequence
<220> FEATURE:
<223> OTHER INFORMATION: Synthetic DNA

<400> SEQUENCE: 15
gtctgaattc aagcttagta cttggccagc ccaaggccaa ccc                     43

<210> SEQ ID NO 16
<211> LENGTH: 20
<212> TYPE: DNA
<213> ORGANISM: Artificial Sequence
<220> FEATURE:
<223> OTHER INFORMATION: Synthetic DNA

<400> SEQUENCE: 16
tgttgaattc ttactatgaa                                               20

<210> SEQ ID NO 17
<211> LENGTH: 39
<212> TYPE: DNA
<213> ORGANISM: Artificial Sequence
<220> FEATURE:
<223> OTHER INFORMATION: Synthetic DNA

<400> SEQUENCE: 17
caacaagtac gcggccagca gctacctgag cctgacgcc                          39

<210> SEQ ID NO 18
<211> LENGTH: 39
```

<212> TYPE: DNA
<213> ORGANISM: Artificial Sequence
<220> FEATURE:
<223> OTHER INFORMATION: Synthetic DNA

<400> SEQUENCE: 18
gtagctgctg gccgcgtact tgttgttgct ctgtttgga                              39

<210> SEQ ID NO 19
<211> LENGTH: 46
<212> TYPE: DNA
<213> ORGANISM: Artificial Sequence
<220> FEATURE:
<223> OTHER INFORMATION: Synthetic DNA

<400> SEQUENCE: 19
gtctgaattc aagcttagtc ctaggtcgaa ctgtggctgc accatc                      46

<210> SEQ ID NO 20
<211> LENGTH: 34
<212> TYPE: DNA
<213> ORGANISM: Artificial Sequence
<220> FEATURE:
<223> OTHER INFORMATION: Synthetic DNA

<400> SEQUENCE: 20
tgttgaattc ttactaacac tctccctgt tgaa                                    34

<210> SEQ ID NO 21
<211> LENGTH: 35
<212> TYPE: DNA
<213> ORGANISM: Artificial Sequence
<220> FEATURE:
<223> OTHER INFORMATION: Synthetic DNA

<400> SEQUENCE: 21
gtctaagctt ccaccatggc ctggactcct ctctt                                  35

<210> SEQ ID NO 22
<211> LENGTH: 48
<212> TYPE: DNA
<213> ORGANISM: Artificial Sequence
<220> FEATURE:
<223> OTHER INFORMATION: Synthetic DNA

<400> SEQUENCE: 22
tgttgaattc agatctaact acttacctag gacagtgacc ttggtccc                    48

<210> SEQ ID NO 23
<211> LENGTH: 128
<212> TYPE: DNA
<213> ORGANISM: Artificial Sequence
<220> FEATURE:
<223> OTHER INFORMATION: Synthetic DNA

<400> SEQUENCE: 23
gtctaagctt ccaccatggg gtttgggctg agctgggttt tcctcgttgc tcttttaaga       60
ggtgtccagt gtcaggtgca gctggtggag tctgggggag gcgtggtcca gcctgggagg     120
tccctgag                                                              128

<210> SEQ ID NO 24
<211> LENGTH: 125
<212> TYPE: DNA
<213> ORGANISM: Artificial Sequence
<220> FEATURE:

```
<223> OTHER INFORMATION: Synthetic DNA

<400> SEQUENCE: 24
accattagta gtggtggtag ttacacctac tatccagaca gtgtgaaggg gcgattcacc      60
atctccagag acaattccaa gaacacgctg tatctgcaaa tgaacagcct gagagctgag     120
gacac                                                                 125

<210> SEQ ID NO 25
<211> LENGTH: 132
<212> TYPE: DNA
<213> ORGANISM: Artificial Sequence
<220> FEATURE:
<223> OTHER INFORMATION: Synthetic DNA

<400> SEQUENCE: 25
ctaccaccac tactaatggt tgccacccac tccagcccct tgcctggagc ctggcggacc      60
caagacatgc catagctact gaaggtgaat ccagaggctg cacaggagag tctcaggac      120 ctcccaggct gg                                                         132

<210> SEQ ID NO 26
<211> LENGTH: 110
<212> TYPE: DNA
<213> ORGANISM: Artificial Sequence
<220> FEATURE:
<223> OTHER INFORMATION: Synthetic DNA

<400> SEQUENCE: 26
tgttggatcc ctgaggagac ggtgaccagg gttccctggc cccagtaagc aaagtaagtc      60
atagtagtct gtctcgcaca gtaatacaca gccgtgtcct cagctctcag                110

<210> SEQ ID NO 27
<211> LENGTH: 30
<212> TYPE: DNA
<213> ORGANISM: Artificial Sequence
<220> FEATURE:
<223> OTHER INFORMATION: Synthetic DNA

<400> SEQUENCE: 27
gtctaagctt ccaccatggg gtttgggctg                                       30

<210> SEQ ID NO 28
<211> LENGTH: 30
<212> TYPE: DNA
<213> ORGANISM: Artificial Sequence
<220> FEATURE:
<223> OTHER INFORMATION: Synthetic DNA

<400> SEQUENCE: 28
tgttggatcc ctgaggagac ggtgaccagg                                       30

<210> SEQ ID NO 29
<211> LENGTH: 133
<212> TYPE: DNA
<213> ORGANISM: Artificial Sequence
<220> FEATURE:
<223> OTHER INFORMATION: Synthetic DNA

<400> SEQUENCE: 29
acaaagcttc caccatggcc tggactcctc tcttcttctt ctttgttctt cattgctcag      60
gttcttcctc ccagcttgtg ctgactcaat cgccctctgc ctctgcctcc ctgggagcct     120
cggtcaagct cac                                                        133
```

<210> SEQ ID NO 30
<211> LENGTH: 118
<212> TYPE: DNA
<213> ORGANISM: Artificial Sequence
<220> FEATURE:
<223> OTHER INFORMATION: Synthetic DNA

<400> SEQUENCE: 30

```
agcaagatgg aagccacagc acaggtgatg ggattcctga tcgcttctca ggctccagct    60
ctggggctga gcgctacctc accatctcca gcctccagtc tgaggatgag gctgacta    118
```

<210> SEQ ID NO 31
<211> LENGTH: 128
<212> TYPE: DNA
<213> ORGANISM: Artificial Sequence
<220> FEATURE:
<223> OTHER INFORMATION: Synthetic DNA

<400> SEQUENCE: 31

```
ctgtggcttc catcttgctt aagtttcatc aagtaccgag ggcccttctc tggctgctgc    60
tgatgccatt caatggtgta cgtactgtgc tgactactca aggtgcaggt gagcttgacc   120
gaggctcc                                                            128
```

<210> SEQ ID NO 32
<211> LENGTH: 114
<212> TYPE: DNA
<213> ORGANISM: Artificial Sequence
<220> FEATURE:
<223> OTHER INFORMATION: Synthetic DNA

<400> SEQUENCE: 32

```
cttggatccg ggctgaccta ggacggtcag tttggtccct ccgccgaaca ccctcacaaa    60
ttgttcctta attgtatcac ccacaccaca gtaatagtca gcctcatcct caga          114
```

<210> SEQ ID NO 33
<211> LENGTH: 17
<212> TYPE: DNA
<213> ORGANISM: Artificial Sequence
<220> FEATURE:
<223> OTHER INFORMATION: Synthetic DNA

<400> SEQUENCE: 33

```
acaaagcttc caccatg                                                   17
```

<210> SEQ ID NO 34
<211> LENGTH: 19
<212> TYPE: DNA
<213> ORGANISM: Artificial Sequence
<220> FEATURE:
<223> OTHER INFORMATION: Synthetic DNA

<400> SEQUENCE: 34

```
cttggatccg ggctgacct                                                 19
```

<210> SEQ ID NO 35
<211> LENGTH: 75
<212> TYPE: DNA
<213> ORGANISM: Artificial Sequence
<220> FEATURE:
<223> OTHER INFORMATION: Synthetic DNA

<400> SEQUENCE: 35
cttggatccg ggctgaccta ggacggtcag tttggtccct ccgccgaaca cgtacacaaa     60
ttgttcctta attgt                                                      75

<210> SEQ ID NO 36
<211> LENGTH: 43
<212> TYPE: DNA
<213> ORGANISM: Artificial Sequence
<220> FEATURE:
<223> OTHER INFORMATION: Synthetic DNA

<400> SEQUENCE: 36
aaaggatcct taagatccat caagtaccga gggggcttct ctg                       43

<210> SEQ ID NO 37
<211> LENGTH: 46
<212> TYPE: DNA
<213> ORGANISM: Artificial Sequence
<220> FEATURE:
<223> OTHER INFORMATION: Synthetic DNA

<400> SEQUENCE: 37
acaaagctta gcgctacctc accatctcca gcctccagcc tgagga                    46

<210> SEQ ID NO 38
<211> LENGTH: 111
<212> TYPE: DNA
<213> ORGANISM: Artificial Sequence
<220> FEATURE:
<223> OTHER INFORMATION: Synthetic DNA

<400> SEQUENCE: 38
cttggatccg ggctgaccta ggacggtcag tttggtccct ccgccgaaca cgtacacaaa     60
ttgttcctta attgtatcac ccacaccaca gatatagtca gcctcatcct c              111

<210> SEQ ID NO 39
<211> LENGTH: 42
<212> TYPE: DNA
<213> ORGANISM: Artificial Sequence
<220> FEATURE:
<223> OTHER INFORMATION: Synthetic DNA

<400> SEQUENCE: 39
cttctctggc tgctgctgat accattcaat ggtgtacgta ct                        42

<210> SEQ ID NO 40
<211> LENGTH: 26
<212> TYPE: DNA
<213> ORGANISM: Artificial Sequence
<220> FEATURE:
<223> OTHER INFORMATION: Synthetic DNA

<400> SEQUENCE: 40
cgagggccct tctctggctg ctgctg                                          26

<210> SEQ ID NO 41
<211> LENGTH: 35
<212> TYPE: DNA
<213> ORGANISM: Artificial Sequence
<220> FEATURE:
<223> OTHER INFORMATION: Synthetic DNA

<400> SEQUENCE: 41
gagaagggcc ctargtacst gatgrawctt aagca                                35

```
<210> SEQ ID NO 42
<211> LENGTH: 35
<212> TYPE: DNA
<213> ORGANISM: Artificial Sequence
<220> FEATURE:
<223> OTHER INFORMATION: Synthetic DNA

<400> SEQUENCE: 42
cacgaattca ctatcgattc tggaaccttc agagg                              35

<210> SEQ ID NO 43
<211> LENGTH: 18
<212> TYPE: DNA
<213> ORGANISM: Artificial Sequence
<220> FEATURE:
<223> OTHER INFORMATION: Synthetic DNA

<400> SEQUENCE: 43
ggcttggagc tcctcaga                                                 18

<210> SEQ ID NO 44
<211> LENGTH: 20
<212> TYPE: DNA
<213> ORGANISM: Artificial Sequence
<220> FEATURE:
<223> OTHER INFORMATION: Synthetic DNA

<400> SEQUENCE: 44
gacagtggtt caaagttttt                                               20

<210> SEQ ID NO 45
<211> LENGTH: 118
<212> TYPE: PRT
<213> ORGANISM: Mus musculus

<400> SEQUENCE: 45

Gln Leu Val Leu Thr Gln Ser Ser Ser Ala Ser Phe Ser Leu Gly Ala
  1               5                  10                  15

Ser Ala Lys Leu Thr Cys Thr Leu Ser Ser Gln His Ser Thr Tyr Thr
             20                  25                  30

Ile Glu Trp Tyr Gln Gln Pro Leu Lys Pro Pro Lys Tyr Val Met
         35                  40                  45

Asp Leu Lys Gln Asp Gly Ser His Ser Thr Gly Asp Gly Ile Pro Asp
     50                  55                  60

Arg Phe Ser Gly Ser Ser Ser Gly Ala Asp Arg Tyr Leu Ser Ile Ser
 65                  70                  75                  80

Asn Ile Gln Pro Glu Asp Glu Ala Met Tyr Ile Cys Gly Val Gly Asp
             85                  90                  95

Thr Ile Lys Glu Gln Phe Val Tyr Val Phe Gly Gly Gly Thr Lys Val
        100                 105                 110

Thr Val Leu Gly Gln Pro
        115

<210> SEQ ID NO 46
<211> LENGTH: 118
<212> TYPE: PRT
<213> ORGANISM: Mus musculus

<400> SEQUENCE: 46

Glu Val Gln Leu Val Glu Ser Gly Gly Asp Leu Val Lys Pro Gly Gly
  1               5                  10                  15

Ser Leu Lys Leu Ser Cys Ala Ala Ser Gly Phe Thr Phe Ser Ser Tyr
```

```
                        20                  25                  30
Gly Met Ser Trp Ile Arg Gln Thr Pro Asp Lys Arg Leu Glu Trp Val
                35                  40                  45
Ala Thr Ile Ser Ser Gly Gly Ser Tyr Thr Tyr Tyr Pro Asp Ser Val
         50                  55                  60
Lys Gly Arg Phe Thr Ile Ser Arg Asp Asn Ala Lys Asn Thr Leu Tyr
 65                  70                  75                  80
Leu Gln Met Ser Ser Leu Lys Ser Glu Asp Thr Ala Met Phe Tyr Cys
                 85                  90                  95
Ala Arg Gln Thr Thr Met Thr Tyr Phe Ala Tyr Trp Gly Gln Gly Thr
                100                 105                 110
Leu Val Thr Val Ser Ala
            115

<210> SEQ ID NO 47
<211> LENGTH: 116
<212> TYPE: PRT
<213> ORGANISM: Homo sapiens

<400> SEQUENCE: 47

Gln Leu Val Leu Thr Gln Ser Pro Ser Ala Ser Ala Ser Leu Gly Ala
  1               5                  10                  15
Ser Val Lys Leu Thr Cys Thr Leu Ser Ser Gln His Ser Thr Tyr Thr
                 20                  25                  30
Ile Glu Trp His Gln Gln Pro Glu Lys Gly Pro Arg Tyr Leu Met
                35                  40                  45
Lys Leu Lys Gln Asp Gly Ser His Ser Thr Gly Asp Gly Ile Pro Asp
         50                  55                  60
Arg Phe Ser Gly Ser Ser Ser Gly Ala Glu Arg Tyr Leu Thr Ile Ser
 65                  70                  75                  80
Ser Leu Gln Ser Glu Asp Glu Ala Asp Tyr Tyr Cys Gly Val Gly Asp
                 85                  90                  95
Thr Ile Lys Glu Gln Phe Val Tyr Val Phe Gly Gly Gly Thr Lys Leu
                100                 105                 110
Thr Val Leu Gly
            115

<210> SEQ ID NO 48
<211> LENGTH: 118
<212> TYPE: PRT
<213> ORGANISM: Homo sapiens

<400> SEQUENCE: 48

Gln Leu Val Leu Thr Gln Ser Pro Ser Ala Ser Ala Ser Leu Gly Ala
  1               5                  10                  15
Ser Val Lys Leu Thr Cys Thr Leu Ser Ser Gln His Ser Thr Tyr Thr
                 20                  25                  30
Ile Glu Trp Tyr Gln Gln Pro Glu Lys Gly Pro Lys Tyr Leu Met
                35                  40                  45
Asp Leu Lys Gln Asp Gly Ser His Ser Thr Gly Asp Gly Ile Pro Asp
         50                  55                  60
Arg Phe Ser Gly Ser Ser Ser Gly Ala Glu Arg Tyr Leu Thr Ile Ser
 65                  70                  75                  80
Ser Leu Gln Ser Glu Asp Glu Ala Asp Tyr Tyr Cys Gly Val Gly Asp
                 85                  90                  95
Thr Ile Lys Glu Gln Phe Val Tyr Val Phe Gly Gly Gly Thr Lys Leu
```

```
                100               105                110
Thr Val Leu Gly Gln Pro
        115

<210> SEQ ID NO 49
<211> LENGTH: 118
<212> TYPE: PRT
<213> ORGANISM: Homo sapiens

<400> SEQUENCE: 49

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Lys Tyr Val Met
            35                  40                  45

Asp Leu Lys Gln Asp Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 50
<211> LENGTH: 118
<212> TYPE: PRT
<213> ORGANISM: Homo sapiens

<400> SEQUENCE: 50

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Ser Thr Tyr Thr
                20                  25                  30

Ile Glu Trp Tyr Gln Gln Pro Glu Lys Gly Pro Arg Tyr Leu Met
            35                  40                  45

Asp Leu Lys Gln Asp Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 51
<211> LENGTH: 118
<212> TYPE: PRT
<213> ORGANISM: Homo sapiens

<400> SEQUENCE: 51

Gln Leu Val Leu Thr Gln Ser Pro Ser Ala Ser Ala Ser Leu Gly Ala
 1               5                  10                  15
```

```
Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Arg Tyr Val Met
        35                  40                  45

Asp Leu Lys Gln Asp Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 52
<211> LENGTH: 118
<212> TYPE: PRT
<213> ORGANISM: Homo sapiens

<400> SEQUENCE: 52

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Lys Tyr Leu Met
        35                  40                  45

Asp Leu Lys Gln Asp Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
            100                 105                 110

Thr Val Leu Gly Gln Pro
        115

<210> SEQ ID NO 53
<211> LENGTH: 118
<212> TYPE: PRT
<213> ORGANISM: Homo sapiens

<400> SEQUENCE: 53

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Pro Glu Lys Gly Pro Arg Tyr Leu Met
        35                  40                  45

Asp Leu Lys Gln Asp Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Ile Cys Gly Val Gly Asp
                85                  90                  95
```

```
Thr Ile Lys Glu Gln Phe Val Tyr Val Phe Gly Gly Gly Thr Lys Leu
                100                 105                 110

Thr Val Leu Gly Gln Pro
        115

<210> SEQ ID NO 54
<211> LENGTH: 118
<212> TYPE: PRT
<213> ORGANISM: Homo sapiens

<400> SEQUENCE: 54

Gln Leu Val Leu Thr Gln Ser Pro Ser Ala Ser Ala Ser Leu Gly Ala
  1               5                  10                  15

Ser Val Lys Leu Thr Cys Thr Leu Ser Ser Gln His Ser Thr Tyr Thr
               20                  25                  30

Ile Glu Trp Tyr Gln Gln Pro Glu Lys Gly Pro Lys Tyr Val Met
            35                  40                  45

Asp Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
                100                 105                 110

Thr Val Leu Gly Gln Pro
        115

<210> SEQ ID NO 55
<211> LENGTH: 118
<212> TYPE: PRT
<213> ORGANISM: Homo sapiens

<400> SEQUENCE: 55

Gln Leu Val Leu Thr Gln Ser Pro Ser Ala Ser Ala Ser Leu Gly Ala
  1               5                  10                  15

Ser Val Lys Leu Thr Cys Thr Leu Ser Ser Gln His Ser Thr Tyr Thr
               20                  25                  30

Ile Glu Trp Tyr Gln Gln Pro Glu Lys Gly Pro Arg Tyr Val Met
            35                  40                  45

Asp Leu Lys Gln Asp Gly Ser His Ser Thr Gly Asp Gly Ile Pro Asp
 50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Ile Cys Gly Val Gly Asp
                85                  90                  95

Thr Ile Lys Glu Gln Phe Val Tyr Val Phe Gly Gly Gly Thr Lys Leu
                100                 105                 110

Thr Val Leu Gly Gln Pro
        115

<210> SEQ ID NO 56
<211> LENGTH: 118
<212> TYPE: PRT
<213> ORGANISM: Homo sapiens

<400> SEQUENCE: 56
```

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met Ser Trp Val Arg Gln Ala Pro Gly Lys Gly Leu Glu Trp Val
         35                  40                  45

Ala Thr Ile Ser Ser Gly Gly Ser Tyr Thr Tyr Tyr Pro Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gln Thr Thr Met Thr Tyr Phe Ala Tyr Trp Gly Gln Gly Thr
             100                 105                 110

Leu Val Thr Val Ser Ser
             115

<210> SEQ ID NO 57
<211> LENGTH: 411
<212> TYPE: DNA
<213> ORGANISM: Mus musculus
<220> FEATURE:
<221> NAME/KEY: CDS
<222> LOCATION: (1)..(411)
<221> NAME/KEY: mat_peptide
<222> LOCATION: (58)..(411)

<400> SEQUENCE: 57 atg aac ttc ggg ctc agc ttg att ttc ctt gcc ctc att tta aaa ggt    48
Met Asn Phe Gly Leu Ser Leu Ile Phe Leu Ala Leu Ile Leu Lys Gly
             -15                 -10                  -5 gtc cag tgt gag gtg caa ctg gtg gag tct ggg gga gac tta gtg aag    96
Val Gln Cys Glu Val Gln Leu Val Glu Ser Gly Gly Asp Leu Val Lys
         -1   1                   5                  10 cct gga ggg tcc ctg aaa ctc tcc tgt gca gcc tct gga ttc act ttc   144
Pro Gly Gly Ser Leu Lys Leu Ser Cys Ala Ala Ser Gly Phe Thr Phe
     15                  20                  25 agt agc tat ggc atg tct tgg att cgc cag act cca gac aag agg ctg   192
Ser Ser Tyr Gly Met Ser Trp Ile Arg Gln Thr Pro Asp Lys Arg Leu
 30                  35                  40                  45 gag tgg gtc gca acc att agt agt ggt ggt agt tac acc tac tat cca   240
Glu Trp Val Ala Thr Ile Ser Ser Gly Gly Ser Tyr Thr Tyr Tyr Pro
             50                  55                  60 gac agt gtg aag ggg cga ttc acc atc tcc aga gac aat gcc aag aac   288
Asp Ser Val Lys Gly Arg Phe Thr Ile Ser Arg Asp Asn Ala Lys Asn
         65                  70                  75 acc cta tac ctg caa atg agc agt ctg aag tct gag gac aca gcc atg   336
Thr Leu Tyr Leu Gln Met Ser Ser Leu Lys Ser Glu Asp Thr Ala Met
     80                  85                  90 ttt tac tgt gca aga cag act act atg act tac ttt gct tac tgg ggc   384
Phe Tyr Cys Ala Arg Gln Thr Thr Met Thr Tyr Phe Ala Tyr Trp Gly
 95                 100                 105 caa ggg act ctg gtc act gtc tct gca                                411
Gln Gly Thr Leu Val Thr Val Ser Ala
110                 115

<210> SEQ ID NO 58
<211> LENGTH: 411
<212> TYPE: DNA
<213> ORGANISM: Homo sapiens
<220> FEATURE:
```

```
<221> NAME/KEY: CDS
<222> LOCATION: (1)..(411)
<221> NAME/KEY: mat_peptide
<222> LOCATION: (58)..(411)

<400> SEQUENCE: 58 atg ggg ttt ggg ctg agc tgg gtt ttc ctc gtt gct ctt tta aga ggt      48
Met Gly Phe Gly Leu Ser Trp Val Phe Leu Val Ala Leu Leu Arg Gly
            -15                 -10                 -5 gtc cag tgt cag gtg cag ctg gtg gag tct ggg gga ggc gtg gtc cag      96
Val Gln Cys Gln Val Gln Leu Val Glu Ser Gly Gly Gly Val Val Gln
     -1   1               5                  10 cct ggg agg tcc ctg aga ctc tcc tgt gca gcc tct gga ttc acc ttc     144
Pro Gly Arg Ser Leu Arg Leu Ser Cys Ala Ala Ser Gly Phe Thr Phe
         15                  20                  25 agt agc tat ggc atg tct tgg gtc cgc cag gct cca ggc aag ggg ctg     192
Ser Ser Tyr Gly Met Ser Trp Val Arg Gln Ala Pro Gly Lys Gly Leu
     30                  35                  40                  45 gag tgg gtg gca acc att agt agt ggt ggt agt tac acc tac tat cca     240
Glu Trp Val Ala Thr Ile Ser Ser Gly Gly Ser Tyr Thr Tyr Tyr Pro
                 50                  55                  60 gac agt gtg aag ggg cga ttc acc atc tcc aga gac aat tcc aag aac     288
Asp Ser Val Lys Gly Arg Phe Thr Ile Ser Arg Asp Asn Ser Lys Asn
             65                  70                  75 acg ctg tat ctg caa atg aac agc ctg aga gct gag gac acg gct gtg     336
Thr Leu Tyr Leu Gln Met Asn Ser Leu Arg Ala Glu Asp Thr Ala Val
         80                  85                  90 tat tac tgt gcg aga cag act act atg act tac ttt gct tac tgg ggc     384
Tyr Tyr Cys Ala Arg Gln Thr Thr Met Thr Tyr Phe Ala Tyr Trp Gly
     95                 100                 105 cag gga acc ctg gtc acc gtc tcc tca                                 411
Gln Gly Thr Leu Val Thr Val Ser Ser
110                 115

<210> SEQ ID NO 59
<211> LENGTH: 11
<212> TYPE: PRT
<213> ORGANISM: Homo sapiens

<400> SEQUENCE: 59

Lys Ala Ser Gln Asp Val Asn Thr Ala Val Ala
 1               5                  10

<210> SEQ ID NO 60
<211> LENGTH: 7
<212> TYPE: PRT
<213> ORGANISM: Homo sapiens

<400> SEQUENCE: 60

Ser Ala Ser Asn Arg Tyr Thr
 1               5

<210> SEQ ID NO 61
<211> LENGTH: 9
<212> TYPE: PRT
<213> ORGANISM: Homo sapiens

<400> SEQUENCE: 61

Gln Gln His Tyr Ser Thr Pro Phe Thr
 1               5

<210> SEQ ID NO 62
<211> LENGTH: 5
```

```
<212> TYPE: PRT
<213> ORGANISM: Homo sapiens

<400> SEQUENCE: 62

Pro Tyr Trp Met Gln
 1               5

<210> SEQ ID NO 63
<211> LENGTH: 16
<212> TYPE: PRT
<213> ORGANISM: Homo sapiens

<400> SEQUENCE: 63

Ser Ile Phe Gly Asp Gly Asp Thr Arg Tyr Ser Gln Lys Phe Lys Gly
 1               5                  10                  15

<210> SEQ ID NO 64
<211> LENGTH: 11
<212> TYPE: PRT
<213> ORGANISM: Homo sapiens

<400> SEQUENCE: 64

Gly Leu Arg Arg Gly Gly Tyr Tyr Phe Asp Tyr
 1               5                  10

<210> SEQ ID NO 65
<211> LENGTH: 411
<212> TYPE: DNA
<213> ORGANISM: Mus musculus
<220> FEATURE:
<221> NAME/KEY: CDS
<222> LOCATION: (1)..(411)
<221> NAME/KEY: mat_peptide
<222> LOCATION: (58)..(411)

<400> SEQUENCE: 65 atg gcc tgg act cct ctc ttc ttc ttt gtt ctt cat tgc tca ggt         48
Met Ala Trp Thr Pro Leu Phe Phe Phe Val Leu His Cys Ser Gly
            -15                 -10                 -5 tct ttc tcc caa ctt gtg ctc act cag tca tct tca gcc tct ttc tcc    96
Ser Phe Ser Gln Leu Val Leu Thr Gln Ser Ser Ser Ala Ser Phe Ser
        -1   1               5                  10 ctg gga gcc tca gca aaa ctc acg tgc acc ttg agt agt cag cac agt   144
Leu Gly Ala Ser Ala Lys Leu Thr Cys Thr Leu Ser Ser Gln His Ser
     15                  20                  25 acg tac acc att gaa tgg tat cag caa cag cca ctc aag cct cct aag   192
Thr Tyr Thr Ile Glu Trp Tyr Gln Gln Gln Pro Leu Lys Pro Pro Lys
 30                  35                  40                  45 tat gtg atg gat ctt aag caa gat gga agc cac agc aca ggt gat ggg   240
Tyr Val Met Asp Leu Lys Gln Asp Gly Ser His Ser Thr Gly Asp Gly
             50                  55                  60 att cct gat cgc ttc tct gga tcc agc tct ggt gct gat cgc tac ctt   288
Ile Pro Asp Arg Phe Ser Gly Ser Ser Ser Gly Ala Asp Arg Tyr Leu
         65                  70                  75 agc att tcc aac atc cag cca gaa gat gaa gca atg tac atc tgt ggt   336
Ser Ile Ser Asn Ile Gln Pro Glu Asp Glu Ala Met Tyr Ile Cys Gly
     80                  85                  90 gtg ggt gat aca att aag gaa caa ttt gtg tat gtt ttc ggc ggt ggg   384
Val Gly Asp Thr Ile Lys Glu Gln Phe Val Tyr Val Phe Gly Gly Gly
 95                 100                 105 acc aag gtc act gtc cta ggt cag ccc                               411
Thr Lys Val Thr Val Leu Gly Gln Pro
110             115
```

```
<210> SEQ ID NO 66
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: mat_peptide
<222> LOCATION: (58)..(411)

<400> SEQUENCE: 66 atg gcc tgg act cct ctc ttc ttc ttt gtt ctt cat tgc tca ggt        48
Met Ala Trp Thr Pro Leu Phe Phe Phe Val Leu His Cys Ser Gly
            -15                 -10                 -5 tct ttc tcc cag ctt gtg ctg act caa tcg ccc tct gcc tct gcc tcc    96
Ser Phe Ser Gln Leu Val Leu Thr Gln Ser Pro Ser Ala Ser Ala Ser
    -1  1               5                   10 ctg gga gcc tcg gtc aag ctc acc tgc acc ttg agt agt cag cac agt   144
Leu Gly Ala Ser Val Lys Leu Thr Cys Thr Leu Ser Ser Gln His Ser
 15                  20                  25 acg tac acc att gaa tgg cat cag cag cag cca gag aag ggc cct cgg   192
Thr Tyr Thr Ile Glu Trp His Gln Gln Gln Pro Glu Lys Gly Pro Arg
 30                  35                  40                  45 tac ttg atg aaa ctt aag caa gat gga agc cac agc aca ggt gat ggg   240
Tyr Leu Met Lys Leu Lys Gln Asp Gly Ser His Ser Thr Gly Asp Gly
                 50                  55                  60 att cct gat cgc ttc tca ggc tcc agc tct ggg gct gag cgc tac ctc   288
Ile Pro Asp Arg Phe Ser Gly Ser Ser Ser Gly Ala Glu Arg Tyr Leu
             65                  70                  75 acc atc tcc agc ctc cag tct gag gat gag gct gac tat tac tgt ggt   336
Thr Ile Ser Ser Leu Gln Ser Glu Asp Glu Ala Asp Tyr Tyr Cys Gly
         80                  85                  90 gtg ggt gat aca att aag gaa caa ttt gtg tac gtg ttc ggc gga ggg   384
Val Gly Asp Thr Ile Lys Glu Gln Phe Val Tyr Val Phe Gly Gly Gly
     95                 100                 105 acc aaa ctg acc gtc cta ggt cag ccc                               411
Thr Lys Leu Thr Val Leu Gly Gln Pro
110                 115

<210> SEQ ID NO 67
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: mat_peptide
<222> LOCATION: (58)..(411)

<400> SEQUENCE: 67 atg gcc tgg act cct ctc ttc ttc ttt gtt ctt cat tgc tca ggt        48
Met Ala Trp Thr Pro Leu Phe Phe Phe Val Leu His Cys Ser Gly
            -15                 -10                 -5 tct ttc tcc cag ctt gtg ctg act caa tcg ccc tct gcc tct gcc tcc    96
Ser Phe Ser Gln Leu Val Leu Thr Gln Ser Pro Ser Ala Ser Ala Ser
    -1  1               5                   10 ctg gga gcc tcg gtc aag ctc acc tgc acc ttg agt agt cag cac agt   144
Leu Gly Ala Ser Val Lys Leu Thr Cys Thr Leu Ser Ser Gln His Ser
 15                  20                  25 acg tac acc att gaa tgg tat cag cag cag cca gag aag ggc cct aag   192
Thr Tyr Thr Ile Glu Trp Tyr Gln Gln Gln Pro Glu Lys Gly Pro Lys
 30                  35                  40                  45 tac ctg atg gat ctt aag caa gat gga agc cac agc aca ggt gat ggg   240
Tyr Leu Met Asp Leu Lys Gln Asp Gly Ser His Ser Thr Gly Asp Gly
```

```
Tyr Leu Met Asp Leu Lys Gln Asp Gly Ser His Ser Thr Gly Asp Gly
            50                  55                  60 att cct gat cgc ttc tca ggc tcc agc tct ggg gct gag cgc tac ctc    288
Ile Pro Asp Arg Phe Ser Gly Ser Ser Ser Gly Ala Glu Arg Tyr Leu
                65                  70                  75 acc atc tcc agc ctc cag tct gag gat gag gct gac tat tac tgt ggt    336
Thr Ile Ser Ser Leu Gln Ser Glu Asp Glu Ala Asp Tyr Tyr Cys Gly
        80                  85                  90 gtg ggt gat aca att aag gaa caa ttt gtg tac gtg ttc ggc gga ggg    384
Val Gly Asp Thr Ile Lys Glu Gln Phe Val Tyr Val Phe Gly Gly Gly
    95                  100                 105 acc aaa ctg acc gtc cta ggc cag ccc                                411
Thr Lys Leu Thr Val Leu Gly Gln Pro
110             115

<210> SEQ ID NO 68
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: mat_peptide
<222> LOCATION: (58)..(411)

<400> SEQUENCE: 68 atg gcc tgg act cct ctc ttc ttc ttc ttt gtt ctt cat tgc tca ggt    48
Met Ala Trp Thr Pro Leu Phe Phe Phe Phe Val Leu His Cys Ser Gly
                -15                 -10                  -5 tct ttc tcc cag ctt gtg ctg act caa tcg ccc tct gcc tct gcc tcc    96
Ser Phe Ser Gln Leu Val Leu Thr Gln Ser Pro Ser Ala Ser Ala Ser
        -1   1                   5                  10 ctg gga gcc tcg gtc aag ctc acc tgc acc ttg agt agt cag cac agt    144
Leu Gly Ala Ser Val Lys Leu Thr Cys Thr Leu Ser Ser Gln His Ser
    15                  20                  25 acg tac acc att gaa tgg tat cag cag cag cca gag aag ggc cct aag    192
Thr Tyr Thr Ile Glu Trp Tyr Gln Gln Gln Pro Glu Lys Gly Pro Lys
30                  35                  40                  45 tac gtg atg gat ctt aag caa gat gga agc cac agc aca ggt gat ggg    240
Tyr Val Met Asp Leu Lys Gln Asp Gly Ser His Ser Thr Gly Asp Gly
            50                  55                  60 att cct gat cgc ttc tca ggc tcc agc tct ggg gct gag cgc tac ctc    288
Ile Pro Asp Arg Phe Ser Gly Ser Ser Ser Gly Ala Glu Arg Tyr Leu
                65                  70                  75 acc atc tcc agc ctc cag tct gag gat gag gct gac tat tac tgt ggt    336
Thr Ile Ser Ser Leu Gln Ser Glu Asp Glu Ala Asp Tyr Tyr Cys Gly
        80                  85                  90 gtg ggt gat aca att aag gaa caa ttt gtg tac gtg ttc ggc gga ggg    384
Val Gly Asp Thr Ile Lys Glu Gln Phe Val Tyr Val Phe Gly Gly Gly
    95                  100                 105 acc aaa ctg acc gtc cta ggc cag ccc                                411
Thr Lys Leu Thr Val Leu Gly Gln Pro
110             115

<210> SEQ ID NO 69
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: mat_peptide
<222> LOCATION: (58)..(411)
```

-continued

```
<400> SEQUENCE: 69 atg gcc tgg act cct ctc ttc ttc ttt gtt ctt cat tgc tca ggt        48
Met Ala Trp Thr Pro Leu Phe Phe Phe Val Leu His Cys Ser Gly
            -15                 -10                 -5 tct ttc tcc cag ctt gtg ctg act caa tcg ccc tct gcc tct gcc tcc    96
Ser Phe Ser Gln Leu Val Leu Thr Gln Ser Pro Ser Ala Ser Ala Ser
         -1   1               5                  10 ctg gga gcc tcg gtc aag ctc acc tgc acc ttg agt agt cag cac agt   144
Leu Gly Ala Ser Val Lys Leu Thr Cys Thr Leu Ser Ser Gln His Ser
     15                  20                  25 acg tac acc att gaa tgg tat cag cag cag cca gag aag ggc cct agg   192
Thr Tyr Thr Ile Glu Trp Tyr Gln Gln Gln Pro Glu Lys Gly Pro Arg
 30                  35                  40                  45 tac ctg atg gat ctt aag caa gat gga agc cac agc aca ggt gat ggg   240
Tyr Leu Met Asp Leu Lys Gln Asp Gly Ser His Ser Thr Gly Asp Gly
             50                  55                  60 att cct gat cgc ttc tca ggc tcc agc tct ggg gct gag cgc tac ctc   288
Ile Pro Asp Arg Phe Ser Gly Ser Ser Ser Gly Ala Glu Arg Tyr Leu
         65                  70                  75 acc atc tcc agc ctc cag tct gag gat gag gct gac tat tac tgt ggt   336
Thr Ile Ser Ser Leu Gln Ser Glu Asp Glu Ala Asp Tyr Tyr Cys Gly
         80                  85                  90 gtg ggt gat aca att aag gaa caa ttt gtg tac gtg ttc ggc gga ggg   384
Val Gly Asp Thr Ile Lys Glu Gln Phe Val Tyr Val Phe Gly Gly Gly
     95                 100                 105 acc aaa ctg acc gtc cta ggc cag ccc                               411
Thr Lys Leu Thr Val Leu Gly Gln Pro
110                 115

<210> SEQ ID NO 70
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: mat_peptide
<222> LOCATION: (58)..(411)

<400> SEQUENCE: 70 atg gcc tgg act cct ctc ttc ttc ttt gtt ctt cat tgc tca ggt        48
Met Ala Trp Thr Pro Leu Phe Phe Phe Val Leu His Cys Ser Gly
            -15                 -10                 -5 tct ttc tcc cag ctt gtg ctg act caa tcg ccc tct gcc tct gcc tcc    96
Ser Phe Ser Gln Leu Val Leu Thr Gln Ser Pro Ser Ala Ser Ala Ser
         -1   1               5                  10 ctg gga gcc tcg gtc aag ctc acc tgc acc ttg agt agt cag cac agt   144
Leu Gly Ala Ser Val Lys Leu Thr Cys Thr Leu Ser Ser Gln His Ser
     15                  20                  25 acg tac acc att gaa tgg tat cag cag cag cca gag aag ggc cct agg   192
Thr Tyr Thr Ile Glu Trp Tyr Gln Gln Gln Pro Glu Lys Gly Pro Arg
 30                  35                  40                  45 tac gtg atg gat ctt aag caa gat gga agc cac agc aca ggt gat ggg   240
Tyr Val Met Asp Leu Lys Gln Asp Gly Ser His Ser Thr Gly Asp Gly
             50                  55                  60 att cct gat cgc ttc tca ggc tcc agc tct ggg gct gag cgc tac ctc   288
Ile Pro Asp Arg Phe Ser Gly Ser Ser Ser Gly Ala Glu Arg Tyr Leu
         65                  70                  75 acc atc tcc agc ctc cag tct gag gat gag gct gac tat tac tgt ggt   336
Thr Ile Ser Ser Leu Gln Ser Glu Asp Glu Ala Asp Tyr Tyr Cys Gly
         80                  85                  90
```

| | |
|---|---|
| gtg ggt gat aca att aag gaa caa ttt gtg tac gtg ttc ggc gga ggg<br>Val Gly Asp Thr Ile Lys Glu Gln Phe Val Tyr Val Phe Gly Gly Gly<br>    95                  100                  105 | 384 |
| acc aaa ctg acc gtc cta ggc cag ccc<br>Thr Lys Leu Thr Val Leu Gly Gln Pro<br>110               115 | 411 |

<210> SEQ ID NO 71
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: mat_peptide
<222> LOCATION: (58)..(411)

<400> SEQUENCE: 71

| | |
|---|---|
| atg gcc tgg act cct ctc ttc ttc ttt gtt ctt cat tgc tca ggt<br>Met Ala Trp Thr Pro Leu Phe Phe Phe Val Leu His Cys Ser Gly<br>          -15                  -10               -5 | 48 |
| tct ttc tcc cag ctt gtg ctg act caa tcg ccc tct gcc tct gcc tcc<br>Ser Phe Ser Gln Leu Val Leu Thr Gln Ser Pro Ser Ala Ser Ala Ser<br>     -1  1              5                    10 | 96 |
| ctg gga gcc tcg gtc aag ctc acc tgc acc ttg agt agt cag cac agt<br>Leu Gly Ala Ser Val Lys Leu Thr Cys Thr Leu Ser Ser Gln His Ser<br>15                  20                  25 | 144 |
| acg tac acc att gaa tgg tat cag cag cag cca gag aag ggc cct aag<br>Thr Tyr Thr Ile Glu Trp Tyr Gln Gln Gln Pro Glu Lys Gly Pro Lys<br>30                  35                  40                  45 | 192 |
| tac ctg atg gat ctt aag caa gat gga agc cac agc aca ggt gat ggg<br>Tyr Leu Met Asp Leu Lys Gln Asp Gly Ser His Ser Thr Gly Asp Gly<br>             50                  55                  60 | 240 |
| att cct gat cgc ttc tca ggc tcc agc tct ggg gct gag cgc tac ctc<br>Ile Pro Asp Arg Phe Ser Gly Ser Ser Ser Gly Ala Glu Arg Tyr Leu<br>                65                  70                  75 | 288 |
| acc atc tcc agc ctc cag tct gag gat gag gct gac tat atc tgt ggt<br>Thr Ile Ser Ser Leu Gln Ser Glu Asp Glu Ala Asp Tyr Ile Cys Gly<br>80                  85                  90 | 336 |
| gtg ggt gat aca att aag gaa caa ttt gtg tac gtg ttc ggc gga ggg<br>Val Gly Asp Thr Ile Lys Glu Gln Phe Val Tyr Val Phe Gly Gly Gly<br>    95                  100                  105 | 384 |
| acc aaa ctg acc gtc cta ggc cag ccc<br>Thr Lys Leu Thr Val Leu Gly Gln Pro<br>110               115 | 411 |

<210> SEQ ID NO 72
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: mat_peptide
<222> LOCATION: (58)..(411)

<400> SEQUENCE: 72

| | |
|---|---|
| atg gcc tgg act cct ctc ttc ttc ttt gtt ctt cat tgc tca ggt<br>Met Ala Trp Thr Pro Leu Phe Phe Phe Val Leu His Cys Ser Gly<br>          -15                  -10               -5 | 48 |
| tct ttc tcc cag ctt gtg ctg act caa tcg ccc tct gcc tct gcc tcc<br>Ser Phe Ser Gln Leu Val Leu Thr Gln Ser Pro Ser Ala Ser Ala Ser<br>     -1  1              5                    10 | 96 |
| ctg gga gcc tcg gtc aag ctc acc tgc acc ttg agt agt cag cac agt | 144 |

```
Leu Gly Ala Ser Val Lys Leu Thr Cys Thr Leu Ser Ser Gln His Ser
         15                  20                  25 acg tac acc att gaa tgg tat cag cag cag cca gag aag ggc cct agg       192
Thr Tyr Thr Ile Glu Trp Tyr Gln Gln Gln Pro Glu Lys Gly Pro Arg
         30                  35                  40                  45 tac ctg atg gat ctt aag caa gat gga agc cac agc aca ggt gat ggg       240
Tyr Leu Met Asp Leu Lys Gln Asp Gly Ser His Ser Thr Gly Asp Gly
                     50                  55                  60 att cct gat cgc ttc tca ggc tcc agc tct ggg gct gag cgc tac ctc       288
Ile Pro Asp Arg Phe Ser Gly Ser Ser Ser Gly Ala Glu Arg Tyr Leu
                 65                  70                  75 acc atc tcc agc ctc cag tct gag gat gag gct gac tat atc tgt ggt       336
Thr Ile Ser Ser Leu Gln Ser Glu Asp Glu Ala Asp Tyr Ile Cys Gly
             80                  85                  90 gtg ggt gat aca att aag gaa caa ttt gtg tac gtg ttc ggc gga ggg       384
Val Gly Asp Thr Ile Lys Glu Gln Phe Val Tyr Val Phe Gly Gly Gly
         95                 100                 105 acc aaa ctg acc gtc cta ggc cag ccc                                   411
Thr Lys Leu Thr Val Leu Gly Gln Pro
110             115
```

<210> SEQ ID NO 73
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: mat_peptide
<222> LOCATION: (58)..(411)

<400> SEQUENCE: 73

```
atg gcc tgg act cct ctc ttc ttc ttc ttt gtt ctt cat tgc tca ggt        48
Met Ala Trp Thr Pro Leu Phe Phe Phe Phe Val Leu His Cys Ser Gly
             -15                 -10                  -5 tct ttc tcc cag ctt gtg ctg act caa tcg ccc tct gcc tct gcc tcc        96
Ser Phe Ser Gln Leu Val Leu Thr Gln Ser Pro Ser Ala Ser Ala Ser
         -1   1               5                  10 ctg gga gcc tcg gtc aag ctc acc tgc acc ttg agt agt cag cac agt       144
Leu Gly Ala Ser Val Lys Leu Thr Cys Thr Leu Ser Ser Gln His Ser
         15                  20                  25 acg tac acc att gaa tgg tat cag cag cag cca gag aag ggc cct aag       192
Thr Tyr Thr Ile Glu Trp Tyr Gln Gln Gln Pro Glu Lys Gly Pro Lys
         30                  35                  40                  45 tac gtg atg gat ctt aag caa gat gga agc cac agc aca ggt gat ggg       240
Tyr Val Met Asp Leu Lys Gln Asp Gly Ser His Ser Thr Gly Asp Gly
                     50                  55                  60 att cct gat cgc ttc tca ggc tcc agc tct ggg gct gag cgc tac ctc       288
Ile Pro Asp Arg Phe Ser Gly Ser Ser Ser Gly Ala Glu Arg Tyr Leu
                 65                  70                  75 acc atc tcc agc ctc cag tct gag gat gag gct gac tat atc tgt ggt       336
Thr Ile Ser Ser Leu Gln Ser Glu Asp Glu Ala Asp Tyr Ile Cys Gly
             80                  85                  90 gtg ggt gat aca att aag gaa caa ttt gtg tac gtg ttc ggc gga ggg       384
Val Gly Asp Thr Ile Lys Glu Gln Phe Val Tyr Val Phe Gly Gly Gly
         95                 100                 105 acc aaa ctg acc gtc cta ggc cag ccc                                   411
Thr Lys Leu Thr Val Leu Gly Gln Pro
110             115
```

<210> SEQ ID NO 74
<211> LENGTH: 411

```
<212> TYPE: DNA
<213> ORGANISM: Homo sapiens
<220> FEATURE:
<221> NAME/KEY: CDS
<222> LOCATION: (1)..(411)
<221> NAME/KEY: mat_peptide
<222> LOCATION: (58)..(411)

<400> SEQUENCE: 74 atg gcc tgg act cct ctc ttc ttc ttt gtt ctt cat tgc tca ggt         48
Met Ala Trp Thr Pro Leu Phe Phe Phe Val Leu His Cys Ser Gly
            -15                 -10                  -5 tct ttc tcc cag ctt gtg ctg act caa tcg ccc tct gcc tct gcc tcc     96
Ser Phe Ser Gln Leu Val Leu Thr Gln Ser Pro Ser Ala Ser Ala Ser
         -1   1               5                  10 ctg gga gcc tcg gtc aag ctc acc tgc acc ttg agt agt cag cac agt     144
Leu Gly Ala Ser Val Lys Leu Thr Cys Thr Leu Ser Ser Gln His Ser
     15                  20                  25 acg tac acc att gaa tgg tat cag cag cag cca gag aag ggc cct agg     192
Thr Tyr Thr Ile Glu Trp Tyr Gln Gln Gln Pro Glu Lys Gly Pro Arg
 30                  35                  40                  45 tac gtg atg gat ctt aag caa gat gga agc cac agc aca ggt gat ggg     240
Tyr Val Met Asp Leu Lys Gln Asp Gly Ser His Ser Thr Gly Asp Gly
                 50                  55                  60 att cct gat cgc ttc tca ggc tcc agc tct ggg gct gag cgc tac ctc     288
Ile Pro Asp Arg Phe Ser Gly Ser Ser Ser Gly Ala Glu Arg Tyr Leu
             65                  70                  75 acc atc tcc agc ctc cag tct gag gat gag gct gac tat atc tgt ggt     336
Thr Ile Ser Ser Leu Gln Ser Glu Asp Glu Ala Asp Tyr Ile Cys Gly
         80                  85                  90 gtg ggt gat aca att aag gaa caa ttt gtg tac gtg ttc ggc gga ggg     384
Val Gly Asp Thr Ile Lys Glu Gln Phe Val Tyr Val Phe Gly Gly Gly
     95                  100                 105 acc aaa ctg acc gtc cta ggc cag ccc                                 411
Thr Lys Leu Thr Val Leu Gly Gln Pro
110             115

<210> SEQ ID NO 75
<211> LENGTH: 34
<212> TYPE: PRT
<213> ORGANISM: Homo sapiens

<400> SEQUENCE: 75

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
             20                  25                  30

Thr Ala
```